(12) United States Patent
Leung et al.

(10) Patent No.: US 9,398,930 B2
(45) Date of Patent: Jul. 26, 2016

(54) PERCUTANEOUS METHODS AND DEVICES FOR CAROTID BODY ABLATION

(71) Applicant: Cibiem, Inc., Los Altos, CA (US)

(72) Inventors: Mark Leung, Shawnigan Lake (CA); Brett Schleicher, New York, NY (US); Charles Lennox, Hudson, NH (US); Ary Chernomorsky, Walnut Creek, CA (US); Zoar Jacob Engelman, Salt Lake City, UT (US); Marat Fudim, Duesseldorf (DE); Martin M. Grasse, Boston, MA (US); Mark Gelfand, New York, NY (US); Howard Levin, Teaneck, NJ (US)

(73) Assignee: CIBIEM, INC., Los Altos, CA (US)

( * ) Notice: Subject to any disclaimer, the term of this patent is extended or adjusted under 35 U.S.C. 154(b) by 105 days.

(21) Appl. No.: 13/908,995

(22) Filed: Jun. 3, 2013

(65) Prior Publication Data

US 2013/0324989 A1     Dec. 5, 2013

Related U.S. Application Data

(60) Provisional application No. 61/654,221, filed on Jun. 1, 2012, provisional application No. 61/666,384, filed on Jun. 29, 2012.

(51) Int. Cl.
*A61B 18/02*     (2006.01)
*A61B 8/08*     (2006.01)
*A61B 8/00*     (2006.01)
(Continued)

(52) U.S. Cl.
CPC ............... *A61B 18/02* (2013.01); *A61B 8/0841* (2013.01); *A61B 8/4227* (2013.01); *A61B 8/0891* (2013.01); *A61B 8/12* (2013.01); *A61B 8/145* (2013.01); *A61B 8/488* (2013.01); *A61B 18/1477* (2013.01); *A61B 18/22* (2013.01); *A61B 2018/00041* (2013.01); *A61B 2018/00404* (2013.01); *A61B 2018/00791* (2013.01);
(Continued)

(58) Field of Classification Search
CPC ........... A61B 2018/00005; A61B 2018/00011; A61B 2018/00017; A61B 2018/00023; A61B 2018/00041; A61B 2018/00404; A61B 2018/0293
See application file for complete search history.

(56) References Cited

U.S. PATENT DOCUMENTS

| 3,650,277 | A | 3/1972 | Sjostrand et al. |
| 4,201,219 | A | 5/1980 | Bozal |

(Continued)

FOREIGN PATENT DOCUMENTS

| CN | 1440256 A | 9/2003 |
| DE | 10151797 A1 | 5/2003 |

(Continued)

OTHER PUBLICATIONS

Abboud, F.; In search of autonomic balance: the good, the bad, and the ugly; Am J Physiol Regul Integr Comp Physiol; 298; pp. R1449-R1467; Jun. 2010.

(Continued)

*Primary Examiner* — Ronald Hupczey, Jr.
(74) *Attorney, Agent, or Firm* — Shay Glenn LLP

(57) ABSTRACT

Methods and percutaneous devices for assessing, and treating patients having sympathetically mediated disease, involving augmented peripheral chemoreflex and heightened sympathetic tone by reducing chemosensor input to the nervous system via percutaneous carotid body ablation.

9 Claims, 29 Drawing Sheets

(51) Int. Cl.
*A61B 18/00* (2006.01)
*A61N 7/02* (2006.01)
*A61B 18/14* (2006.01)
*A61B 18/22* (2006.01)
*A61B 8/12* (2006.01)
*A61B 8/14* (2006.01)
*A61N 7/00* (2006.01)

(52) U.S. Cl.
CPC ...... *A61B 2018/0212* (2013.01); *A61B 2018/0293* (2013.01); *A61N 7/022* (2013.01); *A61N 2007/0026* (2013.01)

(56) References Cited

U.S. PATENT DOCUMENTS

| | | | |
|---|---|---|---|
| 4,791,931 A | 12/1988 | Slate |
| 4,960,133 A | 10/1990 | Hewson |
| 5,139,496 A | 8/1992 | Hed et al. |
| 5,354,271 A | 10/1994 | Voda |
| 5,476,495 A | 12/1995 | Kordis et al. |
| 5,906,580 A | 5/1999 | Kline-Schoder et al. |
| 5,916,213 A | 6/1999 | Haissaguerre et al. |
| 5,919,187 A | 7/1999 | Guglielmi et al. |
| 5,957,882 A | 9/1999 | Nita et al. |
| 6,004,269 A | 12/1999 | Crowley et al. |
| 6,068,629 A | 5/2000 | Haissaguerre et al. |
| 6,071,279 A | 6/2000 | Whayne et al. |
| 6,125,857 A | 10/2000 | Silber |
| 6,129,359 A | 10/2000 | Haas et al. |
| 6,182,666 B1 | 2/2001 | Dobak, III |
| 6,217,576 B1 | 4/2001 | Tu et al. |
| 6,228,082 B1 | 5/2001 | Baker et al. |
| 6,235,024 B1 | 5/2001 | Tu |
| 6,379,348 B1 | 4/2002 | Onik |
| 6,402,746 B1 | 6/2002 | Whayne et al. |
| 6,411,852 B1 | 6/2002 | Danek et al. |
| 6,497,705 B2 | 12/2002 | Comben |
| 6,522,926 B1 | 2/2003 | Kieval et al. |
| 6,544,187 B2 | 4/2003 | Seward |
| 6,656,136 B1 | 12/2003 | Weng et al. |
| 6,660,013 B2 | 12/2003 | Rabiner et al. |
| 6,673,066 B2 | 1/2004 | Werneth |
| 6,905,497 B2 | 6/2005 | Truckai et al. |
| 6,937,903 B2 | 8/2005 | Schuler et al. |
| 7,097,641 B1 | 8/2006 | Arless et al. |
| 7,137,963 B2 | 11/2006 | Nita et al. |
| 7,149,574 B2 | 12/2006 | Yun et al. |
| 7,155,284 B1 | 12/2006 | Whitehurst et al. |
| 7,162,303 B2 | 1/2007 | Levin et al. |
| 7,207,989 B2 | 4/2007 | Pike et al. |
| 7,363,076 B2 | 4/2008 | Yun et al. |
| 7,617,005 B2 | 11/2009 | Demarais et al. |
| 7,628,785 B2 | 12/2009 | Hadjicostis et al. |
| 7,736,360 B2 | 6/2010 | Mody et al. |
| 7,738,952 B2 | 6/2010 | Yun et al. |
| 7,766,961 B2 | 8/2010 | Patel et al. |
| 7,853,333 B2 | 12/2010 | Demarais |
| 7,901,450 B2 | 3/2011 | Johnson et al. |
| 7,922,663 B2 | 4/2011 | Tran et al. |
| 7,925,352 B2 | 4/2011 | Stack et al. |
| 7,959,628 B2 | 6/2011 | Schaer et al. |
| 8,002,728 B2 | 8/2011 | Chang |
| 8,060,206 B2 | 11/2011 | Kieval et al. |
| 8,075,554 B2 | 12/2011 | Malecki et al. |
| 8,116,883 B2 | 2/2012 | Williams et al. |
| 8,157,760 B2 | 4/2012 | Criado et al. |
| 8,167,805 B2 | 5/2012 | Emery et al. |
| 8,192,425 B2 | 6/2012 | Mirza et al. |
| 8,192,760 B2 | 6/2012 | Hossainy et al. |
| 8,292,879 B2 | 10/2012 | Manwaring et al. |
| 8,295,912 B2 | 10/2012 | Gertner |
| 8,308,709 B2 | 11/2012 | Chang |
| 8,326,429 B2 | 12/2012 | Wenzel et al. |
| 8,364,237 B2 | 1/2013 | Stone et al. |
| 8,374,674 B2 | 2/2013 | Gertner |
| 8,396,548 B2 | 3/2013 | Perry et al. |
| 8,409,200 B2 | 4/2013 | Holcomb et al. |
| 8,433,423 B2 | 4/2013 | Demarais |
| 8,465,752 B2 | 6/2013 | Seward |
| 8,469,904 B2 | 6/2013 | Gertner |
| 8,568,399 B2 | 10/2013 | Azamian et al. |
| 8,620,423 B2 | 12/2013 | Demarais et al. |
| 9,060,784 B2 | 6/2015 | Coe et al. |
| 9,089,541 B2 | 7/2015 | Azamian |
| 2001/0041890 A1 | 11/2001 | Hassett et al. |
| 2002/0087151 A1 | 7/2002 | Mody et al. |
| 2002/0128639 A1 | 9/2002 | Pless et al. |
| 2003/0009125 A1 | 1/2003 | Nita et al. |
| 2004/0116921 A1 | 6/2004 | Sherman et al. |
| 2004/0210239 A1 | 10/2004 | Nash et al. |
| 2005/0096642 A1 | 5/2005 | Appling et al. |
| 2005/0096710 A1 | 5/2005 | Kieval |
| 2005/0143378 A1 | 6/2005 | Yun et al. |
| 2005/0153885 A1 | 7/2005 | Yun et al. |
| 2005/0288656 A1 | 12/2005 | Koerner et al. |
| 2006/0064137 A1 | 3/2006 | Stone |
| 2006/0111754 A1 | 5/2006 | Rezai et al. |
| 2006/0135962 A1 | 6/2006 | Kick et al. |
| 2006/0195149 A1 | 8/2006 | Hopper et al. |
| 2006/0224110 A1 | 10/2006 | Scott et al. |
| 2006/0253161 A1 | 11/2006 | Libbus et al. |
| 2006/0259084 A1 | 11/2006 | Zhang et al. |
| 2006/0282131 A1 | 12/2006 | Caparso et al. |
| 2006/0287679 A1 | 12/2006 | Stone |
| 2007/0015006 A1 | 1/2007 | Lee et al. |
| 2007/0112327 A1 | 5/2007 | Yun et al. |
| 2007/0135875 A1 | 6/2007 | Demarais et al. |
| 2007/0150006 A1 | 6/2007 | Libbus et al. |
| 2007/0156179 A1 | 7/2007 | Karashurov |
| 2007/0265609 A1 | 11/2007 | Thapliyal et al. |
| 2007/0299476 A1 | 12/2007 | Park et al. |
| 2008/0009916 A1 | 1/2008 | Rossing et al. |
| 2008/0009917 A1 | 1/2008 | Rossing et al. |
| 2008/0039727 A1 | 2/2008 | Babaev |
| 2008/0045936 A1 | 2/2008 | Vaska et al. |
| 2008/0058871 A1 | 3/2008 | Libbus et al. |
| 2008/0086181 A1 | 4/2008 | Amurthur et al. |
| 2010/0063564 A1 | 3/2010 | Libbus et al. |
| 2010/0070004 A1 | 3/2010 | Hlavka |
| 2010/0152590 A1 | 6/2010 | Moore et al. |
| 2010/0168731 A1 | 7/2010 | Wu et al. |
| 2010/0168739 A1 | 7/2010 | Wu et al. |
| 2010/0262013 A1 | 10/2010 | Smith et al. |
| 2010/0268307 A1 | 10/2010 | Demarais et al. |
| 2010/0274219 A1 | 10/2010 | Wenzel et al. |
| 2011/0009854 A1 | 1/2011 | Babkin et al. |
| 2011/0040297 A1 | 2/2011 | Babkin et al. |
| 2011/0066085 A1 | 3/2011 | Weng et al. |
| 2011/0098699 A1 | 4/2011 | Pachon Mateos et al. |
| 2011/0104060 A1 | 5/2011 | Seward |
| 2011/0118598 A1 | 5/2011 | Gertner |
| 2011/0118600 A1 | 5/2011 | Gertner |
| 2011/0130708 A1 | 6/2011 | Perry et al. |
| 2011/0144631 A1 | 6/2011 | Elkins et al. |
| 2011/0172529 A1 | 7/2011 | Gertner |
| 2011/0208096 A1 | 8/2011 | Demarais et al. |
| 2011/0208174 A1 | 8/2011 | Baust |
| 2011/0208175 A1 | 8/2011 | Sobotka et al. |
| 2011/0251487 A1 | 10/2011 | Magnin et al. |
| 2011/0251607 A1 | 10/2011 | Kruecker et al. |
| 2011/0257561 A1 | 10/2011 | Gertner et al. |
| 2011/0257562 A1 | 10/2011 | Schaer |
| 2011/0301587 A1 | 12/2011 | Deem et al. |
| 2012/0016226 A1 | 1/2012 | Gertner |
| 2012/0059437 A1 | 3/2012 | Shalev |
| 2012/0065492 A1 | 3/2012 | Gertner et al. |
| 2012/0065494 A1 | 3/2012 | Gertner et al. |
| 2012/0078248 A1 | 3/2012 | Worrell et al. |
| 2012/0095335 A1 | 4/2012 | Sverdlik et al. |
| 2012/0095371 A1 | 4/2012 | Sverdlik et al. |
| 2012/0095372 A1 | 4/2012 | Sverdlik et al. |
| 2012/0095461 A1 | 4/2012 | Herscher et al. |
| 2012/0101018 A1 | 4/2012 | Miracle et al. |

(56) References Cited

U.S. PATENT DOCUMENTS

| | | |
|---|---|---|
| 2012/0109018 A1 | 5/2012 | Gertner et al. |
| 2012/0130368 A1 | 5/2012 | Jenson |
| 2012/0157992 A1 | 6/2012 | Smith et al. |
| 2012/0157993 A1 | 6/2012 | Jenson et al. |
| 2012/0172680 A1* | 7/2012 | Gelfand et al. ............... 600/301 |
| 2012/0172723 A1 | 7/2012 | Gertner |
| 2012/0184952 A1 | 7/2012 | Jenson et al. |
| 2012/0199616 A1 | 8/2012 | Lamb et al. |
| 2012/0232436 A1 | 9/2012 | Warnking |
| 2012/0238918 A1 | 9/2012 | Gertner |
| 2012/0245494 A1 | 9/2012 | Gertner |
| 2012/0265227 A1 | 10/2012 | Sverdlik et al. |
| 2012/0277763 A1 | 11/2012 | Greenblatt et al. |
| 2013/0066316 A1 | 3/2013 | Steinke et al. |
| 2013/0123778 A1 | 5/2013 | Richardson et al. |
| 2013/0131668 A1 | 5/2013 | Schaer |
| 2013/0197555 A1 | 8/2013 | Schaer |
| 2013/0197614 A1 | 8/2013 | Gustus et al. |
| 2014/0039450 A1 | 2/2014 | Green et al. |
| 2014/0243809 A1 | 8/2014 | Gelfand et al. |
| 2014/0288015 A1 | 9/2014 | Venkateswara-Rao et al. |
| 2014/0350401 A1 | 11/2014 | Sinelnikov |
| 2015/0045675 A1 | 2/2015 | Chernomorsky |
| 2015/0257779 A1 | 9/2015 | Sinelnikov |
| 2015/0328452 A1 | 11/2015 | Hlavka et al. |

FOREIGN PATENT DOCUMENTS

| | | |
|---|---|---|
| EP | 0819014 B1 | 2/2003 |
| EP | 2488250 A | 8/2012 |
| EP | 1299035 B1 | 2/2013 |
| WO | WO97/25916 A1 | 7/1997 |
| WO | WO98/43701 A1 | 10/1998 |
| WO | WO00/25685 A1 | 5/2000 |
| WO | WO02/069862 A1 | 9/2002 |
| WO | WO03/076008 A1 | 9/2003 |
| WO | WO2004/086936 A2 | 10/2004 |
| WO | WO2004/105807 A2 | 12/2004 |
| WO | WO2007/092330 A1 | 8/2007 |
| WO | WO2007/146834 A2 | 12/2007 |
| WO | WO2008/025855 A2 | 3/2008 |
| WO | WO2010/093603 A1 | 8/2010 |
| WO | WO2010/121738 A1 | 10/2010 |
| WO | WO2010/124120 A1 | 10/2010 |
| WO | WO2010/132703 A1 | 11/2010 |
| WO | WO2011/082278 A1 | 7/2011 |
| WO | WO2011/130531 A2 | 10/2011 |
| WO | WO2012/015720 A1 | 2/2012 |
| WO | WO2012/015721 A1 | 2/2012 |
| WO | WO2012/015722 A1 | 2/2012 |
| WO | WO2012/016135 A1 | 2/2012 |
| WO | WO2012/057916 A1 | 5/2012 |
| WO | WO2012/112165 A1 | 8/2012 |
| WO | WO2012/125172 A1 | 9/2012 |
| WO | WO2013/018083 A2 | 2/2013 |
| WO | WO2013/074813 A1 | 5/2013 |
| WO | WO2013/157011 A2 | 10/2013 |
| WO | WO2015/103539 A1 | 7/2015 |

OTHER PUBLICATIONS

Abdala et al; Hypertension is critically dependent on the carotid body input in the spontaneously hypertensive rat; J Physiol; 590(17); pp. 4269-4277; Sep. 2012.

Abdala et al; Peripheral chemoreceptor inputs contribute to the development of high blood pressure in spontaneously hypertensive rats(proceeding abstract); Proc Physiol Soc 23; PC22; Oxford, England; Jul. 2011 (printed Sep. 24, 2013 from: http://www.physoc.org/proceedings/abstract/Proc%20Physiol%20Soc%2023PC22).

Al-Rawi et al.; Effect of lignocaine injection in carotid sinus on baroreceptor sensitivity during carotid endarterectomy; J Vasc Surg; 39(6); pp. 1288-1294; Jun. 2004.

Anand et al.; Management of the internal carotid artery during carotid body tumor surgery; Laryngoscope; 105; pp. 231-235; Mar. 1995.

Anderson et al. (executive committee); Carotid body resection; J. Allergy Clin. Immunol.; 78(2); pp. 273-275; Aug. 1986.

Arena et al.; Prognostic value of resting end-tidal carbon dioxide in patients with heart failure; Int J Cardiol; 109(3); pp. 351-358; May 2006.

Banzett et al.; Dyspnea and pain: similarities and contrasts between two very unpleasant sensations; APS Bulletin; 11(1); 6 pgs.; Mar./Apr. 2001.

Bencini et al.; The carotid bodies in bronchial asthma; Histopathology; 18; pp. 195-200; Mar. 1991.

Bencini, A.; Reduction of reflex bronchotropic impulses as a result of carotid body surgery; International Surgery; 54(6); pp. 415-423; Dec. 1970.

Bernstein et al.; Current status of glomectomy; (The Amer. Acad. of Allergy, Abstracts of papers given at Ann. Meeting, Feb. 3-7, 1978, Boston MA; J. Allergy; 41(2); pp. 88-89; Feb. 1968.

Bishop, Jr. et al.; Paragangliomas of the neck; Arch Surg.; 127; pp. 1441-1445; Dec. 1992.

Braunwald et al.; Carotid sinus nerve stimulation for the treatment of intractable angina pectoris: surgical technic; Annals of Surgery; 172(5); pp. 870-876; Nov. 1970.

Braunwald et al.; Carotid sinus nerve stimulation in the treatment of angina pectoris and supraventricular tachycardia; The Western Journal of Medicine; 112(3); pp. 41-50; Mar. 1970.

Capps et al.; The late effects of bilateral carotid sinus denervation in man; J Clin Invest; 17(4); pp. 385-389; Jul. 1938.

Chang et al.; Impaired response to hypoxia after bilateral carotid body resection for treatment of bronchial asthma; Chest; 73; pp. 667-669; May 1978.

Curran et al.; Glomectomy for severe bronchial asthma. A double-blind study; Am Rev Respir Dis; 93(1); pp. 84-89; Jan. 1966.

Davidson et al.; Role of the carotid bodies in breath-holding; N Engl J Med; 290(15); pp. 819-822; Apr. 1974.

de Weerd et al.; Prevalence of asymptomatic carotid artery stenosis according to age and sex: Systematic review and metaregression analysis; Stroke; 40(4); pp. 1105-1113; Apr. 2009.

Dickinson et al.; Carotid body tumour: 30 years experience; Br. J. Surg.; 73(1); pp. 14-16; Jan. 1986.

Ding et al.; Role of blood flow in carotid body chemoreflex function in heart failure; J Physiol; 589(1); pp. 245-258; Jan. 2011.

Doumas et al.; Benefits from treatment and control of patients with resistant hypertension; Int. J Hypertension; 8 pgs; Dec. 2011.

Fletcher, Jr. et al.; The surgical treatment of bronchial asthma by excision of the carotid body; J Christ Med Assoc India; 38; pp. 492-496; Sep. 1963.

Gain et al.; Anaesthesia for glomectomy in the asthmatic patient; Can Aneas Soc J; 11(4); pp. 417-424; Jul. 1964.

Giannoni et al.; Combined increased chemosensitiviy to hypoxia and hypercapnia as a prognosticator in heart failure; JACC; 53(21); pp. 1975-1980; May 2009.

Grassi, G.; Renal denervation in cardiometabolic disease: Concepts, achievements and perspectives; Nutr Metab Cardiovasc Dis; 23(2); pp. 77-83; Feb. 2013 (Epub Nov. 10, 2012).

Green, M.; Observations on glomectomized asthmatic patients; Annals of Allergy; 23(5); pp. 213-219; May 1965.

Gudovsky et al.; Surgical treatment of bronchial asthma (with translation); Khirurgiia; 7; pp. 14-18; 2002 (year of pub. sufficiently earlier than effective US filing date and any foreign priority date).

Guz et al.; Peripheral chemoreceptor block in man; Respiration Physiology; 1; pp. 38-40; 1966 (year of pub. sufficiently earlier than effective US filing date and any foreign priority date).

Gwon et al.; Risk factors for stroke during surgery for carotid body tumors; World J Surg; 35(9); pp. 2154-2158; Sep. 2011.

Handelsman, H.; Bilateral carotid body resection as a treatment for chronic intractable bronchospastic diseases; Health Technology Assessment Series: Health Technology Assessment Report; No. 12; 13 pgs.; 1985 (year of pub. sufficiently earlier than effective US filing date and any foreign priority date).

Hickey et al.; Bilateral carotid endarterectomy with attempted preservation of the carotid body function; Ann. Surg.; 175(2); pp. 268-273; Feb. 1972.

(56) References Cited

OTHER PUBLICATIONS

Honda et al.; Hypoxic chemosensitivity in asthmatic patients two decades after carotid body resection; J Appl Physiol.; 46(4); pp. 632-638; Apr. 1979.

Honda, Y.; Respiratory and circulatory activities in carotid body-resected humans; J Appl Physiol; 73(1); pp. 1-8; Jul. 1992.

Karashurov et al.; Radiofrequency electrostimulation of synocarotid for the treatment of bronchial asthma (with translation); Khirurgiia (Mosk); 12; pp. 4-6; 1999 (year of pub. sufficiently earlier than effective US filing date and any foreign priority date).

Keim, W. F.; Carotid glomectomy in bronchial asthma; Archives of Otolaryngology; 79; pp. 225-228; Mar. 1964.

Kim et al.; Carotid artery-hypoglossal nerve relationships in the neck: an anatomical work; Neurol Res; 31; pp. 895-899; Nov. 2009.

Kline et al.; Cervical glomectomy for bronchial asthma; Journal of the Medical Society of New Jersey; 61(5); pp. 176-178; May 1964.

Leggate, J. M.; Treatment of asthma by excision of the carotid body; Postgraduate Med. Journal; 26(292)pp. 71-77; Feb. 1950.

Lesske et al.; Hypertension caused by chronic intermittent hypoxia—influence of chemoreceptors and sympathetic nervous system; J Hypertens; 15(12); pp. 1593-1603; Dec. 1997.

Lo et al.; Anatomical variations of the common carotid artery bifurcation; ANZ J. Surg.; 76(11); pp. 970-72; Nov. 2006.

Lugliani et al.; A role for the carotid body in cardiovascular control in man; Chest; 63(5); pp. 744-750; May 1973.

Lugliani et al.; Effect of bilateral carotid-body resection on ventilatory control at rest and during exercise in man; New England J Med; 285(20); pp. 1105-1111; Nov. 1971.

Lusiani et al.; Prevalence of atherosclerotic involvement of the internal carotid artery in hypertensive patients; Int J Cardiol; 17; pp. 51-56; Oct. 1987.

Lyons et al.; Anatomical variants of the cervical sympathetic chain to be considered during neck dissection; Br J Oral Maxillofac Surg; 36(3); pp. 180-182; Jun. 1998.

Ma et al.; A retrospective study in management of carotid body tumour; Br J Oral Maxillofac Surg; 47(6); pp. 461-465; Sep. 2009.

MacGowan, W.; Removal of the carotid body for asthma: A report of 19 treated patients; Dis Chest; 51(3); pp. 278-281; Mar. 1967.

Marschke et al.; Carotid-body removal in asthma; JAMA; 191(5); p. 397; Feb. 1965.

Marshall, J.; Peripheral chemoreceptors and cardiovascular regulation; Physiological Reviews; 74(3); pp. 543-594; Jul. 1994.

Meyerson, Sheldon; A histological study of the morphology of the cervical carotid bifurcation, including descriptions of intramural neural elements (Thesis); Ohio State University; 47 pgs.; 1968 (year of pub. sufficiently earlier than effective US filing date and any foreign priority date).

Myers et al.; End-tidal CO2 pressure and cardiac performance during exercise in heart failure; Med Sci Sports Exerc; 41(1); pp. 18-24; Jan. 2009.

Nadel et al.; Effect of changes in blood gas tensions and carotid sinus pressure on tracheal volume and total lung resistance to airflow; J Physiol; 163(1); pp. 13-33; Aug. 1962.

Nakayama, K.; Surgical removal of the carotid body for bronchial asthma; Chest; 40(6); pp. 595-604; Dec. 1961.

Nakayama, K.; Surgical removal of the carotid body for bronchial asthma; The Australian and the New Zealand Journal of Surgery; 31(3); pp. 214-221; Feb. 1962.

Nakayama, K.; The surgical significance of the carotid body in relation to bronchial asthma; Thoracic Surgery; Journal of the International College of Surgeons; 39(4); pp. 374-389; Apr. 1963.

Nespoulet et al.; Altitude illness is related to low hypoxic chemoresponse and low oxygenation during sleep; Eur Respir J; 40(3); pp. 673-80; Sep. 2012 (ERJ Express; epub Apr. 20, 2012).

Nguyen et al.; Carotid body detection on CT angiography; Am J Neuroradiol; 32; pp. 1096-1099; Jun.-Jul. 2011.

O'Donnell et al.; Pathophysiology of dyspnea in chronic obstructive pulmonary disease: a rountable; Proc Am Thorac Soc; 4(2); pp. 145-168; May 2007.

O'Rourke et al.; Removal of the carotid body for asthma: A preliminary report of 40 cases; The Medical Journal of Australia; 2; pp. 1040-1043; Dec. 1963.

O'Rourke et al.; Removal of the carotid body for asthma: An appraisal of results; The Medical Journal of Australia; 2; pp. 869-870; Nov. 1964.

Overholt et al.; Hidden or unsuspected brochiectasis in the asthmatic patient; JAMA; 150(5); pp. 438-441; Oct. 1952.

Overholt, R.; Glomectomy for asthma; Chest; 40; pp. 605-610; Dec. 1961.

Paliwoda et al.; Surgical removal of the carotid body and denervation of the carotid sinus for bronchial asthma; East African Medical Journal; 44(7); pp. 285-287; Jul. 1967.

Paton et al.; The carotid body as a therapeutic target for the treatment of sympathetically mediated diseases; Hypertension; 61; pp. 5-13; Jan. 2013.

Perret et al.; High prevalence of peripheral atherosclerosis in a rapidly developing country; Atherosclerosis; 153(1); pp. 9-21; Nov. 2000.

Phillips et al.; Results of glomectomy in chronic obstructive pulmonary disease: A four year follow-up report of 57 cases; Chest; 58(4); pp. 358-362; Oct. 1970.

Phillips, J.; Removal of the carotid body for asthma and emphysema; Southern Medical Journal; 57; pp. 1278-1281; Nov. 1964.

Phillips, J.; Treatment of obstructive bronchial diseases; Geriatrics; 21(7); pp. 137-143; Jul. 1966.

Ponikowski et al.; Peripheral chemoreceptor hypersensitivity; Circulation; 101; pp. 544-549; Jul. 2001.

Rabl et al.; Diagnosis and treatment of carotid body tumors; Thorac Cardiovasc Surg.; 41(6); pp. 340-343; Dec. 1993.

Sanghvi et al.; Carotid body tumors; Journal of Surgical Oncology; 54(3); pp. 190-192; Nov. 1993.

Sedwitz et al.; Should the carotid body be removed in the treatment of asthma and emphysema?; International Surgery; 57(6); pp. 467-469; Jun. 1972.

Sedwitz et al.; Unilateral excision of the carotid body in the treatment of 500 asthma patients; Vascular Diseases; 2; pp. 91-98; Mar. 1965.

Sedwitz, J.; Unilateral carotid body resectin for asthma; Jounal of the National Medical Association; 55(5); pp. 384-388; Sep. 1963.

Segal et al.; Glomectomy in the treatment of chronic bronchial asthma; NEJM; 272(2); pp. 57-63; Jan. 1965.

Segal, M.; Glomectomy for chronic bronchial asthma: A three phase study; Annals of Allergy; 23; pp. 377-384; Aug. 1965.

Severinghaus, J.; Carotid body resection for COPD?; Chest; 95(5); pp. 1128-1129; May 1989.

Shalev, Alon; U.S. Appl. No. 61/178,049 entitled "Endovascular systems for performing interventions during ischemic conditions of the CNS by utilizing the carotid baroreceptors and chemoreceptors and methods for using same," filed May 14, 2009.

Shamblin et al.; Carotid Body Tumor; Am J Surg; 122; pp. 732-739; Dec. 1971.

Shek, J.; Excision of carotid body for advanced emphysema; Michigan State Medical Society Journal; 63; pp. 211-212; Mar. 1964.

Silva et al.; Welcome the carotid chemoreflex to the 'neural control of the circulation during exercise' club; J Physiol; 590(Pt 12) ; pp. 2835-2836; Jun. 2012.

Somfay et al.; Dose-response effect of oxygen on hyperinflation and exercise endurance in non-hypoxaemic COPD patients; European Respiratory Journal 18; pp. 77-84; Jul. 2001.

Somfay et al.; Effect of hyperoxia on gas exchange and lactate kinetics following exercise on set in nonhypoxemic COPD patients; Chest; 121(2); pp. 393-400; Feb. 2002.

Stickland et al.; Distribution during exercise in health and chronic heart failure; Circ Res; 100; pp. 1371-1378; May 2007.

Streian et al.; Glomectomy in carotid sinus syncope and associated arrythmias: Symptomatic bradycardia, atrial flutter and atrial fibrillation; Rom J Intern Med; 44(2); pp. 153-163; 2006 (year of pub. sufficiently earlier than effective US filing date and any foreign priority date).

Streian et al.; Glomectomy in carotid sinus syncope; Rev. Roum. Med.—Med. Int.; 26(1); pp. 47-52; Jan.-Mar. 1988.

(56) References Cited

OTHER PUBLICATIONS

Syed et al.; Percutaneous superficial temporal artery access for carotid artery stenting in patients with a hostile aortic arch; J Endovasc Ther; 18(5); pp. 729-733; Oct. 2011.

Tamura et al.; A morphometric study of the carotid sinus nerve in patients with diabetes mellitus and chronic alchoholism; Journal of the Autonomic Nervous System; 23; pp. 9-15; Jun. 1988.

Tchibukmacher, N.; Surgical anatomy of carotid sinus nerve and intercarotid ganglion; Surgery, Gynecology and Obstetrics; 67; pp. 740-745; 1938 (year of pub. sufficiently earlier than effective US filing date and any foreign priority date).

Timmers et al.; Denervation of carotid baro- and chemoreceptors in humans; J Physiol; 553(1); pp. 3-11; Nov. 2003.

Toorop et al.; Anatomy of the carotid sinus nerve and surgical implications in carotid sinus syndrome; J Vasc Surg; 50; pp. 177-182; Jul. 2009.

Toorop et al.; Effective surgical treatment of the carotid sinus syndrome; J Cardiovasc Surg.; 50; pp. 683-686; Oct. 2009.

Tubbs et al.; Anatomic landmarks for nerves of the neck: a vade mecum for neurosurgeons; Operative Neurosurgery; 56(ONS Suppl 2); pp. ONS256-ONS260; Apr. 2005.

Van Der Mey et al.; Management of carotid body tumors; Otolaryngol Clin North Am.; 34(5); pp. 907-924; Oct. 2001.

Vermeire et al.; Carotid body resection in patients with severe chronic airflow limitation; Bull Eur Physiopathol Respir; 23 Suppl 11; pp. 165s-166s; Aug. 1987.

Ward et al.; Embolization: An adjunctive measure for removal of carotid body tumors; Laryngoscope; 98; pp. 1287-1291; Dec. 1988.

Wasserman et al.; Effect of carotid body resection on ventilatory and acid-base control during exercise; Journal of Applied Physiology; 39(3); pp. 354-358; Aug. 1975.

Wasserman et al.; Ventilation during exercise in chronic heart failure; Basic Res Cardiol; 91(suppl. 1); pp. 1-11; 1996 (year of pub. sufficiently earlier than effective US filing date and any foreign priority date).

Whipp et al.; Physiologic changes following bilateral carotid-body resection in patients with chronic obstructive pulmonary disease; Chest; 101(3); pp. 656-661; Mar. 1992.

Whipp, B.J.; Carotid bodies and breathing in humans; Thorax; 49(11); pp. 1081-1084; Nov. 1994.

Williams et al.; Carotid body tumor; Arch Surg.; 127; pp. 963-968; Aug. 1992.

Winter et al.; Immediate effects of bilateral carotid body resection on total respiratory resistance and compliance in humans; Adv Exp Med Biol; 551; pp. 15-21; 2005 (year of pub. sufficiently earlier than effective US filing date and any foreign priority date).

Winter, B.; Bilateral carotid body resection for asthma and emphysema; International Surgery; 57(6); pp. 458-466; Jun. 1972.

Winter, B.; Carotid body resection in chronic obstructive pulmonary disease; Chest; 100(3); p. 883; Sep. 1991.

Winter, B.; Carotid body resection: Controversy—confusion—conflict; Ann thorac Surg.; 16(6); pp. 648-659; Dec. 1973.

Wood et al.; Bilateral removal of carotid bodies for asthma; thorax; 20(6); pp. 570-573; Nov. 1965.

Gelfand et al.; U.S. Appl. No. 13/852,895 entitled "Carotid Body Modulation Planning and Assessment," filed Mar. 28, 2013.

Gelfand et al.; U.S. Appl. No. 13/869,765 entitled "Endovascular Catheters and Methods for Carotid Body Ablation," filed Apr. 24, 2013.

Gelfand et al.; U.S. Appl. No. 13/933,023 entitled "Carotid Body Ablation Via Directed Energy," filed Jul. 1, 2013.

Engelman et al.; U.S. Appl. No. 13/936,121 entitled "Devices and Systems for Carotid Body Ablation," filed Jul. 5, 2013.

Leung et al.; U.S. Appl. No. 13/908,853 entitled "Methods and Devices for Cryogenic Carotid Body Ablation," filed Jun. 3, 2013.

Giannoni et al.; Clinical significance of chemosensitivity in chronic heart failure: influence on neurohormonal derangement, cheyne-strokes respiration and arrhythmias; Clinical Science (London); 114(7); pp. 489-497; Apr. 2008.

Pennes; Analysis of tissue and arterial blood temperatures in the resting human forearm; J. Appl. Physiol.; 1(2); pp. 93-122; Aug. 1948.

Holton et al.; The effects of bilateral removal of the carotid bodies and denervation of the carotid sinuses in two human subjects; J. Physiol.; 181(2); pp. 365-378; Nov. 1965.

Petersen et al.; Lesion dimensions during temperature-controlled radiofrequency catheter ablation of left ventricular porcine myocardium impact of ablation site; electrode size, and convective cooling; Circulation; 99(2); pp. 319-325; Jan. 1999.

Sapareto et al.; Thermal dose determination in cancer therapy; Int. J. Radiat. Biol. Phys.; 10(6); pp. 787-800; Jun. 1984.

Sehirli et al.; The diameters of common carotid artery and its branches in newborns; Surg. Radiol. Anat.; 27(4); pp. 292-296; Nov. 2005.

Wittkampf et al.; Control of radiofrequency lesion size by power regulation; Circulation; 80(4); pp. 962-968; Oct. 1989.

Lennox et al.; U.S. Appl. No. 14/769,515 entitled "Endovascular catheters for carotid body ablation utilizing an ionic lquid stream," filed Aug. 21, 2015.

Khan et al.; Anatomical variations in human carotid bodies; J. Clin. Pathol.; 41(11); pp. 1196-1199; Nov. 1988.

\* cited by examiner

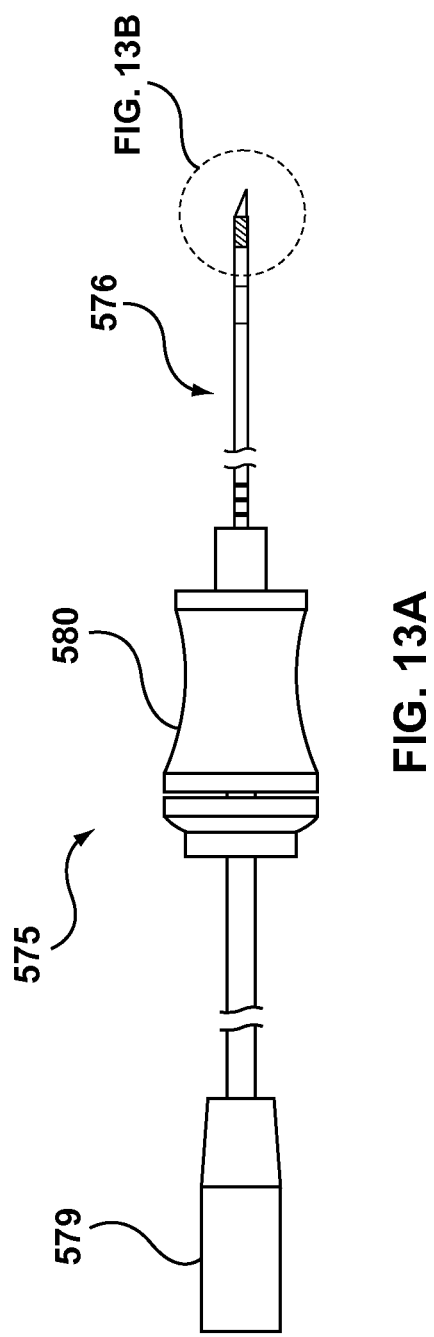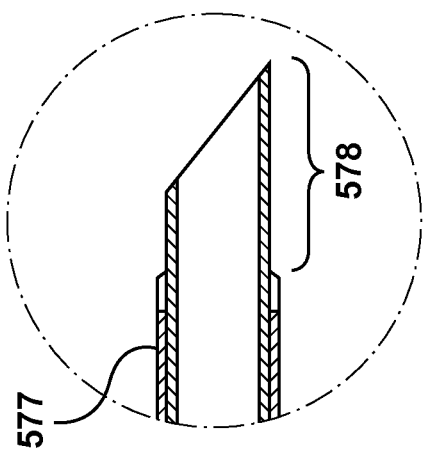
FIG. 13A
FIG. 13B

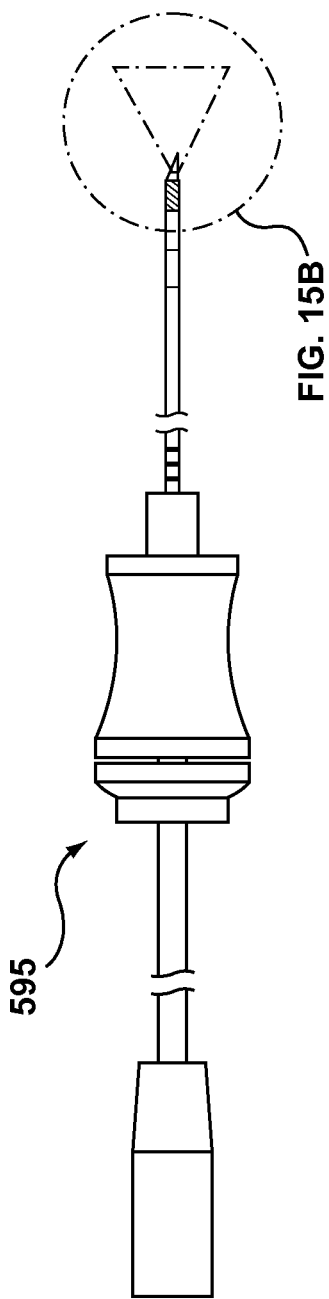
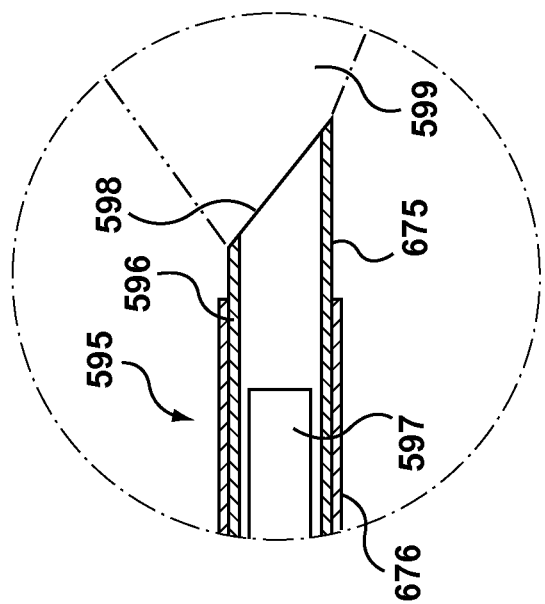

PERCUTANEOUS METHODS AND DEVICES FOR CAROTID BODY ABLATION

CROSS REFERENCE TO RELATED APPLICATIONS

This application claims priority to the following Applications, the disclosures of which are incorporated by reference herein: U.S. Prov. App. No. 61/654,221, filed Jun. 1, 2012; and U.S. Prov. App. No. 61/666,384, filed Jun. 29, 2012.

This application is related to the following applications, the disclosures of which are incorporated by reference herein: U.S. application Ser. No. 13/852,895, filed Mar. 28, 2013; U.S. application Ser. No. 13/869,765, filed Apr. 24, 2013 and U.S. application Ser. No. 13/908,853, filed Jun. 3, 2013.

INCORPORATION BY REFERENCE

All publications and patent applications mentioned in this specification are herein incorporated by reference to the same extent as if each individual publication or patent application was specifically and individually indicated to be incorporated by reference.

TECHNICAL FIELD

The present disclosure is directed generally to systems and methods for treating patients having sympathetically mediated disease associated at least in part with augmented peripheral chemoreflex, heightened sympathetic activation, or autonomic imbalance by ablating at least one peripheral chemoreceptor (e.g., carotid body) with a percutaneous approach.

BACKGROUND

It is known that an imbalance of the autonomic nervous system is associated with several disease states. Restoration of autonomic balance has been a target of several medical treatments including modalities such as pharmacological, device-based, and electrical stimulation. For example, beta blockers are a class of drugs used to reduce sympathetic activity to treat cardiac arrhythmias and hypertension; Gelfand and Levin (U.S. Pat. No. 7,162,303) describe a device-based treatment used to decrease renal sympathetic activity to treat heart failure, hypertension, and renal failure; Yun and Yuarn-Bor (U.S. Pat. No. 7,149,574; U.S. Pat. No. 7,363,076; U.S. Pat. No. 7,738,952) describe a method of restoring autonomic balance by increasing parasympathetic activity to treat disease associated with parasympathetic attrition; Kieval, Burns and Serdar (U.S. Pat. No. 8,060,206) describe an electrical pulse generator that stimulates a baroreceptor, increasing parasympathetic activity, in response to high blood pressure; Hlavka and Elliott (US 2010/0070004) describe an implantable electrical stimulator in communication with an afferent neural pathway of a carotid body chemoreceptor to control dyspnea via electrical neuromodulation. More recently, Carotid Body Ablation (CBA) has been conceived for treating sympathetically mediated diseases.

SUMMARY

A method, device, and system have been conceived for percutaneous carotid body ablation. Percutaneous carotid body ablation generally refers to delivering a device through a patient's skin and tissue proximate to a target ablation site (e.g., peripheral chemosensor, carotid body, or an associated nerve or nerve plexus) of the patient and placing an ablation element associated with the device proximal to the target ablation site and activating the ablation element to ablate the target ablation site.

A carotid body may be ablated by placing an ablation element within an intercarotid septum containing at least a portion of a carotid body or carotid body nerves, then activating the ablation element causing a change in the temperature of the target ablation site to an extent and duration sufficient to ablate tissue in the target ablation site while preserving organs outside of the septum that are not targeted for ablation.

In another exemplary procedure a location of periarterial space associated with a carotid body is identified, then an ablation element is placed proximate to the identified location, then ablation parameters are selected and the ablation element is activated thereby ablating the carotid body, whereby the position of the ablation element and the selection of ablation parameters provides for ablation of the carotid body without substantial collateral damage to non-target nerves.

In a further example the location of space associated with a carotid body is identified (e.g., an intercarotid septum), as well as the location of vital structures not associated with the carotid body, then an ablation element is percutaneously placed proximate to the identified location, ablation parameters are selected and the ablation element is then activated thereby ablating the carotid body, whereby the position of the ablation element and the selection of ablation parameters provides for ablation of the target carotid body without substantial collateral damage to vital structures in the vicinity of the carotid body.

Selectable carotid body ablation parameters include ablation element temperature, duration of ablation element activation, ablation power, ablation element size, ablation modality, and ablation element position relative to a target ablation site.

A location of perivascular space such as an intercarotid septum associated with a carotid body is determined by means of a non-fluoroscopic imaging procedure prior to carotid body ablation, where the non-fluoroscopic location information is translated to a coordinate system based on fluoroscopically identifiable anatomical landmarks or placed fiducial markers.

A function of a carotid body is stimulated and at least one physiological parameter is recorded prior to and during the stimulation, then the carotid body is ablated, and the stimulation is repeated, whereby the change in recorded physiological parameter(s) prior to and after ablation is an indication of the effectiveness of the ablation.

A function of a carotid body is temporarily blocked and at least one physiological parameter(s) is recorded prior to and during the blockade, then the carotid body is ablated, and the blockade is repeated, whereby the change in recorded physiological parameter(s) prior to and after ablation is an indication of the effectiveness of the ablation.

A method has been conceived in which interstitial space associated with a carotid body is identified, then an ablation element is placed in a predetermined location proximate to the identified location, then ablation parameters are selected and the ablation element is activated and then deactivated, the ablation element is then repositioned in at least one additional predetermined location and the ablation element is then reactivated using the same or different ablation parameters, whereby the positions of the ablation element and the selection of ablation parameters provides for ablation of the carotid body without substantial collateral damage to adjacent functional structures.

A method has been conceived by which interstitial space associated with a carotid body is identified, an ablation element configured for tissue freezing is placed proximate to the identified location, ablation parameters are selected for reversible cryo-ablation and the ablation element is activated, the effectiveness of the ablation is then determined by at least one physiological response to the ablation, and if the determination is that the physiological response is favorable, then the ablation element is reactivated using the ablation parameters selected for permanent carotid body ablation.

A method has been conceived by which an ablation element on an device is percutaneously positioned at a target ablation site (e.g., proximate a carotid body or carotid body nerves), an ablation protection element is deployed from the device distal to the ablation element to protect tissue distal to the protection element from ablation, ablation energy is delivered from the ablation element to the target site.

A system has been conceived comprising a percutaneous ablation device configured with an ablation element in a vicinity of a distal end, and a connection between the ablation element and a source of ablation energy at a proximal end, whereby the distal end of the ablation device is constructed to be inserted through skin and soft tissue of a patient using fluoroscopic or sonography guidance techniques.

A system has been conceived comprising a percutaneous ablation device configured with an ablation element in a vicinity of a distal end configured for carotid body ablation and further configured for at least one of the following: neural stimulation, neural blockade, carotid body stimulation, or carotid body blockade; and a connection between the ablation element and a source of ablation energy, stimulation energy and/or blockade energy.

A system has been conceived comprising a percutaneous ablation device configured with an ablation element and at least one electrode configured for at least one of the following: neural stimulation, neural blockade, carotid body stimulation and carotid body blockade; and a connection between the ablation element to a source of ablation energy, and a connection between the ablation element and/or electrode(s) to a source of stimulation energy and/or blockade energy.

A system has been conceived comprising a percutaneous ablation device with an ablation element mounted in a vicinity of a distal end configured for tissue heating, whereby, the ablation element comprises at least one electrode and at least one temperature sensor, a connection between the ablation element electrode(s) and temperature sensor(s) to an ablation energy source, with the ablation energy source being configured to maintain the ablation element at a temperature in the range of 40 to 100 degrees centigrade during ablation using signals received from the temperature sensor(s).

A system has been conceived comprising a percutaneous ablation device with an ablation element mounted in a vicinity of a distal end configured for tissue heating, whereby, the ablation element comprises at least one electrode and at least one temperature sensor and at least one irrigation channel, and a connection between the ablation element electrode(s) and temperature sensor(s) and irrigation channel(s) to an ablation energy source, with the ablation energy source being configured to maintain the ablation element at a temperature in the range of 20 to 100 degrees centigrade during ablation using signals received from the temperature sensor(s) and by providing irrigation to the vicinity of the ablation element.

A system has been conceived comprising a percutaneous ablation device with an ablation element mounted in a vicinity of a distal end configured for tissue freezing, whereby, the ablation element comprises at least one cryogenic expansion chamber and at least one temperature sensor, and a connection between the ablation element expansion chamber and temperature sensor(s) to a cryogenic agent source, with the cryogenic agent source being configured to maintain the ablation element at a predetermined temperature in the range of −20 to −160 degrees centigrade during ablation using signals received from the temperature sensor(s).

A system has been conceived comprising a percutaneous ablation device with an ablation element mounted in a vicinity of a distal end configured to freeze tissue, and to heat tissue, whereby, the ablation element comprises at least one cryogenic expansion chamber constructed of an electrically conductive material and configured as an electrode, and at least one temperature sensor, and a connection between the ablation element expansion chamber/electrode and temperature sensor(s) to an ablation source consisting of cryogenic agent source and an electrical heating energy source.

A procedural kit for percutaneous ablation of a carotid body has been conceived comprising a cannula and trocar set, and a percutaneous ablation device configured to be inserted through the cannula comprising an ablation element mounted in vicinity of a distal end.

A procedural kit for percutaneous ablation of a carotid body has been conceived comprising a dilation set, a percutaneous ablation device configured to be inserted through a dilator of the dilation set comprising an ablation element mounted in vicinity of a distal end.

A method has been conceived to reduce or inhibit chemoreflex function generated by a carotid body in a mammalian patient, to reduce afferent nerve sympathetic activity of carotid body nerves to treat a sympathetically mediated disease, the method comprising: percutaneously positioning an ablation device proximate an intercarotid septum of the patient such that a distal section of the ablation device is proximate to the carotid body of the patient; supplying energy to the ablation element wherein the energy is supplied by an energy supply apparatus outside of the patient; applying the energy from the energy supply to the ablation element to ablate tissue proximate to or included in the carotid body; and removing the ablation device from the patient; wherein a carotid body chemoreflex function is inhibited or autonomic balance is restored due to the ablation.

A method has been conceived to treat a patient having a sympathetically mediated disease by reducing or inhibiting chemoreflex function generated by a carotid body including steps of percutaneously inserting an ablation device into the patient's intercarotid septum, positioning a portion of the ablation device proximate a carotid body (e.g., in a carotid artery), applying ablative energy to the target ablation site via the ablation element, and removing the catheter from the patient.

The methods and systems disclosed herein may be applied to satisfy clinical needs related to treating cardiac, metabolic, and pulmonary diseases associated, at least in part, with enhanced chemoreflex (e.g., high chemosensor sensitivity or high chemosensor activity) and related sympathetic activation. The treatments disclosed herein may be used to restore autonomic balance by reducing sympathetic activity, as opposed to increasing parasympathetic activity. It is understood that parasympathetic activity can increase as a result of the reduction of sympathetic activity (e.g., sympathetic withdrawal) and normalization of autonomic balance. Furthermore, the treatments may be used to reduce sympathetic activity by modulating a peripheral chemoreflex. Furthermore, the treatments may be used to reduce afferent neural stimulus, conducted via afferent carotid body nerves, from a carotid body to the central nervous system. Enhanced peripheral and central chemoreflex is implicated in several pathologies including hypertension, cardiac tachyarrhythmias, sleep apnea, dyspnea, chronic obstructive pulmonary disease (COPD), diabetes and insulin resistance, and CHF. Mechanisms by which these diseases progress may be different, but they can commonly include contribution from increased afferent neural signals from a carotid body. Central sympathetic nervous system activation is common to all these progressive and debilitating diseases. Peripheral chemoreflex may be modulated, for example, by modulating carotid body activity. The carotid body is the sensing element of the afferent limb of the peripheral chemoreflex. Carotid body activity may be modulated, for example, by ablating a carotid body or afferent nerves emerging from the carotid body. Such nerves can be found in a carotid body itself, in a carotid plexus, in an intercarotid septum, in periarterial space of a carotid bifurcation and internal and external carotid arteries, and internal jugular vein. Therefore, a therapeutic method has been conceived that comprises a goal of restoring or partially restoring autonomic balance by reducing or removing carotid body input into the central nervous system.

BRIEF DESCRIPTION OF THE DRAWINGS

FIGS. 13A and 13B are schematic illustrations of a percutaneous radiofrequency ablation probe.

FIGS. 15A and 15B are schematic illustrations of a percutaneous forward-firing laser ablation probe.

DETAILED DESCRIPTION

Figure 1:
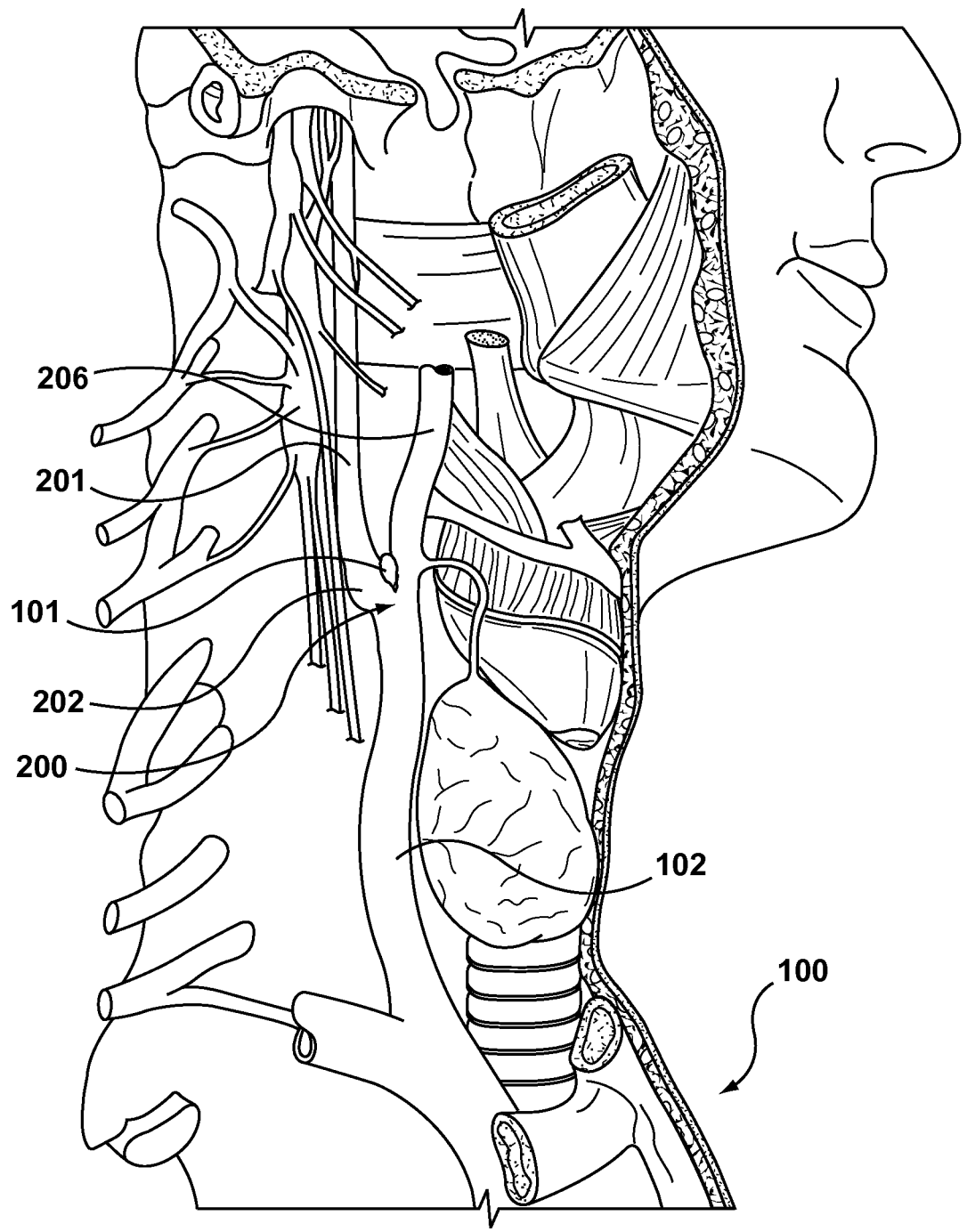
FIG. 1 is a cutaway illustration of vasculature and neural structures of a right side of a patient's neck.

Systems, devices, and methods have been conceived to ablate fully or partially one or both carotid bodies or carotid body nerves via percutaneous access to treat patients having a sympathetically mediated disease (e.g., cardiac, renal, metabolic, or pulmonary disease such as hypertension, CHF, or sleep apnea, sleep disordered breathing, diabetes or insulin resistance) at least partially resulting from augmented peripheral chemoreflex (e.g., peripheral chemoreceptor hypersensitivity or hyperactivity) or heightened sympathetic activation. A reduction of peripheral chemoreflex (e.g., chemosensitivity or afferent nerve hyperactivity) or reduction of afferent nerve signaling from a carotid body (CB) resulting in a reduction of central sympathetic tone is one possible therapy pathway. Higher than normal chronic or intermittent activity of afferent carotid body nerves is considered enhanced chemoreflex for the purpose of this application regardless of its cause. Other important benefits such as increase of parasympathetic tone, vagal tone and specifically baroreflex and baroreceptor activity reduction of dyspnea, hyperventilation and breathing rate may be expected in some patients. Secondary to reduction of breathing rate additional increase of parasympathetic tone can be expected in some cases. Augmented peripheral chemoreflex (e.g., carotid body activation) leads to increases in sympathetic nervous system activity, which is in turn primarily responsible for the progression of chronic disease as well as debilitating symptoms and adverse events seen in our intended patient populations. The patients are mammalian patients, including humans. Carotid bodies contain cells that are sensitive to oxygen and carbon dioxide. Carotid bodies also respond to blood flow, pH acidity, glucose level in blood and possibly other variables. Thus carotid body ablation may be a treatment for some patients, for example having hypertension, drug resistant hypertension, heart disease or diabetes, even if chemosensitive cells are not activated.

Percutaneous carotid body ablation may involve inserting a probe equipped with ablation element that can be an energy delivery element in the distal region via needle puncture in a patient's skin, positioning a distal region of the probe proximate a carotid body (e.g., at a carotid bifurcation, inside an intercarotid septum) proximate carotid body nerve (e.g., carotid sinus nerve, carotid plexus), positioning an ablation element proximate to a target site (e.g., a carotid body, an afferent nerve associated with a carotid body, a peripheral chemosensor, an intercarotid septum), and delivering an ablation agent from the ablation element to ablate the target site. Other methods and devices for chemoreceptor ablation are described.

Targets:

To inhibit or suppress a peripheral chemoreflex, anatomical targets for ablation (also referred to as targeted tissue, target ablation sites, or target sites) may include at least a portion of at least one carotid body, nerves associated with a peripheral chemoreceptor (e.g., carotid body nerves, carotid sinus nerve, carotid plexus), small blood vessels feeding a peripheral chemoreceptor, carotid body parenchyma, chemosensitive cells (e.g., glomus cells), tissue in a location where a carotid body is suspected to reside (e.g., a location based on pre-operative imaging or anatomical likelihood), an intercarotid septum, a substantial part of an intercarotid septum or a combination thereof.

Shown in FIG. 1, a carotid body (CB) 101 modulates sympathetic tone through direct signaling to the central nervous system. Carotid bodies represent a paired organ system located at a bifurcation 200 of a common carotid artery 102 bilaterally although there is a possibility of existence of humans with only one fully developed or functional carotid body. The common carotid artery 102 bifurcates into an internal carotid artery 201 and an external carotid artery 206. Each 2.5-5 mm ovoid shaped carotid body resembles a grain of rice and is innervated both by the carotid sinus nerve (CSN, a branch of the glossopharyngeal nerve), and the ganglioglomerular (sympathetic) nerve of the nearby superior cervical ganglion. The CB is the most perfused organ per gram of tissue weight in the body and receives blood via one or more arterial branch arising from internal or external carotid artery.

Figure 2:
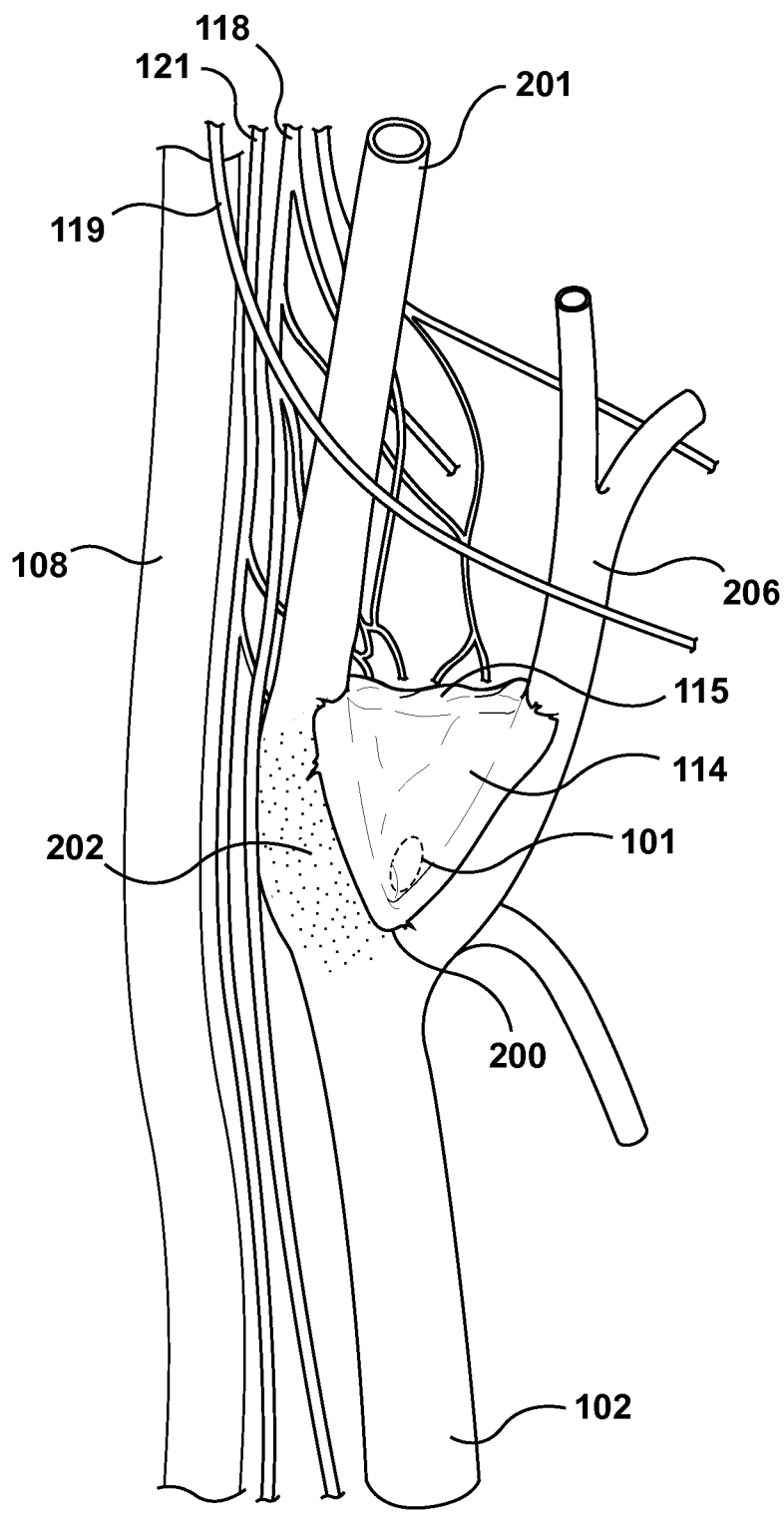
FIG. 2 is an illustration of a target region for carotid body ablation showing a carotid body associated with an intercarotid septum of a carotid bifurcation.
Figure 3:
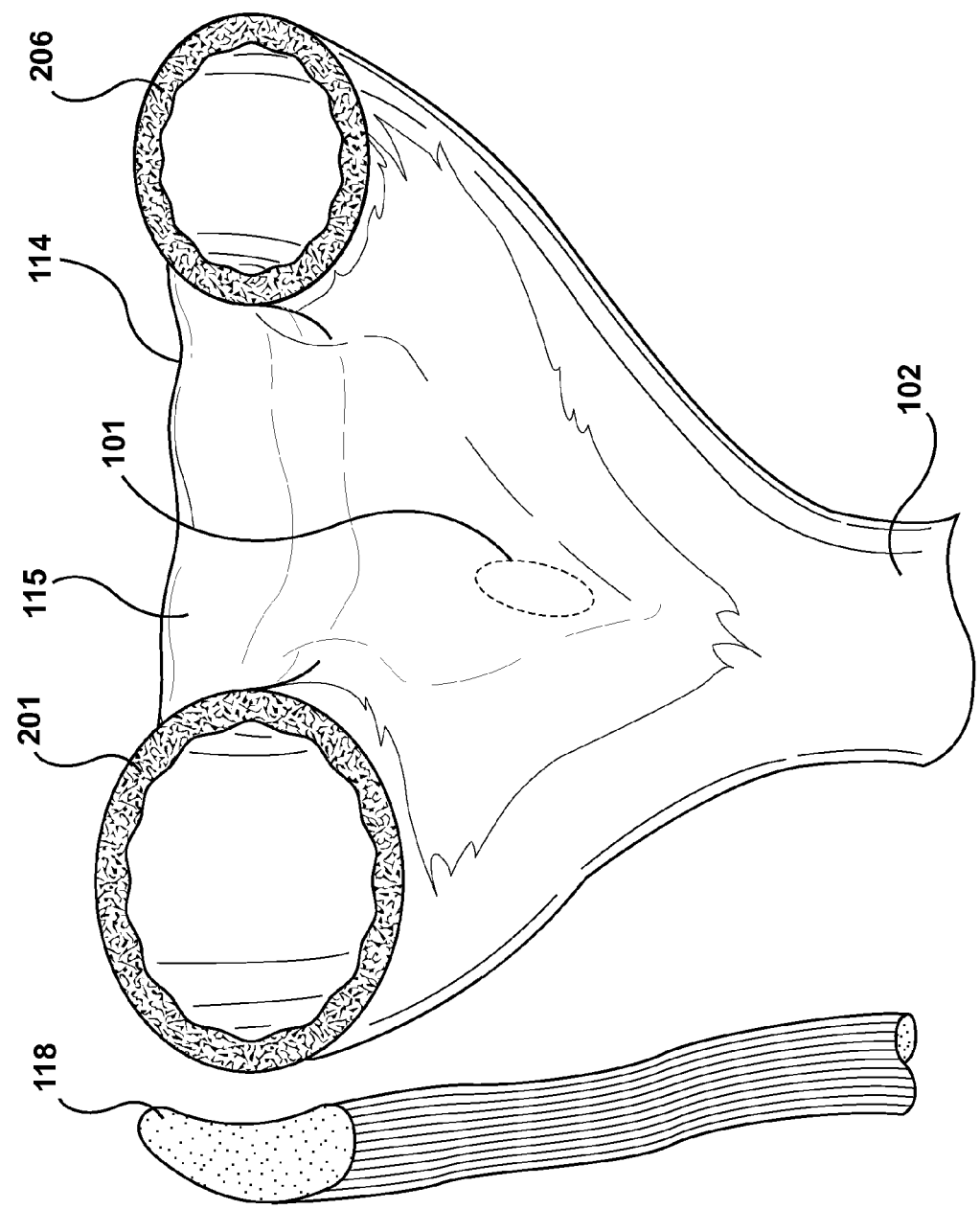
FIG. 3 is an illustration of a target region for carotid body ablation showing a carotid body associated with an intercarotid septum of a carotid bifurcation.
Figure 4:
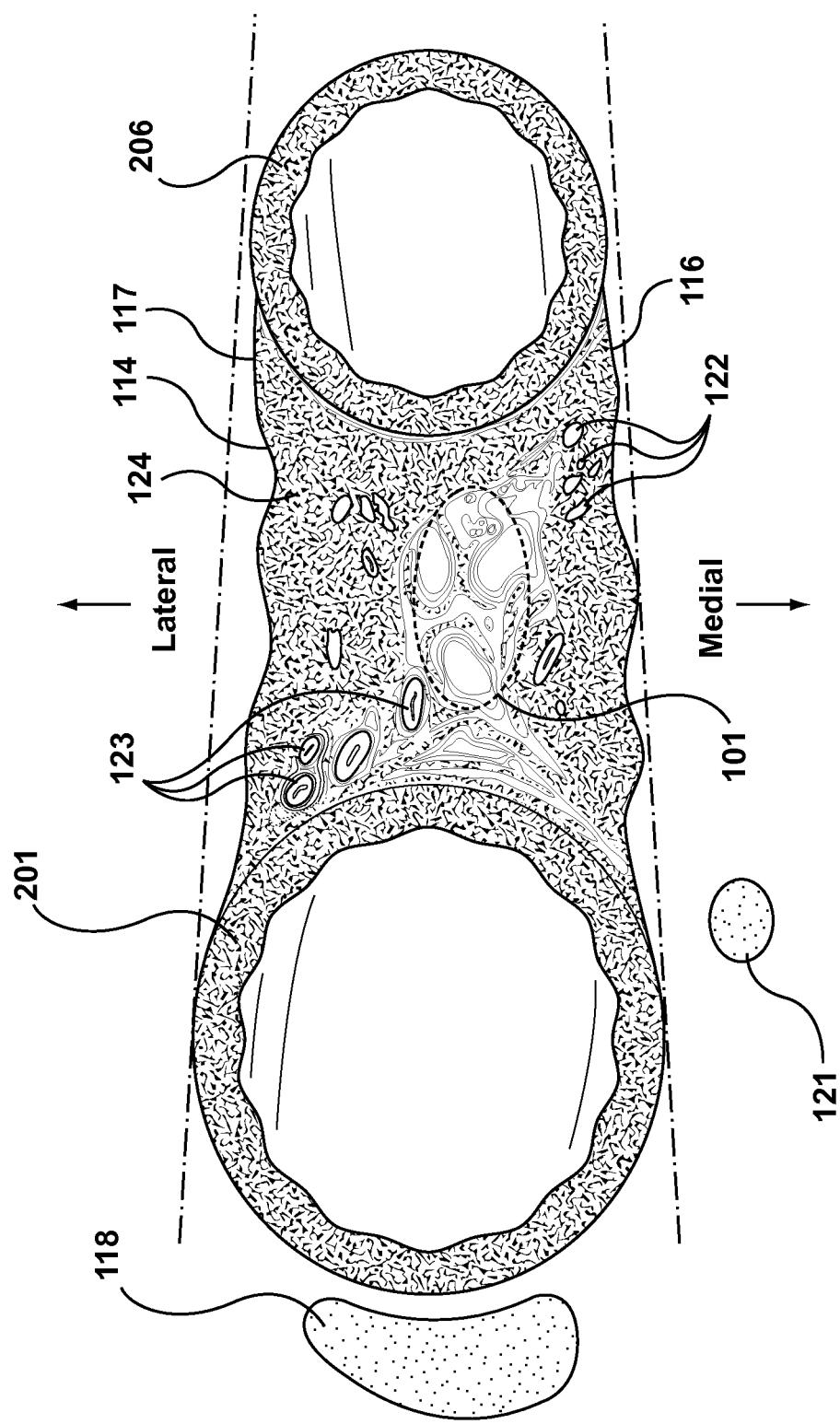
FIG. 4 is an illustration of a cross section of an intercarotid septum.

An intercarotid septum 114 (also referred to as carotid septum) shown in FIGS. 2, 3, and 4 is herein defined as a wedge or triangular segment of tissue with the following boundaries: A saddle of a carotid bifurcation 200 defines a caudal aspect (an apex) of a carotid septum 114; Facing walls of internal 201 and external 206 carotid arteries define two sides of a carotid septum; A cranial boundary 115 of a carotid septum extends between these arteries and may be defined as cranial to a carotid body but caudal to any vital nerve structures (e.g., hypoglossal nerve), for example a cranial boundary may be about 10 mm (possibly 15 mm) from the saddle of the carotid bifurcation; Medial 116 and lateral 117 walls of the carotid septum 114 are generally defined by planes approximately tangent to the internal and external carotid arteries; One of the planes is tangent to the lateral wall of the internal and external carotid arteries and the other plane is tangent to the medial walls of these arteries. An intercarotid septum is between medial and lateral walls. An intercarotid septum 114 may contain a carotid body 101 and may be absent of important non-target structures such as a vagus nerve 118 or important sympathetic nerves that are part of sympathetic chain system 121 or a hypoglossal nerve 119. An intercarotid septum may include some baroreceptors 202 or baroreceptor nerves. An intercarotid septum may also include small blood vessels 123 and fat 124.

Carotid body nerves are anatomically defined herein as carotid plexus nerves 122 or carotid sinus nerves. Carotid body nerves are functionally defined herein as afferent nerves and nerve fibers that conduct information from a carotid body to a central nervous system.

An ablation may be focused exclusively on targeted tissue, or be focused on the targeted tissue while safely ablating tissue proximate to the targeted tissue (e.g., to ensure the targeted tissue is ablated or as an approach to gain access to the targeted tissue). An ablation may be as big as the carotid body itself, somewhat smaller, or bigger and can include tissue surrounding the carotid body such as blood vessels, fat, adventitia, fascia, small blood vessels perfusing the carotid body, or nerves connected to and innervating the chemosensitive (glomus) cells of the carotid body. An intercarotid plexus 122 or carotid sinus nerve may be a target of ablation with an understanding that some baroreceptor nerves will be ablated together with carotid body nerves. Baroreceptors are distributed in the human arteries and have high degree of redundancy thus some loss of baroreceptors and baroreceptor nerves can be tolerated for the purpose and in the process of carotid body ablation therapy.

Tissue may be ablated to inhibit or suppress a chemoreflex of only one of a patient's two carotid bodies. Another embodiment involves ablating tissue to inhibit or suppress a chemoreflex of both of a patient's carotid bodies. For example a therapeutic method may include ablation of one carotid body, measurement of resulting chemosensitivity, sympathetic activity, respiration or other parameter related to carotid body hyperactivity and ablation of the second carotid body if needed to further reduce chemosensitivity following unilateral ablation.

An embodiment of a therapy may substantially reduce chemoreflex without excessively reducing the baroreflex of the patient. The proposed ablation procedure may be targeted to substantially spare the carotid sinus, baroreceptors distributed in the walls of carotid arteries (specifically internal carotid artery), and at least some of the carotid sinus nerves that conduct signals from said baroreceptors. For example, the baroreflex may be substantially spared by targeting a limited volume of ablated tissue possibly enclosing the carotid body, tissues containing a substantial number of carotid body nerves, tissues located in periadventitial space of a carotid bifurcation, tissue located at the attachment of a carotid body to an artery. Said targeted ablation may be enabled by visualization of the area or carotid body itself, for example by CT, CT angiography, MRI, ultrasound sonography, Doppler flow sonography, fluoroscopy, blood flow visualization, or injection of contrast, and positioning of an instrument in the carotid body or in close proximity while avoiding excessive damage (e.g., perforation, stenosis, thrombosis) to carotid arteries, carotid sinus nerves or other vital nerves such as vagus nerve or sympathetic nerves located primarily outside of the intercarotid septum. Thus imaging a carotid body before ablation may be instrumental in (a) selecting candidates if a carotid body is present, large enough and identified and (b) guiding therapy by providing a landmark map for an operator to guide an ablation instrument to the carotid septum, center of the carotid septum, carotid body nerves, the area of a blood vessel proximate to a carotid body, or to an area where carotid body itself or carotid body nerves may be anticipated. It may also help exclude patients in whom the carotid body is located substantially outside of the carotid septum in a position close to a vagus nerve, hypoglossal nerve, jugular vein or some other structure that can be endangered by ablation. In one embodiment, only patients with a carotid body substantially located within the intercarotid septum are selected for ablation therapy.

Once a carotid body is ablated the carotid body chemoreflex does not substantially return in humans (in humans aortic chemoreceptors are considered undeveloped). To the contrary, once a carotid sinus baroreflex is removed it is generally compensated, after weeks or months, by the aortic or other arterial baroreceptor baroreflex. Thus, if both the carotid chemoreflex and baroreflex are removed or substantially reduced, for example by interruption of the carotid sinus nerve or intercarotid plexus nerves, baroreflex may eventually be restored while the chemoreflex may not. The consequences of temporary removal or reduction of the baroreflex can be in some cases relatively severe and require hospitalization and management with drugs, but they generally are not life threatening, terminal or permanent. Thus, it is understood that while selective removal of carotid body chemoreflex with baroreflex preservation may be desired, it may not be absolutely necessary in some cases.

Ablation:

The term "ablate" may refer to the act of altering a tissue to suppress or inhibit its biological function or ability to respond to stimulation permanently or for an extended period of time (e.g., greater than 3 weeks, greater than 6 months, greater than a year, for several years, or for the remainder of the patient's life). For example, ablation may involve, but is not limited to, thermal necrosis (e.g., using energy such as thermal energy, radiofrequency electrical current, direct current, microwave, ultrasound, high intensity focused and unfocused ultrasound, low frequency ultrasound, and laser), cryogenic ablation, electroporation, selective denervation, embolization (e.g., occlusion of blood vessels feeding the carotid body), artificial sclerosing of blood vessels, mechanical impingement or crushing, surgical removal, chemical ablation, or application of radiation causing controlled necrosis (e.g., brachytherapy, radioisotope therapy). Selective denervation may involve, for example, interruption of afferent nerves from a carotid body while preserving nerves from a carotid sinus, which conduct baroreceptor signals. Another example of selective denervation may involve interruption of a carotid sinus nerve, or intercarotid plexus which is in communication with both a carotid body and some baroreceptors wherein chemoreflex from the carotid body is reduced permanently or for an extended period of time (e.g., years) and baroreflex is substantially restored in a short period of time (e.g., days or weeks). As used herein, the term "ablate" refers to interventions that suppress or inhibit natural chemoreceptor or afferent nerves functioning, which is in contrast to neuromodulating or reversibly deactivating and reactivating chemoreceptor functioning.

Carotid Body Ablation (CBA) herein refers to ablation of a target tissue wherein the desired effect is to reduce or remove the afferent neural signaling from a chemosensor (e.g., carotid body) or reducing a chemoreflex. Chemoreflex or afferent nerve activity cannot be directly measured in a practical way, thus indexes of chemoreflex such as chemosensitivity can sometimes be uses instead. Chemoreflex reduction is generally indicated by a reduction of an increase of ventilation and ventilation effort per unit of blood gas concentration, saturation or partial pressure change or by a reduction of central sympathetic nerve activity that can be measured indirectly. Sympathetic nerve activity can be assessed by measuring activity of peripheral nerves leading to muscles (MSNA), heart rate (HR), heart rate variability (HRV), production of hormones such as renin, epinephrine and angiotensin, and peripheral vascular resistance. All these parameters are measurable and can lead directly to the health improvements. In the case of CHF patients, blood pH, blood $PCO_2$, degree of hyperventilation and metabolic exercise test parameters such as peak $VO_2$, and $VE/VCO_2$ slope are also important. It is believed that patients with heightened chemoreflex have low $VO_2$ and high $VE/VCO_2$ slope (index of respiratory efficiency) as a result of, for example, tachypnea and low blood $CO_2$. These parameters are also related to exercise limitations that further speed up patient's status deterioration towards morbidity and death. It is understood that all these indexes are indirect and imperfect and intended to direct therapy to patients that are most likely to benefit or to acquire an indication of technical success of ablation rather than to prove an exact measurement of effect or guarantee a success.

Carotid body ablation may include methods and systems for the thermal ablation of tissue via thermal heating or cooling mechanisms. Thermal ablation may be achieved due to a direct effect on tissues and structures that are induced by the thermal stress. Additionally or alternatively, the thermal disruption may at least in part be due to alteration of vascular or peri-vascular structures (e.g., arteries, arterioles, capillaries or veins), which perfuse the carotid body and neural fibers surrounding and innervating the carotid body (e.g., nerves that transmit afferent information from carotid body chemoreceptors to the brain). Additionally or alternatively thermal disruption may be due to a healing process, fibrosis, or scarring of tissue following thermal injury, particularly when prevention of regrowth and regeneration of active tissue is desired. As used herein, thermal mechanisms for ablation may include both thermal necrosis or thermal injury or damage (e.g., via sustained heating, convective heating or resistive heating or combination). Thermal heating mechanisms may include raising the temperature of target neural fibers above a desired threshold, for example, above a body temperature of about 37° C. e.g., to achieve thermal injury or damage, or above a temperature of about 45° C. (e.g., above about 60° C.) to achieve thermal necrosis. Thermal-cooling mechanisms for ablation may include reducing the temperature of target neural fibers below a desired threshold (e.g., to achieve freezing thermal injury). It is generally accepted that temperatures below −40° C. applied over a minute or two results in irreversible necrosis of tissue and scar formation. It is recognized that tissue ablation by cold involves mechanisms of necrosis and apoptosis. At a low cooling rate freeze, tissue is destroyed by cellular dehydration and at high cooling rate freeze by intracellular ice formation and lethal rupture of plasma membrane.

In addition to raising or lowering temperature during thermal ablation, a length of exposure to thermal stimuli may be specified to affect an extent or degree of efficacy of the thermal ablation. For example, the length of exposure to thermal stimuli may be for example, longer than or equal to about 30 seconds, or even longer than or equal to about 2 minutes. It may depend on the form of thermal energy used. In the case of high frequency ultrasound time of exposure may be significantly shorter such as 5 sec. Furthermore, the length of exposure can be less than or equal to about 10 minutes, though this should not be construed as the upper limit of the exposure period. A temperature threshold, or thermal dosage, may be determined as a function of the duration of exposure to thermal stimuli. Additionally or alternatively, the length of exposure may be determined as a function of the desired temperature threshold. These and other parameters may be specified or calculated to achieve and control desired thermal ablation.

In some embodiments, thermally-induced ablation of carotid body or carotid body nerves may be achieved via direct application of thermal cooling or heating energy to the target tissue. For example, a chilled or heated fluid can be applied at least proximate to the target, or heated or cooled elements (e.g., thermoelectric element, resistive heating element, cryogenic tip or balloon) can be placed in the vicinity of a carotid body in some embodiments directly into the carotid septum. In other embodiments, thermally-induced ablation may be achieved via indirect generation or application of thermal energy to the target neural fibers, such as through application of an electric field (e.g., radiofrequency, alternating current, and direct current), high-intensity focused ultrasound (HIFU), low frequency ultrasound, laser irradiation, or microwave radiation, to the target neural fibers. For example, thermally induced ablation may be achieved via delivery of a pulsed or continuous thermal electric field to the target tissue such as RF and pulsed RF, the electric field being of sufficient magnitude or duration to thermally induce ablation of the target tissue (e.g., to heat or thermally ablate or cause necrosis of the targeted tissue). Additional and alternative methods and apparatuses may be utilized to achieve thermally induced ablation, as described hereinafter.

Figure 5:
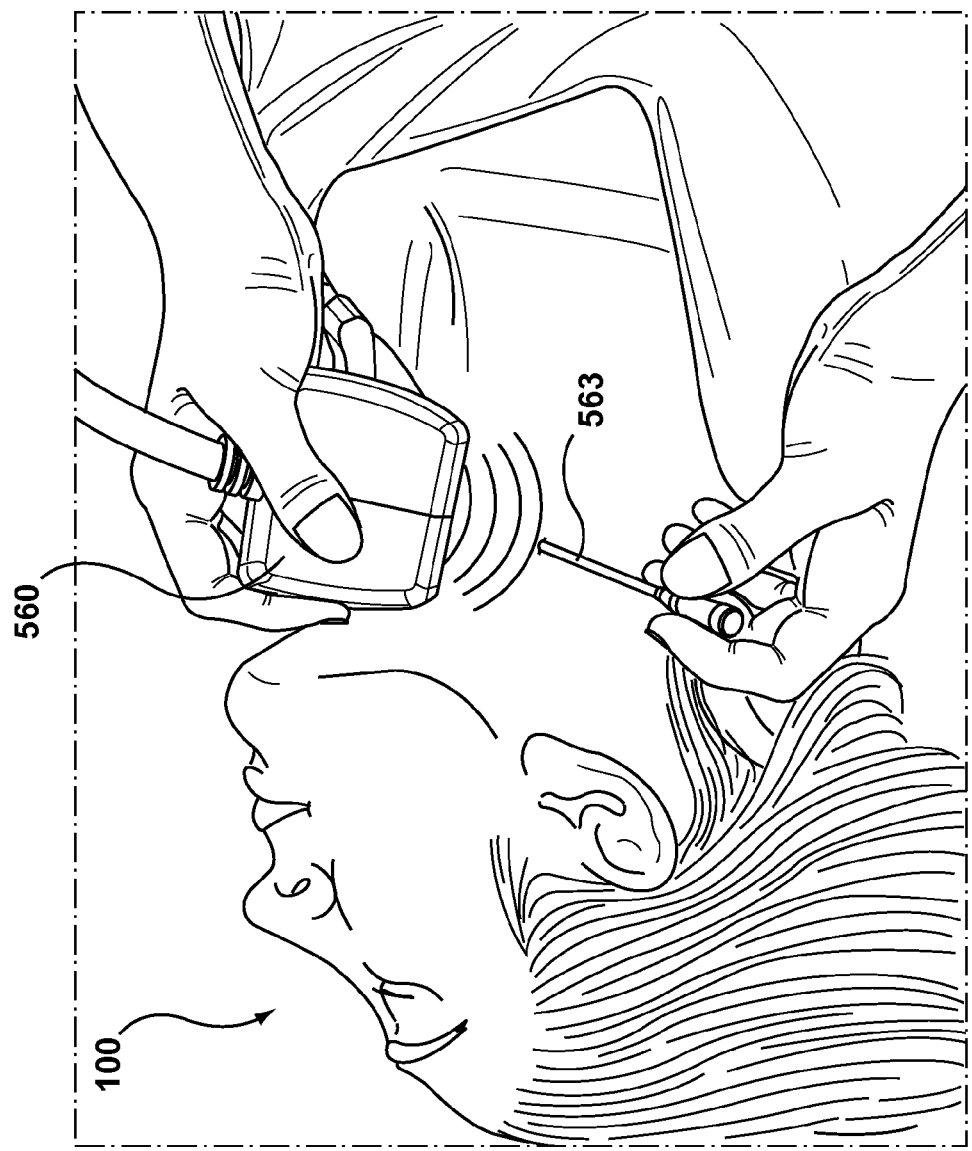
FIG. 5 is an illustration showing a percutaneous access cannula being inserted into the target region for carotid body ablation using ultrasonic imaging guidance.

Percutaneous Access:

A percutaneous ablation device for carotid body ablation may be delivered through a needle puncture or small incision in a patient's skin and directed toward a target ablation site. For example, as shown in FIG. 5 a percutaneous cannula 563 may be advanced through a patient's skin in a region of the patient's neck towards a target ablation site. Delivery of a percutaneous cannula 563 or percutaneous ablation device may be performed under visual guidance such as ultrasound sonography. In FIG. 5 an ultrasound transducer 560 is used to visualize the patient's target ablation site and the percutaneous cannula 563, which may have an echogenic coating to facilitate ultrasound visualization. Delivery of percutaneous cannula can be achieved by hand-eye coordination or assisted by guides or robotic manipulators. Ultrasonic transducer(s) can generate more than one image.

Biplane transducer arrays that are rotated (for example 90 degrees) relative to each other (e.g., form a T shape) are used to allow a doctor to view two image planes at once. The purpose of biplane imaging is to enable a doctor to visualize simultaneously the cannula or ablation probe and the carotid arteries. The imaging plane for visualization of carotid arteries and a jugular vein can include Doppler Imaging modes and pulsed wave Doppler mode. Color Doppler image of blood vessels can enable distinction of veins and arteries and assist navigation of ablation instruments into the carotid septum.

In order to achieve placement in a carotid septum via a percutaneous approach a cannula may need to traverse layers of muscle and some blood vessels, and potentially a jugular vein. Position of the carotid vessels, as well as the jugular vein, may be adjusted by rotation and extension of the neck. The position of the jugular vein in relation to the intercarotid septum may be altered and the displacement of the jugular vein can "open" the view on the intercarotid septum from a lateral side.

The carotid bifurcation is typically located approximately 1-2 cm below the skin at its closest range. Various entry points in the skin and angles of approach from the entry point to a target site may be possible. Percutaneous approaches for carotid body ablation may include: an anterior approach, a posterior-lateral approach, a posterior-medial approach, and a paraspinal approach.

Figure 8:
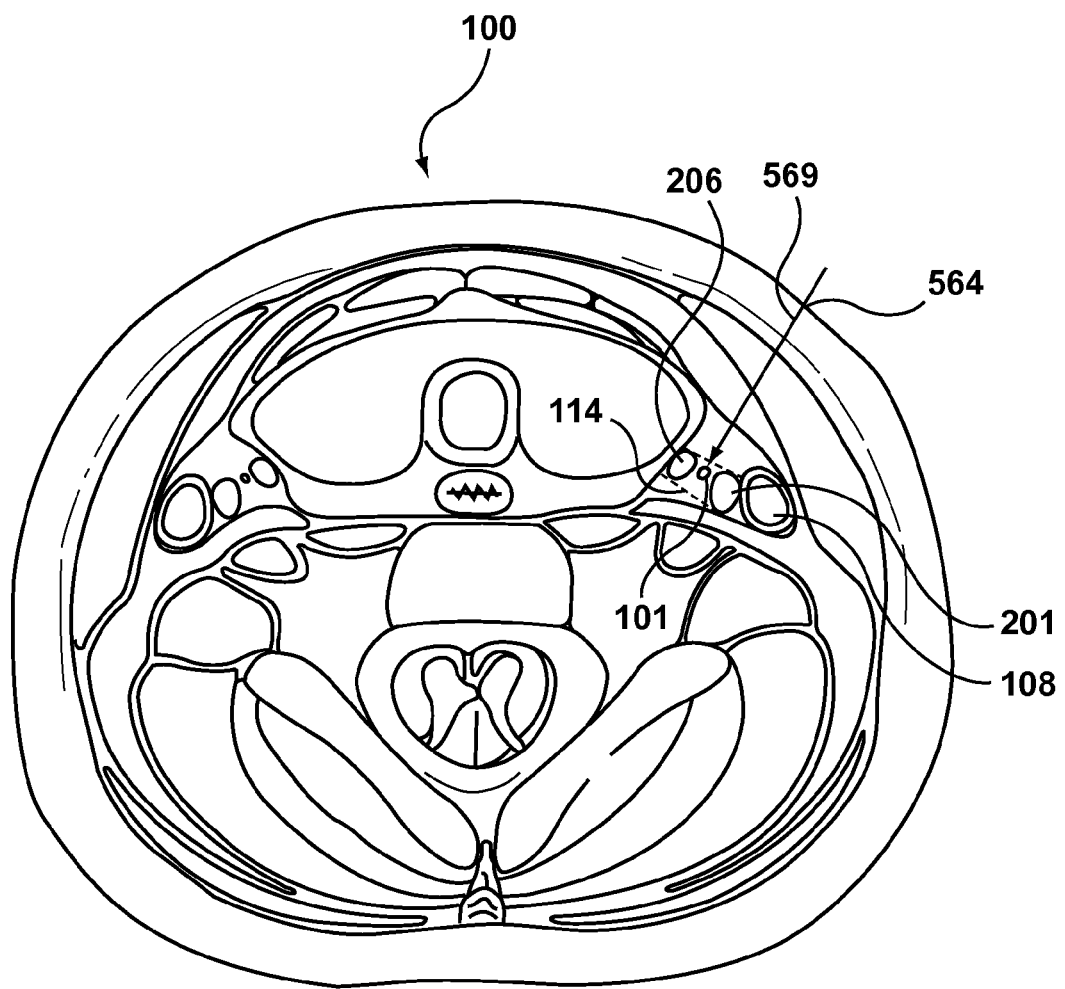
FIG. 8 is an illustration of a cross sectional view of a patient's neck showing an anterior percutaneous approach for ablation of a carotid body.

As shown in FIG. 8, an anterior approach may be chosen to approach a target ablation site, such as an intercarotid septum from a lateral side of the septum. The percutaneous device (e.g., cannula or ablation device) may pass through skin, subcutaneous fat, neck muscles, and, depending on the patient's anatomy and positioning, the jugular vein 108 in order to reach an intercarotid septum 114 from a lateral side 117 (see FIG. 4). An anterior approach may comprise inserting a device anteriorly of the sternocleidomastoid muscle. Using two fingers, the sternocleidomastoid muscle may be retracted laterally, which may pull the internal carotid artery and internal jugular vein away from the insertion site 564. The device may pass along a projection 569 approximately perpendicular to the skin and through tissue into the intercarotid septum, intermediate of the internal and external carotid arteries. The anterior approach may be chosen to approach lateral or medial aspects of the intercarotid septum. Depth varies from person to person.

Figure 9A:
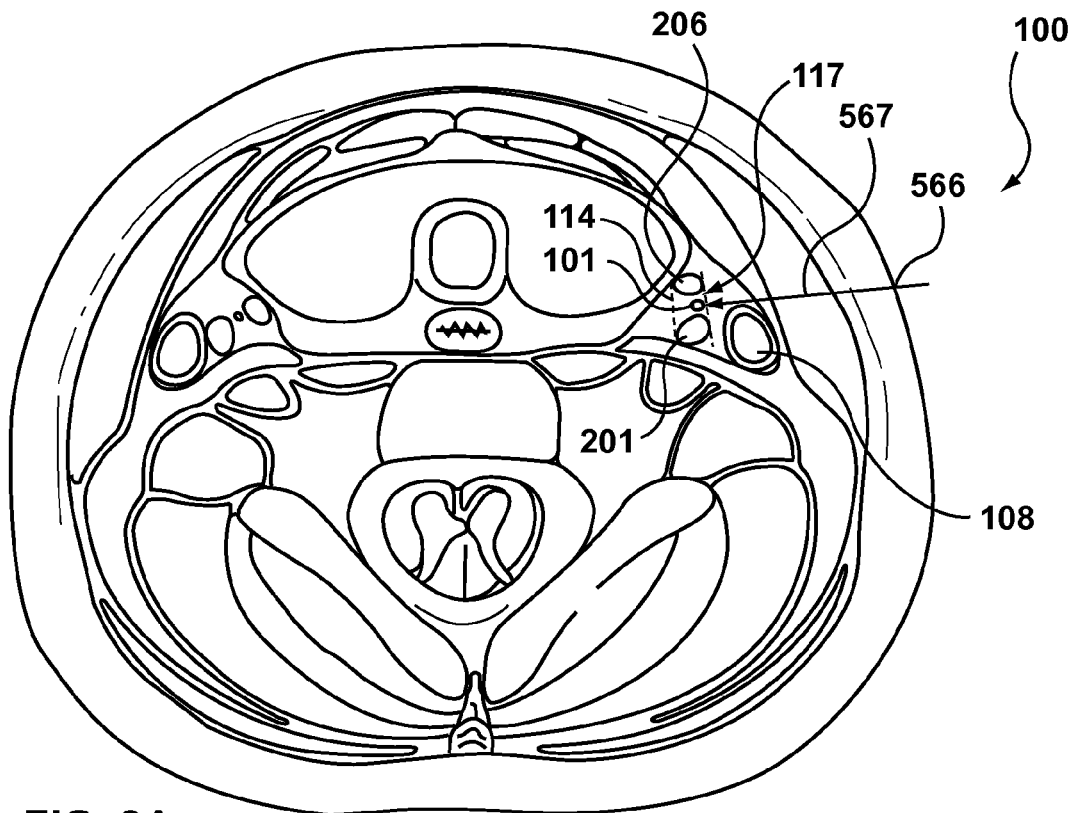
FIGS. 9A and 9B are illustrations of a cross sectional view of a patient's neck showing a posterior percutaneous approach for ablation of a carotid body.
Figure 9B:
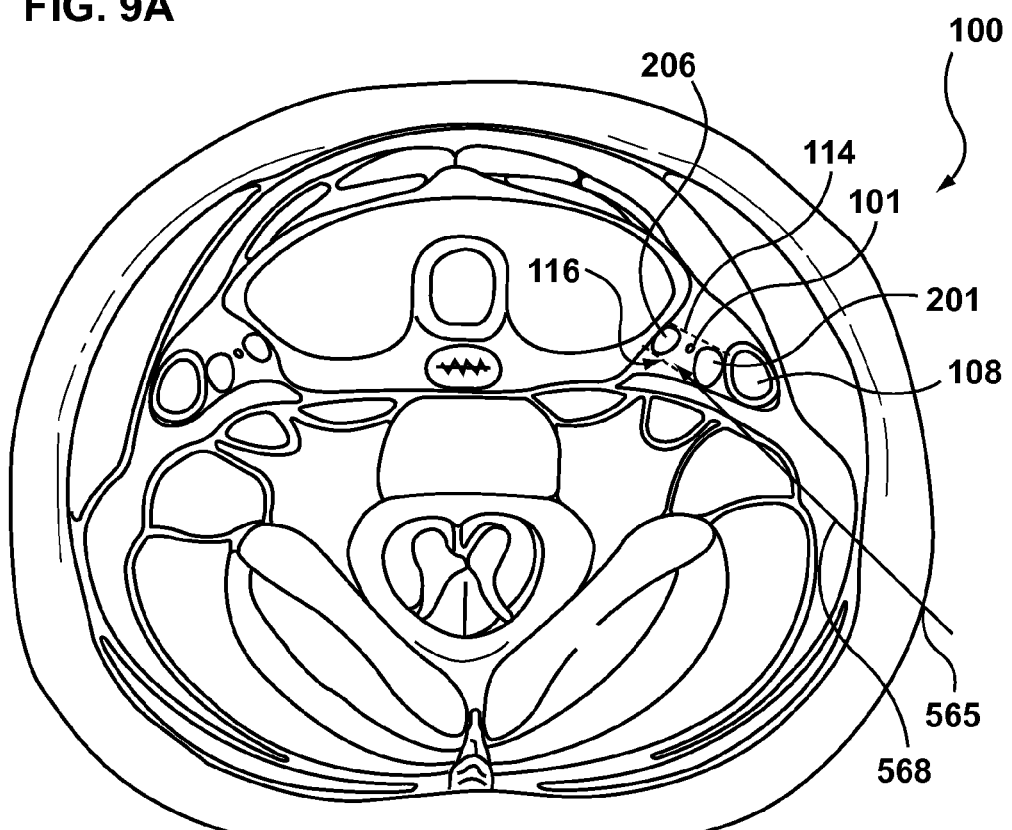

A posterior approach may be chosen to approach the medial or lateral side of a carotid bifurcation. For example, as shown in FIG. 9A, a percutaneous device may be inserted at an insertion site 566 and advanced along a projection 567 to a lateral side 117 of an intercarotid septum 114 or target ablation site. Alternatively, as shown in FIG. 9B, a percutaneous device may be inserted at an insertion site 565 and advanced along a projection 568 to a medial side of an intercarotid septum 116 or target ablation site. A percutaneous device may be inserted posterior of the sternocleidomastoid muscle and advanced anteriorly. Depending on patient specific anatomy, a posterior approach may place a device parallel to the intercarotid septum. A device may benefit from embodiments with side firing or directional ability to specifically target the intercarotid septum.

Figure 10:
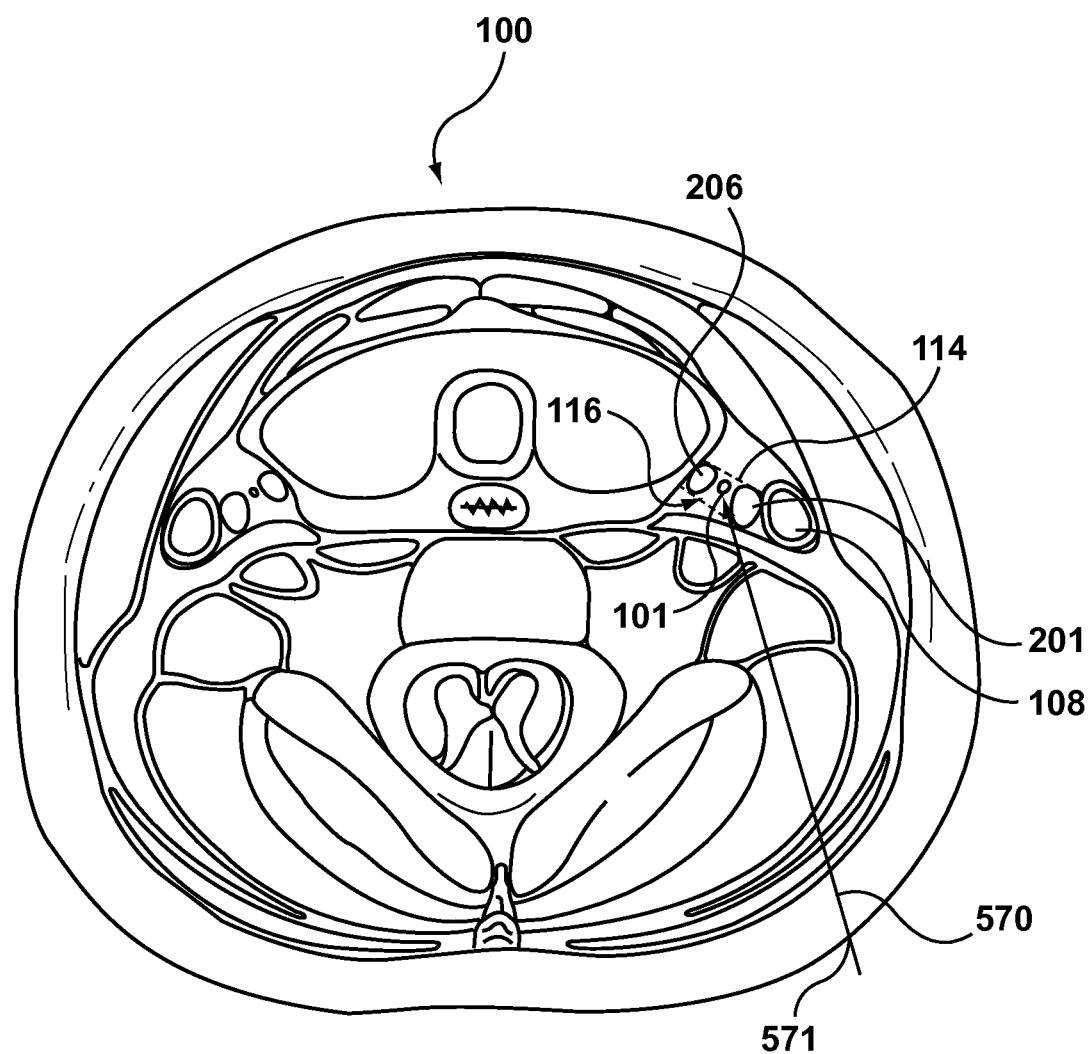
FIG. 10 is an illustration of a cross sectional view of a patient's neck showing a paraspinal percutaneous approach for ablation of a carotid body.

As shown in FIG. 10 the paraspinal approach may require a percutaneous device to be inserted posterior of the sternocleidomastoid muscle. The device insertion site 571 may be 3-5 cm lateral of the midline and passed along a projection 570 adjacent to the transverse spinous processes and guided towards a medial aspect of an intercarotid septum.

The most appropriate anatomical approach depends on the patient's vascular anatomy, such as the position of the carotid bifurcation, the location of the jugular vein, and the location of the CB within the intercarotid septum. Unless noted, the methods and embodiments in this disclosure are universal for each approach. Surgical planning use cases will likely aid the interventionist with selecting, positing, and optimizing one of the desired approaches.

Imaging the Carotid Body and Procedure Planning

Figure 11:
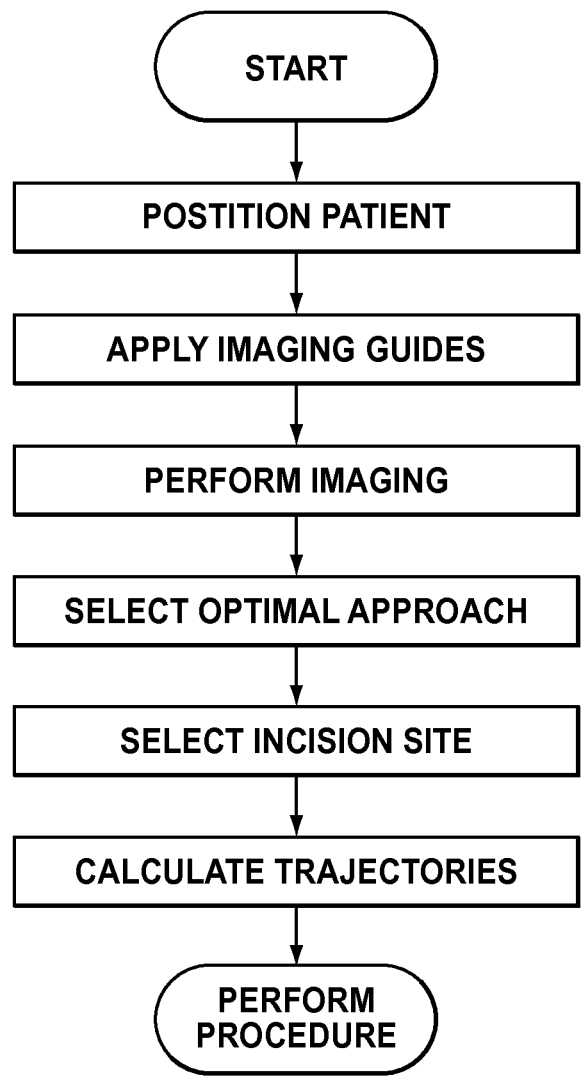
FIG. 11 illustrates a process flow for selecting the optimal surgical approach and trajectories.

There are multiple potential imaging modalities for assessing a patient's suitability for a CBA procedure and for planning a percutaneous carotid body ablation procedure. These technologies may include MRI, fluoroscopy, MRI, CTA, ultrasound, fluoroscopy, and hybrid approaches. Through the application of surgical imaging aids, the optimal trajectory, incision site, and areas to exclude can be determined. FIG. 11 illustrates a process flow for selecting the optimal surgical approach and trajectories.

Real time guidance of a percutaneous ablation device may be critical. Given the dense anatomic geography and potentially high risk of serious injury to surrounding structures, precise guidance of a percutaneous device may be needed. Handheld ultrasound transducers are widely used for needle guidance within soft tissues. Needle guidance systems that may be applicable for targeting a carotid body include robotic surgical systems, magnetic guidance, CT guidance, and others.

A percutaneous device (e.g., needle, cannula, dilation set, probe) may comprise a means for determining depth of penetration or proximity to a target ablation site. For example, the percutaneous device may comprise an imaging modality such as an ultrasound transducer, OCT, or ICE on its distal tip.

Use of Doppler Imaging and Ultrasound Heating

The imaging plane for visualization of carotid arteries and a jugular vein may include Doppler Imaging modes and pulsed wave Doppler mode. Color Doppler image of blood vessels can enable distinction of veins and arteries and assist navigation of percutaneous ablation instruments to a target site (e.g., into a carotid septum). A Doppler sensor can be integrated in the distal section of a percutaneous ablation cannula. The distal cannula assembly containing the ultrasound transducer element of the blood flow imaging sensor may include an ultrasound element capable of high energy delivery and ablation or a cryogenic energy delivery element or an RF energy delivery element (electrode or several electrodes) for ablation.

A cannula may be guided to a target ablation site, such as in a carotid septum, facilitated by ultrasound imaging by identifying the space between an internal and external carotid arteries as characterized by very high blood velocity that is also characteristically pulsatile. For instance, by using low intensity ultrasound Doppler guidance by the means of sensing high velocity pulsatile arterial blood flow in the internal and external carotid artery.

The sample volume of the pulse wave Doppler along the ultrasound beam axis is adjustable in length and location. The location of the sample volume along the beam axis can be set to cover the range of about 5 to 15 mm from the transducer face. The cannula mounted ablation element can be aligned with the aid of Doppler to cover the carotid body for ablation. Once the transducer is determined to be properly aligned, the carotid body is ablated, with the same transducer element, using high intensity continuous wave, or high duty cycle pulsed wave ultrasound or with a different ablation energy applicator. The temperature rise in tissue is monitored in order to prevent ablation of structures (nerves and vessels) that are not intended for ablation.

Alternatively, the ultrasound transducer may consist of an annular array, for instance, a two element array with a center disc for high intensity ablation and outer ring for low intensity Doppler use. Ultrasonic transducer can be designed to rotate inside the cannula in order to create a 360 degree Image of surrounding structures and blood flow in blood vessels.

Perioperative Assessment of Carotid Body Location, Function and Technical Success It may be beneficial to assess location of a percutaneous ablation device through methodologies other than imaging, such as measurable physiological confirmation of the location the device within or near a CB. For example, a percutaneous device may be advanced under imaging guidance to a desired location, a stimulus may be delivered to the location, and a physiological reaction to the stimulus may confirm if the percutaneous device is sufficiently proximate a target ablation site and sufficiently distant from a vital structure to be spared. These methods may also indicate if a percutaneous device is in a position that is not safe for ablation thus indicating that the device should be repositioned. Methods and features of confirming device placement, location of the CB, and technical success may include: electrical stimulation/blockade, localized stimulant infusion/blockade, compressive ischemia-stimulation, obstructive ischemia-stimulation, pre-procedure image(s) referencing, integration of sensors and measurement (e.g., for measuring electrical potentials and contact impedance; concentration of hormones, $O_2$, $CO_2$, $N_2$, hemoglobin, dopamine, ATP; flow or velocity; or temperature). Substances that excite or suppress carotid body function can be infused directly into the carotid body or into the carotid artery by puncturing the wall of the artery using a needle.

Technical success of percutaneous carotid body ablation may be revealed by electrical stimulation, intra-procedure biopsy, ventilation modulation, endovascular ultrasound imaging, dose determination based on pre-procedure imaging—dose delivered vs. not delivered, comparison of baseline chemo-stimulation with contralateral local anesthetic blockade, follow-up computer tomography angiography (CTA).

Percutaneous Cannula and Method of Use

A percutaneous carotid body ablation probe provides a platform for accessing and ablating a target ablation site such as a carotid septum. A percutaneous carotid body ablation probe may comprise an ablation element positioned on a distal region of a probe that may be advanced through a patient's skin to a target ablation site. The probe may have a sharp or blunt distal tip selected to be less traumatic to certain types of tissue such as vessels or nerves. The probe may further comprise a hub or handle to facilitate manipulation of the probe or contain electrical or other connections. Optionally, the probe may also comprise an assessing element at the distal region of the probe such as a stimulating electrode, or a sensor to measure properties such as temperature, pressure, or blood flow.

The probe may further comprise an ultrasonic sensor such as Doppler blood flow sensor.

Figure 12:
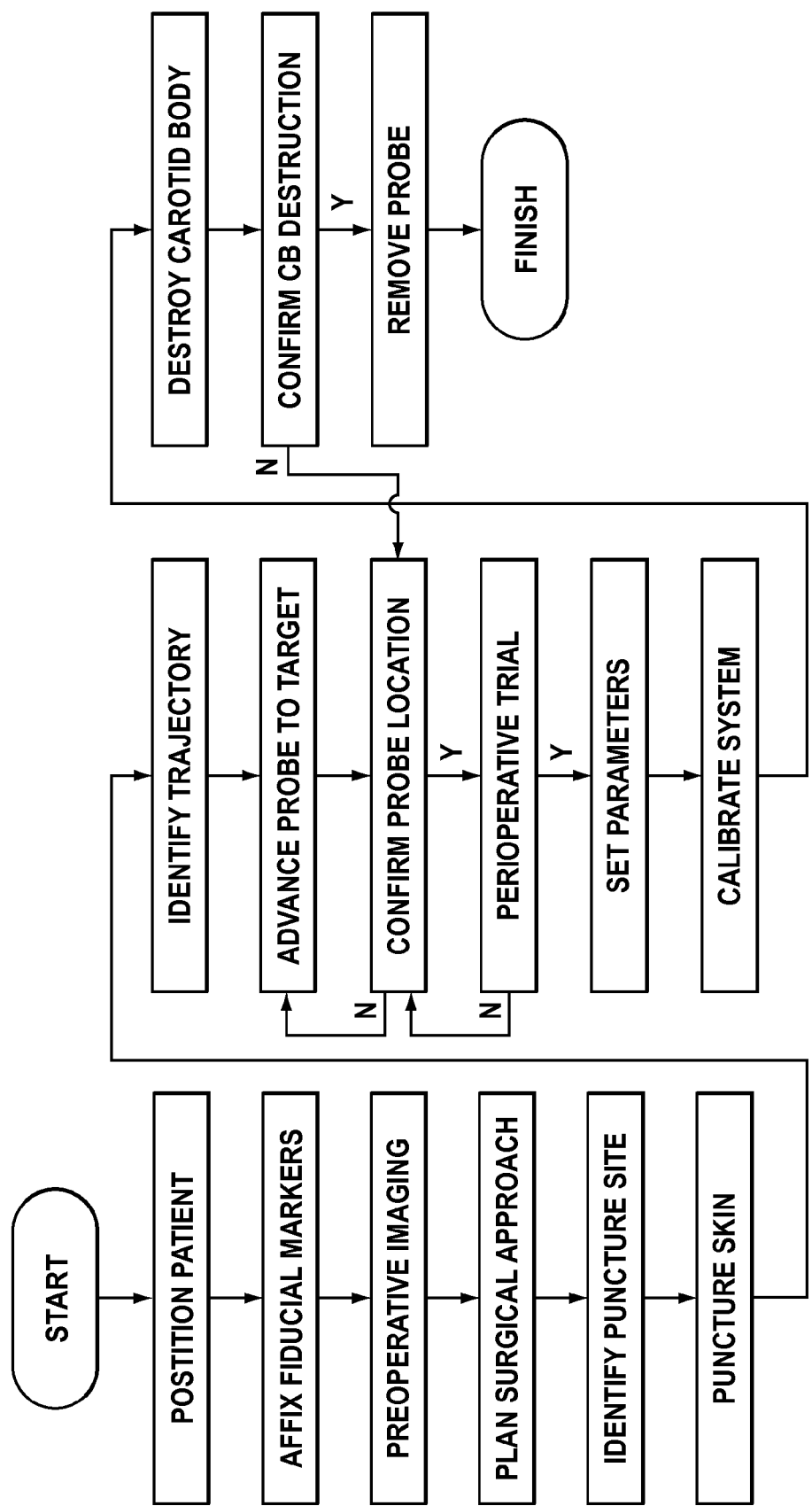
FIG. 12 is a flowchart of a method of using a percutaneous carotid body ablation probe.
Figure 16A:
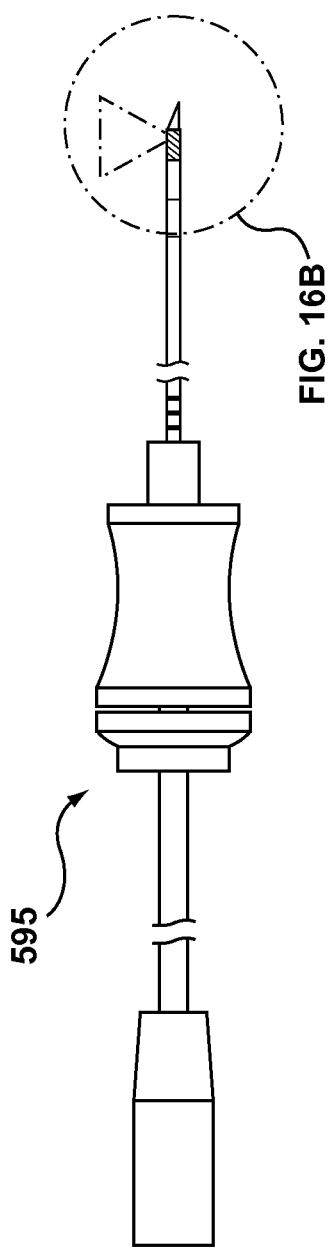
FIGS. 16A and 16B is area schematic illustrations of a percutaneous side-firing laser ablation probe.
Figure 16B:
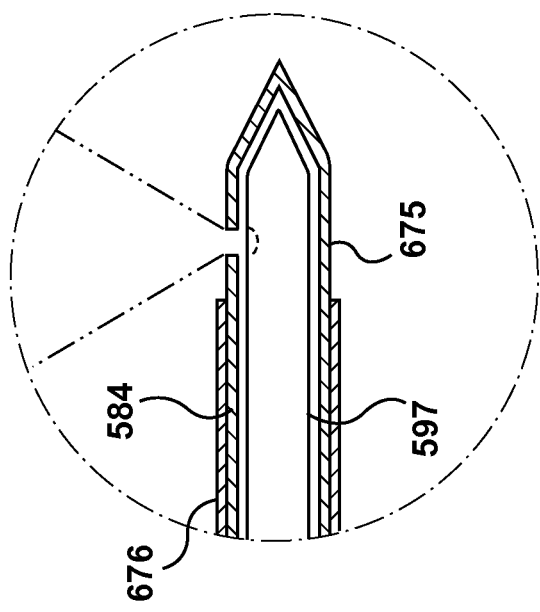

The probe, distal tip hub or a combination thereof may comprise a fiducial marker (e.g., an echogenic marker, a radiopaque marker, a magnetic marker) for identifying trajectory, position, or orientation. A method of using a percutaneous carotid body ablation probe is outlined in the flowchart shown in FIG. 12. Examples of percutaneous carotid body ablation probes are shown in FIGS. 13A and 13B a radiofrequency ablation probe, FIGS. 14A and 14B a bipolar radiofrequency ablation probe, FIGS. 15A and 15B a forward firing laser ablation probe, and FIGS. 16A and 16B a side-firing laser ablation probe. A percutaneous carotid body ablation probe may be configured to deliver other forms of ablative energy such as microwave, high intensity focused ultrasound, low frequency ultrasound, ultrasound, radiation, cryogenic energy sclerosing agents, or ablative chemicals.

The probe may further comprise a means to deliver cryogenic cooling to a carotid septum. In addition to showing the Doppler blood flow in major vessels (e.g., carotid arteries and jugular vein) ultrasound transducer may be used to observe and monitor formation of a cryogenic ice ball. Doppler ultrasound can be further used to observe and monitor accessory arteries that stem from internal or external carotid arteries in the targeted area to avoid their puncture, unintended ablation, perforation and bleeding.

An ultrasound transducer may be placed on an external surface of a patient's neck. There is benefit in placing the transducer as close as possible to the area desired to image. Alternatively, an ultrasonic transducer may be placed in an internal jugular vein or other vein of the neck proximate to a target carotid bifurcation.

As shown in FIGS. 13A and 13B a percutaneous radiofrequency ablation probe may comprise a needle body that has a caliber between or including approximately 17 gauge and 25 gauge, and a length of between or including approximately 3 to 20 cm. The needle body may include an electrically conductive shaft 576 made from, for example, Nitinol or stainless steel. The shaft 576 may be covered in insulation 577 (e.g., polymer or dielectric coating such as PET, PTFE, Polyimide) except for a distal end, which makes an electrode 578. The electrode 578 may have a length between or including approximately 2 to 10 mm (e.g., 5 mm). A temperature sensor (e.g., thermocouple, thermistor, fluoroptic sensor) may be positioned within or proximate the electrode 578. The electrode and temperature sensor are electrically connected to a connector 579 which may be in a hub 580 or at the end of a cable that is connected to the hub, as shown. The connector 579 may be used to plug directly into a radiofrequency generator or into an extension cable that connects to the generator. Electrical communication is provided between the generator and electrode and temperature sensor. Optionally, electrical communication may be provided between an electrical nerve stimulator or nerve block signal generator and the electrode 578 or other stimulation/block electrodes not shown proximate the ablation electrode 578. Optionally, needle shaft 576 may comprise a lumen in fluid communication with a port at or near the electrode 578 used to deliver an ionic fluid for cooling electrode 578, enhancing convective diffusion, or improving electrical continuity between the electrode and tissue. A percutaneous radiofrequency ablation probe may be used in conjunction with a dispersive electrode (e.g., grounding pad) placed on a patient's skin to complete an electrical circuit.

Figure 14A:
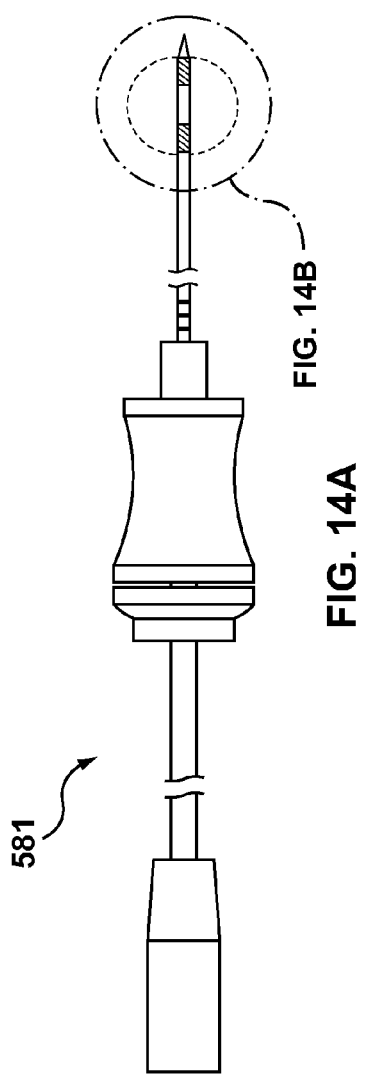
FIGS. 14A and 14B are schematic illustrations of a percutaneous bipolar radiofrequency ablation probe.
Figure 14B:
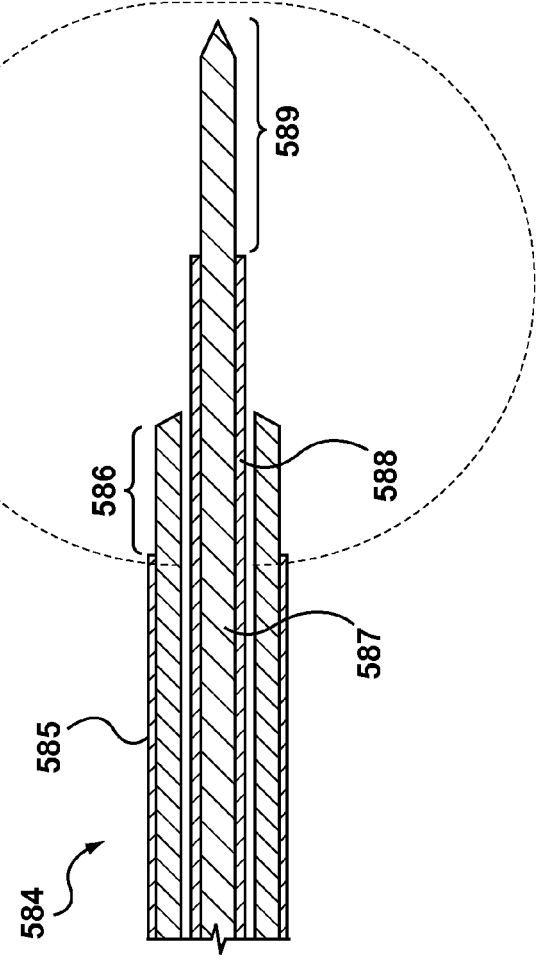

Similar to the percutaneous radiofrequency ablation probe 575, a need may be configured for percutaneous bipolar radiofrequency ablation, as shown in FIGS. 14A and 14B. Both an active 582 and return 583 electrodes may be positioned on a distal region of a percutaneous bipolar radiofrequency ablation probe 581. For example, a percutaneous bipolar radiofrequency ablation probe may comprise a needle shaft 584 made of electrically conductive material such as Nitinol or stainless steel and electrically insulated 585 along its length except for a distal end 586 of about 2 to 5 mm. The needle shaft 584 has a lumen along its axis in which a trocar is positioned. The trocar is electrically insulated with dielectric material 588 along its length except for a distal end 589 of about 2 to 5 mm. The trocar 587 extends beyond the distal end of the needle shaft such that exposed end 589 and exposed end 586 are separated by insulation 588 at a distance of about 2 to 5 mm. The exposed ends are used as active and return electrodes in which radiofrequency current is passed from one electrode through tissue to the other electrode. The trocar electrode 587 may be configured to be removed from the needle shaft 584 lumen so the lumen may be used to inject a fluid, for example anesthetic, contrast, ionic fluid.

An ablation element may be positioned on an expandable structure such as a balloon or mesh cage (not shown). Deploying the expandable structure may facilitate ablation of a target site by compressing tissue surrounding the expandable structure and reducing blood flow through micro vessels in the target ablation site.

As shown in FIGS. 15A and 15B a forward firing laser ablation probe 595 may comprise an optical fiber 597 housed in a lumen of a needle shaft 596 with a distal, forward facing opening 598 through which a laser is emitted. This embodiment may be used to create a heated volume of tissue 599 in the area where the laser is emitted, that is, distal to the distal tip of the laser ablation probe in a conical shape sufficiently coaxial with an axis of the needle. FIG. 16 is a schematic diagram of a side firing laser ablation probe. The percutaneous laser ablation probes with various laser firing directions may be made in a similar fashion yet having a different configuration of opening that directs laser energy in a specific direction and de-cladding of a distal region of the optic fiber to allow laser energy to disperse through the lateral hole. Laser ablation probes may comprise a needle shaft 584 with a caliber between and including about 25 gauge to 17 gauge and a length between and including about 3 to 20 cm. A needle shaft 584 may be made for example, from Nitinol or stainless steel hypodermic tubing. Optionally, the needle shaft may be electrically insulated 676 along its entire length except for at a distal region of about 1 to 5 mm. This electrically exposed region may be used as an electrode 675 for electrical nerve stimulation or blocking. An optical fiber 597 may be positioned within a lumen of the needle shaft 596 for delivering optical laser energy from a laser emitter to a distal opening in the percutaneous laser needle. The optical fiber 597 may be made from glass (e.g., step index laser fiber with low hydroxide and a diameter of about 200 microns for transmitting a high power laser with a wavelength of about 1 to 2 microns). Optionally, a distal end of the optical fiber 597 may be de-cladded for radial dispersion and needle wall heating for supplemental conductive tissue heating. The optical fiber may pass through the needle shaft and through an optical extension of sufficient length to reach a laser emitter from a patient (e.g., about 3 meters long+/−about 1 meter). Positioned at a proximal end of the needle shaft 596 may be a handle or hub to facilitate ergonomic use of the needle. An optical fiber extension and electrical connector in electrical communication with the needle shaft may extend from the hub. The laser needle may comprise other features such as visual enhancers (e.g., radiopaque marker to indicate direction and location of laser opening for visualization with fluoroscopy, echogenic coating to improve visualization by sonography), or sensors (e.g., a temperature sensor may be placed proximate the laser opening). A laser emitter may be a console that is positioned external to a patient. The laser emitter may produce a laser source (e.g., about 200 micron wavelength, or a green light laser with about 532 nm wavelength) with a low absorption coefficient with a power of about 2 to 20 watts continuous output. A green light laser (e.g., 532 nm) may be used due to its strong and selective absorption by hemoglobin to target a capillary bed surrounding the carotid body, since the green light would be strongly absorbed by blood in the capillary bed, and local nerve fibers and sheaths would absorb the green light weakly, thereby providing for neural protection. The console may comprise a black body radiation detector used for laser output control, which may be influenced by temperature feedback or user set control. The console may also display parameters such as time, power, and temperature. The console may further comprise an electrical stimulation/blockade generator used to confirm position near a target site or distant from non-target nerves, or to assess success of a laser ablation.

Percutaneous Toolset and Method of Use

A percutaneous toolset comprising a cannula, trocar, and ablation instrument may allow for a larger working channel for an ablation instrument than a percutaneous ablation probe on its own. This embodiment is suited to larger instruments and the addition of such features as multiple temperature sensors or closed-loop cooling channels. For example, an ablation instrument that may be suitable for use with a cannula and trocar toolset may include a cooled RF probe having circulating, open loop, or weeping cooling channels; multiple temperature sensors to monitor temperature of a long ablation zone; stellate extending electrodes to maximize ablation volume; stellate extending sensors to monitor ablation; or, directional or asymmetric ablation mechanism to reach off-axis targets, which may be useful in particular with lateral and paraspinal approaches. A percutaneous toolset may also allow for multiple instruments to be placed at a target ablation site through the same cannula thus maintaining position and access to the site.

Figure 17:
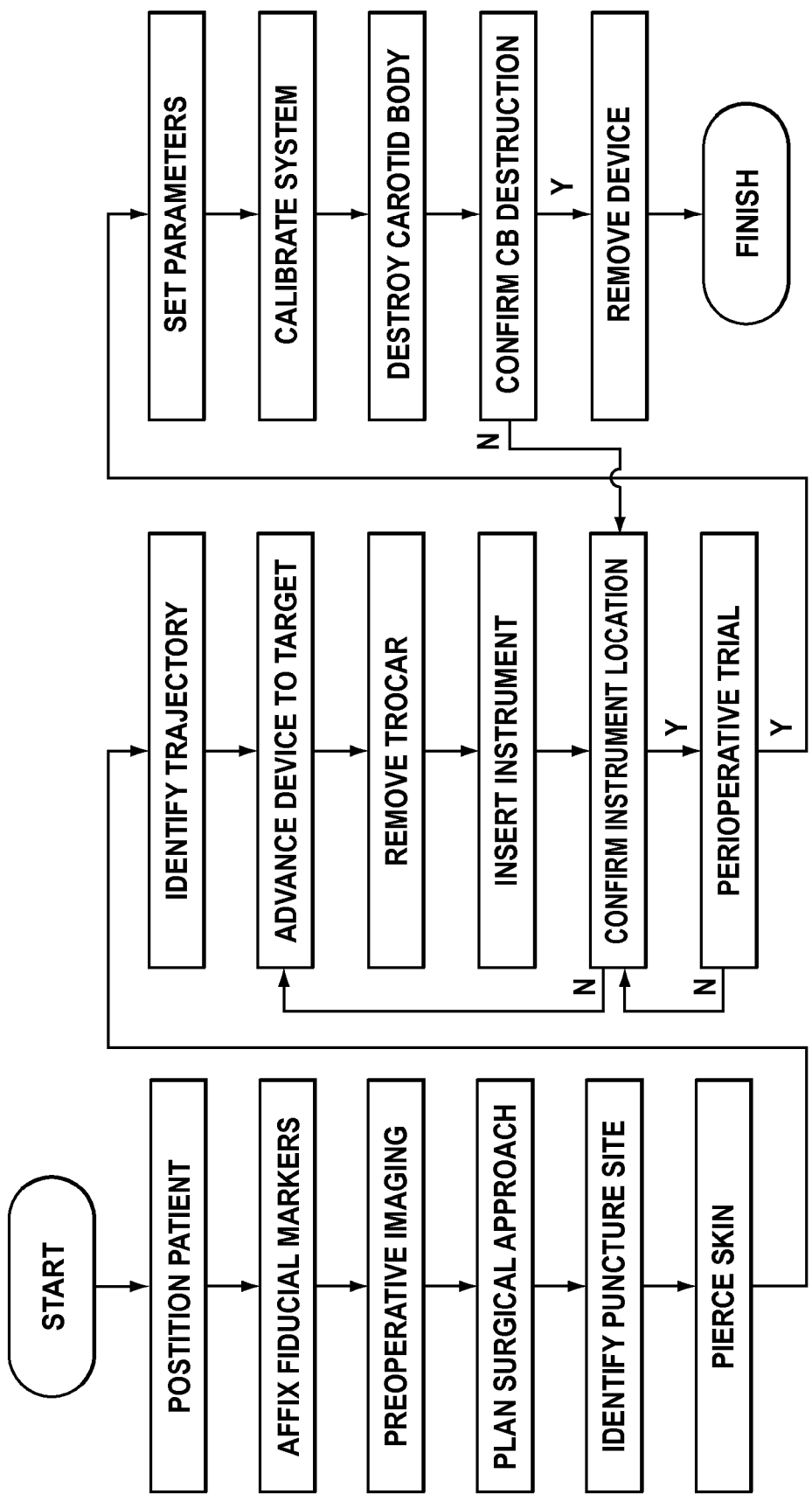
FIG. 17 is a flowchart of a method of using a percutaneous carotid body ablation toolset.
Figure 18:
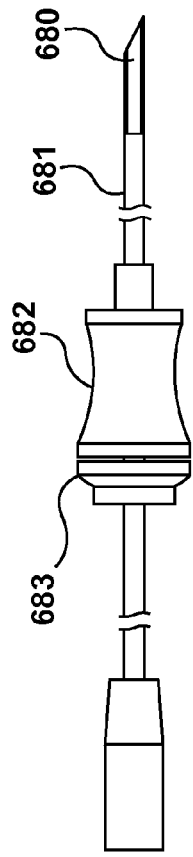
FIG. 18 is a schematic illustration of a percutaneous carotid body ablation toolset.
Figure 19:
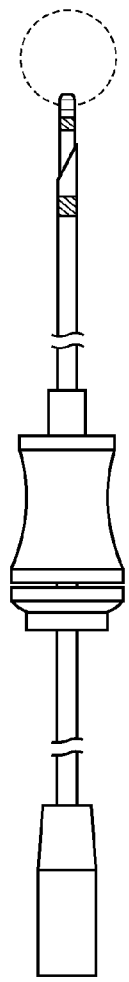
FIG. 19 is a schematic illustration of a percutaneous carotid body ablation toolset with a trocar removed and an ablation instrument inserted.
Figure 20:
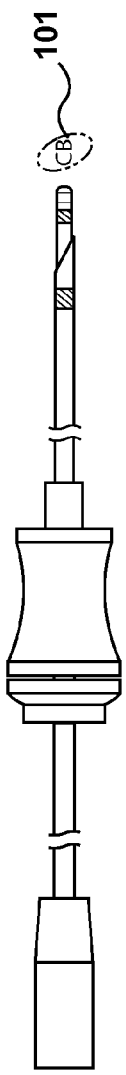
FIG. 20 is a schematic illustration of a percutaneous carotid body ablation toolset with a trocar removed and a radiofrequency ablation instrument inserted.
Figure 21:
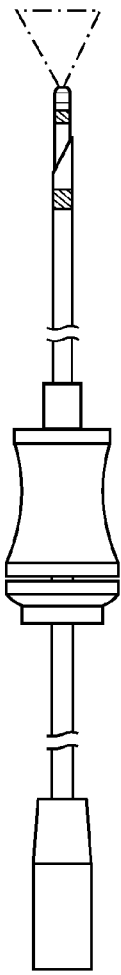
FIG. 21 is a schematic illustration of a percutaneous carotid body ablation toolset with a trocar removed and a forward-firing laser ablation instrument inserted.
Figure 22:
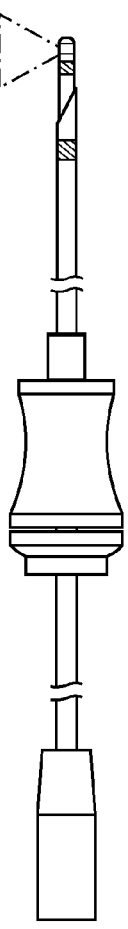
FIG. 22 is a schematic illustration of a percutaneous carotid body ablation toolset with a trocar removed and a side-firing laser ablation instrument inserted.

A method of using a percutaneous toolset is outlined in the flowchart shown in FIG. 17. A cannula containing a trocar may be used to pierce a patient's skin at a predetermined entry site. The cannula containing a trocar may be advanced under visualization (e.g., ultrasound, fluoroscopy, CTA) to a target site. The trocar may then be removed and replaced by an ablation instrument. Optionally, an ablation instrument may be configured for confirming position, for example delivering an electrical stimulation or blockage signal. Is the ablation instrument is placed in a desired position in or proximate a target ablation site, ablation parameters may be set and ablation energy may be delivered. An ablation step may be assessed for success, for example by delivering an electrical stimulation or blockage signal and comparing a reaction to the reaction prior to ablation. If the ablation was unsatisfactory the device may be repositioned for another ablation attempt. If an ablation is satisfactory the cannula containing the ablation instrument may be removed from the patient. Alternatively, the ablation instrument may be removed from the cannula and a fluid, such as anesthetic may be injected through the cannula to the target site prior to removing the cannula. A cannula and trocar are shown in FIG. 18. FIG. 19 shows the cannula with the trocar removed and an ablation instrument inserted. FIG. 20 depicts a percutaneous toolset wherein the ablation instrument is a radiofrequency probe. FIG. 21 depicts a percutaneous toolset wherein the ablation instrument is a side-firing laser ablation probe. FIG. 22 depicts a percutaneous toolset wherein the ablation instrument is a forward-firing laser ablation probe. A percutaneous carotid body ablation probe may be configured to deliver other forms of ablative energy such as microwave, high intensity focused ultrasound, ultrasound, low frequency ultrasound, radiation, cryogenic energy sclerosing agents, or ablative chemicals.

As shown in FIG. 18 a trocar 680 may fit slidably within a cannula 681 and have a sharpened distal tip that sits approximately flush with a sharp distal tip of the cannula. Alternatively, a cannula may have a square cut distal tip and a trocar may have a sharpened distal tip and extend beyond the distal tip of the cannula (not shown). A trocar may prevent tissue from entering a cannula as they are inserted through tissue. Optionally, a trocar may comprise an active element such as an electrode or sensor. Such trocars may comprise a cable 684 extending from a trocar hub 683 terminating with an electrical connector 685. A hub 682 may be positioned at a proximal end of cannula 681 to facilitate ergonomic manipulation of the cannula. The hub 682 may be configured to align with and securely fit with a hub 683 of a trocar in order to align and position a distal tip of the trocar properly with the distal tip of the cannula. The cannula hub 682 may also align with and securely fit with a hub of an ablation instrument when fully inserted into the cannula. A trocar, cannula, hub, instrument(s), or a combination may include integrated fiducial markers for trajectory, position, and orientation tracking (e.g., echogenic element to facilitate sonography, radiopaque element to facilitate x-ray, fluoroscopy, and CTA, magnetic element, physical graduations such as depth markers, rotational alignment, instrument alignment).

Figure 6:
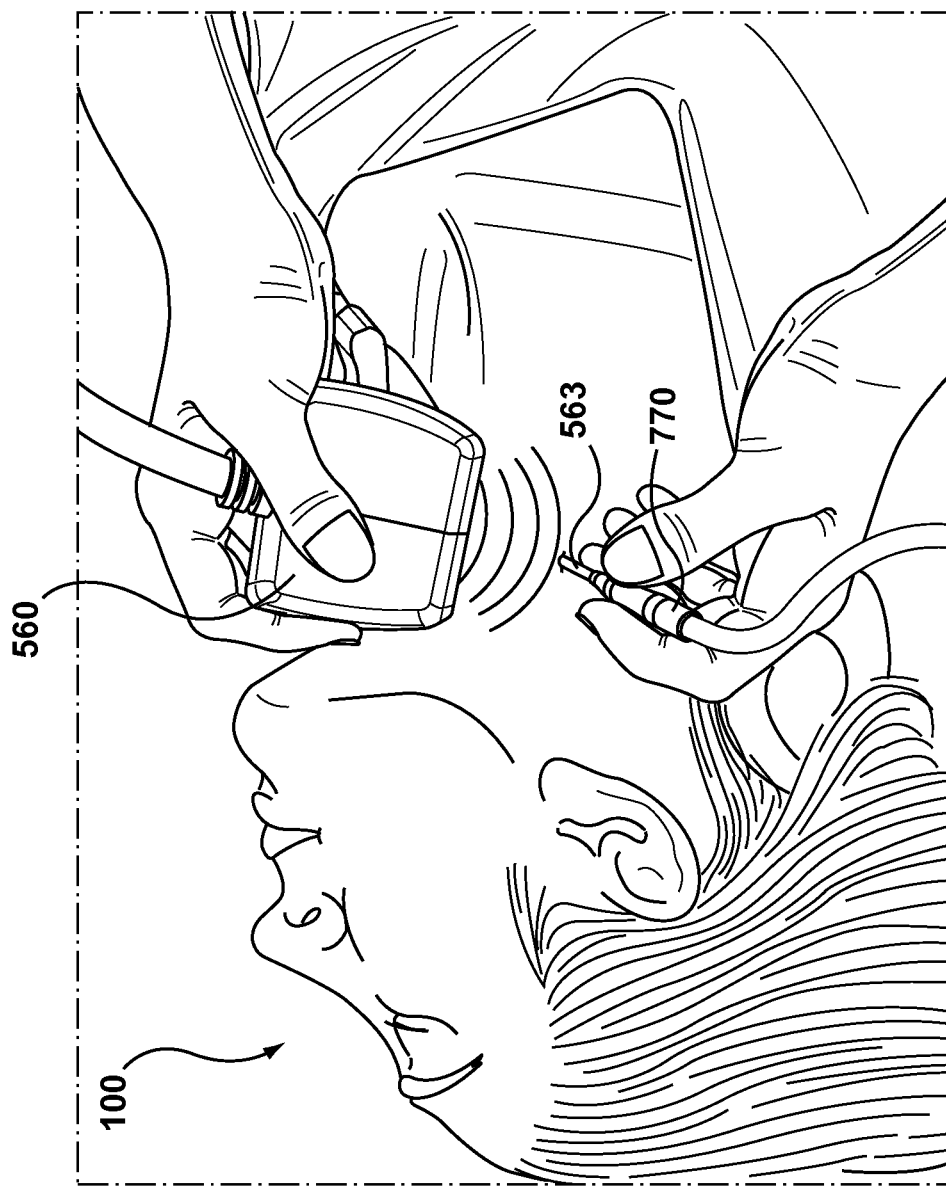
FIG. 6 is an illustration showing a percutaneous ablation probe in position for carotid body ablation with an ultrasonic imaging probe being used to monitor the position.
Figure 7:
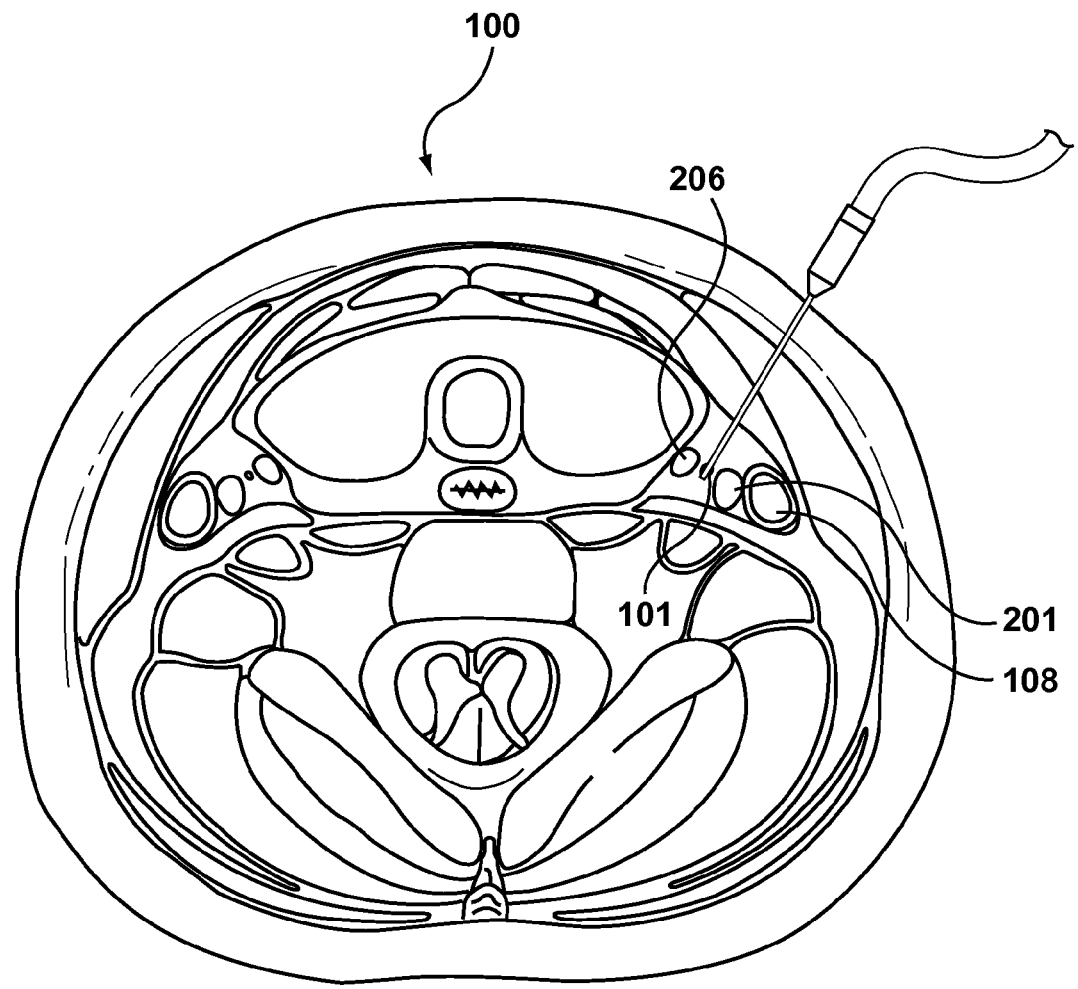
FIG. 7 is an illustration of a cross sectional view of a patient's neck showing a percutaneous ablation probe in position for ablation of a carotid body.

FIG. 6 is an illustration of percutaneous access procedures for percutaneous carotid body cryo-ablation. FIG. 5 shows an extracorporeal ultrasonic imaging transducer 560 guiding insertion of percutaneous cannula 563 into a target site for carotid body cryo-ablation. The cannula 563 may have an echogenic coating to facilitate visualization with sonography. The echogenic coating may include microbubbles of gas immobilized in the polymeric coating. Once the cannula 563 is positioned with its distal end near or in a target ablation site, for example as confirmed using visualization such as ultrasound sonography, a trocar may be removed from the cannula 563 and a cryo-ablation probe 770 may be inserted into a lumen of the cannula 563 as shown in FIG. 6. As shown, an operator is holding an ultrasonic imaging transducer 560 against skin on the patient's neck. Alternatively, an imaging probe may incorporate a cannula guide in order to facilitate cannula positioning and visibility by keeping it in plane of a monographic image. Optionally, once an initial cannula is placed in a desired location the cannula may be dilated from a small diameter to a larger diameter cannula by exchanging the larger diameter cannula over the smaller diameter cannula. This may provide a larger working channel for a percutaneous ablation probe if needed while allowing the use of a smaller diameter cannula for initial placement. Alternatively, a cryo-ablation probe may be inserted through tissue to a target ablation site directly (e.g., without the use of a cannula). FIG. 7 is a cross sectional illustration of a neck of a patient 2 depicting a percutaneous cryo-ablation probe 770 ablating a carotid body 101 within an intercarotid septum 114, between external carotid artery 206 and internal carotid artery 201.

Percutaneous Dilation Set and Method of Use

A carotid body ablation dilator set may allow for an even larger access portal to a target ablation site. Advantages of the larger access port can include allowing a scope to pass to the carotid body for visual confirmation, passage of larger instruments such as hemostats pliers, curettes, biopsy or other mechanical removal methods. A dilation set may comprise a series of incrementally larger cannula tubes that pass over one another to expand the tissue to the size of the largest dilator outer diameter. Once a dilator has been placed to achieve a desired working channel size, smaller dilators within the largest dilator may be removed from a lumen of the largest dilator and instrumentation may be placed through the working channel to a target site. Alternatively, one or more cannulae may be placed in the working channel, which may provide multiple working lumens for passing instruments simultaneously. The dilators may comprise fiducial markers (e.g., echogenic element to facilitate sonography, radiopaque element to facilitate x-ray, fluoroscopy, and CTA, magnetic element, physical graduations such as depth markers, rotational alignment, instrument alignment) to facilitate visualization and positioning of instrumentation at a target site. A dilation set may incorporate multiple sizes to accommodate different sized patients and the various approach paths (e.g., a paraspinal approach dilation set may be longer than an anterior approach dilation set). A dilation set may comprise an off-axis distal opening, which may be used to access a target site that is not in front of a placed dilation set but to a side, for example during a lateral or paraspinal approach.

Figure 23:
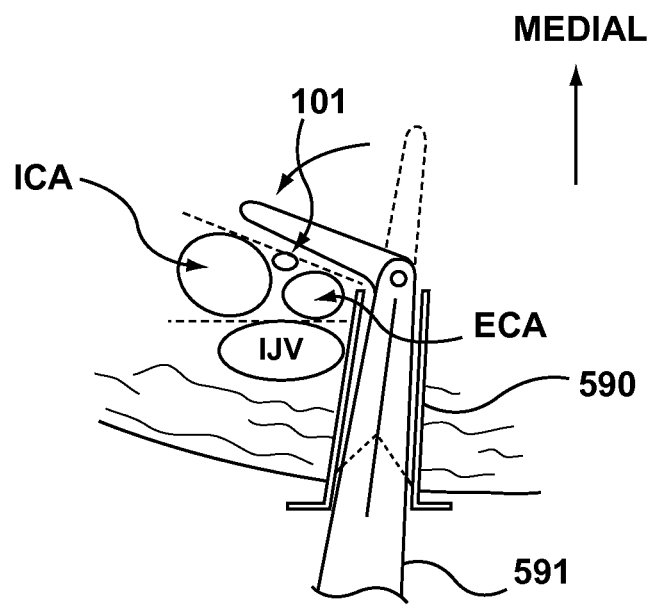
FIG. 23 is a schematic illustration of an articulating ablation tool positioned in a percutaneous dilator.
Figure 24:
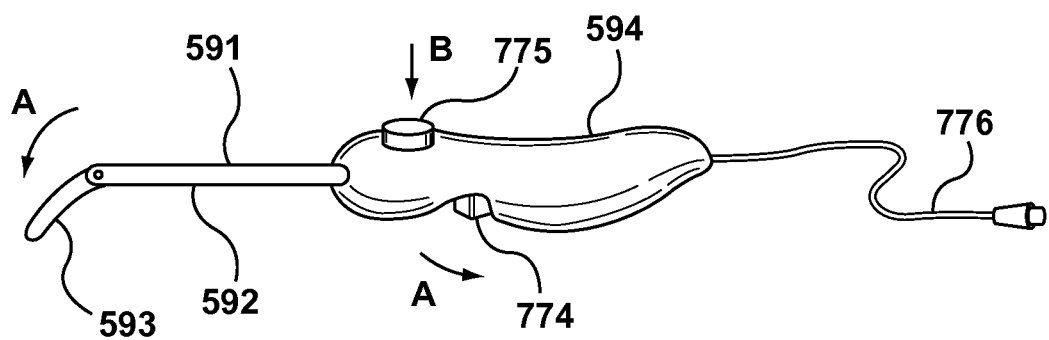
FIG. 24 is a schematic illustration of an articulating ablation tool.
Figure 25:
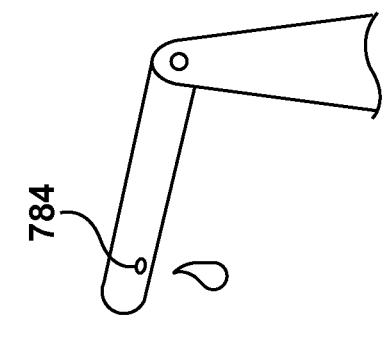
FIG. 25 is a schematic illustration of an articulating arm having a radiofrequency electrode.
Figure 26:
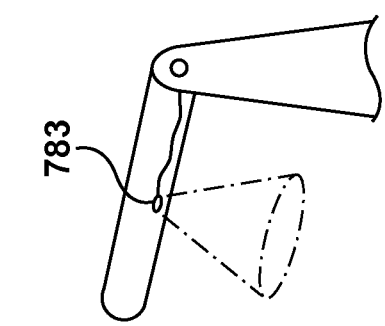
FIG. 26 is a schematic illustration of an articulating arm having a high frequency ultrasound transducer.
Figure 27:
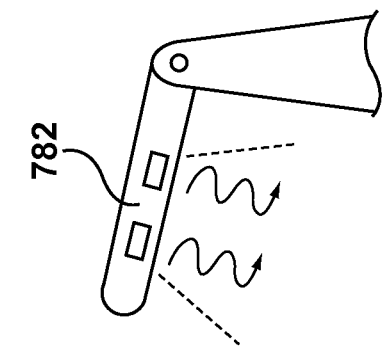
FIG. 27 is a schematic illustration of an articulating arm having a laser emitter.
Figure 28:
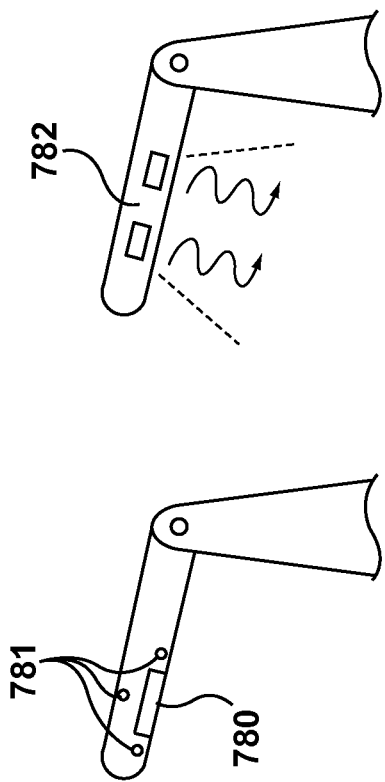
FIG. 28 is a schematic illustration of an articulating arm having a chemical delivery port.
Figure 29:
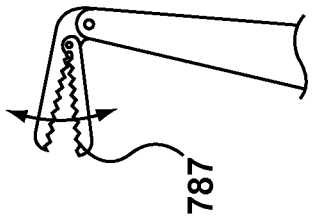
FIG. 29 is a schematic illustration of an articulating arm having a curette.
Figure 30:
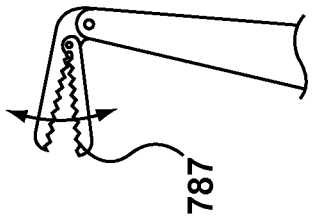
FIG. 30 is a schematic illustration of an articulating arm having bipolar radiofrequency electrodes.
Figure 31:
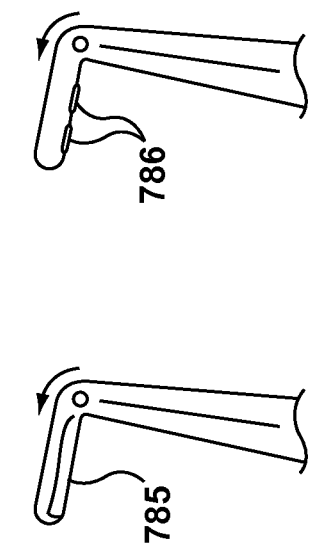
FIG. 31 is a schematic illustration of an articulating arm having a hemostat.

A percutaneous dilator set may be used to deliver articulating minimally invasive surgical tools (e.g., keyhole surgery tools). As shown in FIG. 23 percutaneous dilator 590 provides access to a region near a target ablation site (e.g., carotid body 101, or intercarotid septum). An articulating ablation tool 591 is delivered to the target site through the dilator 590. For example, the dilator may provide a working channel with a width up to about 1 cm. As shown in FIG. 24 an articulating ablation tool 591 may have a shaft 592 that may be between approximately 3 to 20 cm long, an articulating arm 593 that may be between approximately 0.5 to 3 cm long, and a handle 594 having an articulation actuator 774, other controls such as an ablation activation switch 775, and an electrical cable connectable to an ablation console or generator. FIG. 25 is a schematic illustration of an articulating arm having a radiofrequency electrode 780 and sensors 781 (e.g., for stimulating or blocking a nerve to confirm suitable positioning, or for monitoring ablation such as temperature sensors). FIG. 26 is a schematic illustration of an articulating arm having a high frequency ultrasound transducer 782. FIG. 27 is a schematic illustration of an articulating arm having a laser emitter 783. FIG. 28 is a schematic illustration of an articulating arm having a chemical delivery port 784. FIG. 29 is a schematic illustration of an articulating arm having a curette 785. FIG. 30 is a schematic illustration of an articulating arm having bipolar radiofrequency electrodes 786. FIG. 31 is a schematic illustration of an articulating arm having a hemostat 787.

Integrated Ultrasound Imaging and Placement Tool

Figure 32:
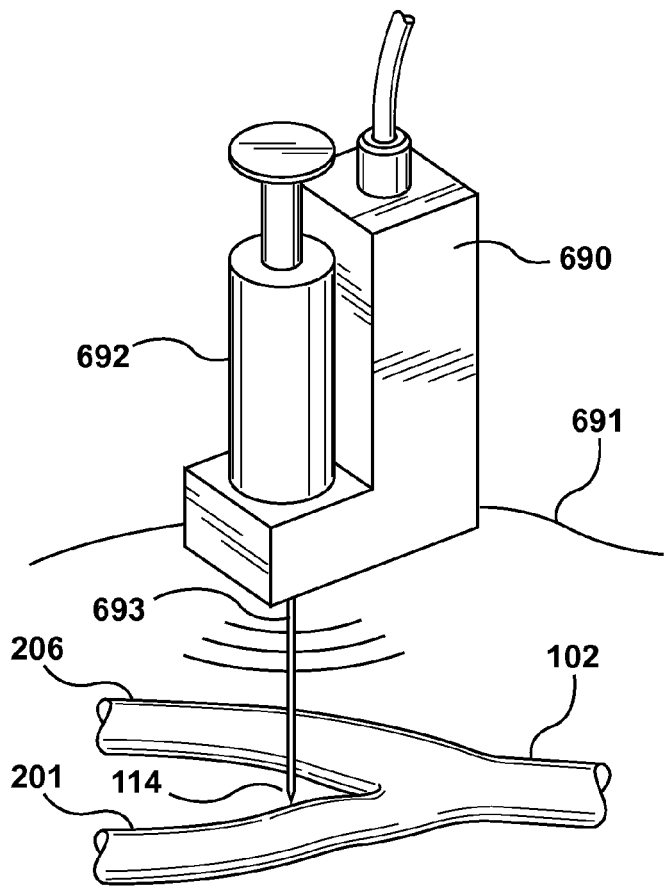
FIG. 32 is a schematic illustration of an integrated ultrasound imaging and placement tool held on an external surface of a patient's skin and focused in a direction of a target ablation site.
Figure 33:
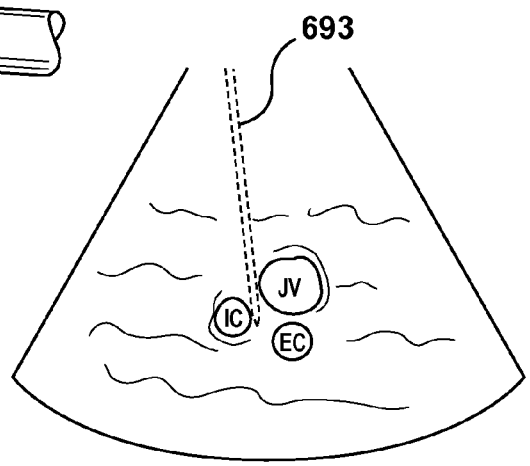
FIG. 33 is a schematic illustration of an image that may be shown on an ultrasound image monitor produced by the ultrasound transducer guiding a percutaneous device to a target site.
Figure 34:
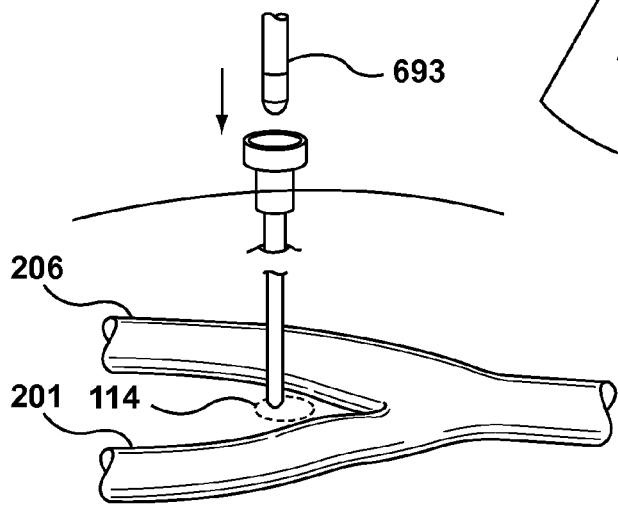
FIG. 34 is a schematic illustration of a percutaneous toolset placed at a target ablation site ready for a percutaneous ablation device to be inserted into a cannula.

FIG. 32 is a schematic illustration of an integrated ultrasound imaging transducer and placement tool 690 held on an external surface of a patient's skin 691 and focused in a direction of a target ablation site (e.g., intercarotid septum 114). The tool 690 comprises an instrument guide 692 aligned with the imaging focus such that a percutaneous device 693 (e.g., percutaneous carotid body ablation device, percutaneous toolset, percutaneous dilation set) inserted through the instrument guide 692 will be directed along a path of focus to the target ablation site. During perioperative integrated external ultrasound guidance, the device may record and report percutaneous device position, percutaneous device estimated trajectory, percutaneous device depth from skin, percutaneous device distance to target, or percutaneous device distance to undesired anatomy. FIG. 33 is a schematic illustration of an image that may be shown on an ultrasound image monitor produced by the ultrasound transducer guiding a percutaneous device 693 to a target site (e.g., as shown a target may be an intercarotid septum between an internal carotid artery IC and external carotid artery EC) and avoiding structures such as the internal jugular vein JV. Optionally, real-time three/four dimensional ultrasound imaging (e.g., as is known in the art of obstetrics) may be used to identify a target ablation site, indicate a percutaneous device trajectory and depth, and indicate proximity of a percutaneous device tip to the target ablation site. As shown in FIG. 34 the tool 690 may be used to place a percutaneous toolset (e.g., cannula and trocar) at a target ablation site and then removed while a percutaneous ablation device is inserted into the cannula 563.

Alternatively, real-time bi-plane imaging (RTBi) may be used to provide multiple ultrasound images of a patient's tissues during insertion of a percutaneous device. To enhance ultrasound visualization of a percutaneous device in tissue the percutaneous device may comprise an echogenic coating. RTBi simultaneously displays two real-time ultrasound images from two separate transducers. The imaging parameters of each transducer (including gain, depth, focal position, tissue harmonics and dynamic range) can be adjusted independently. By providing image guidance from two different scan planes, RTBi can improve the accuracy of placement of a percutaneous device and the monitoring of an interventional procedure. One transducer may be configured as an imaging and placement tool having an instrument guide, similar to the imaging and placement tool 690 shown in FIG. 32. A second transducer may be used to provide an image in a different plane than the first transducer. Together, the two ultrasound images may provide two two-dimensional images in different planes that facilitate precise placement of an ablation element in a target ablation site such as a carotid septum. For example, the first transducer containing an instrument guide may provide an image plane showing an instrument trajectory while a second transducer may simultaneously provide an image plane that may be moved, tilted or rotated relative to the first transducer to observe features from different angles or views than may intersect with the first image plane. For example, this may be useful to verify depth, identify blood vessels or nerves to avoid, identify instrument position relative to various carotid septum boundaries, or identify ice formation in the case of a percutaneous cryogenic carotid body ablation procedure. An example embodiment of a method of percutaneous carotid body ablation using RTBi comprises the following steps: 1) an first ultrasound imaging transducer is placed on a patient's neck and maneuvered to find a first plane that transects the patient's internal, external and common carotid arteries (e.g., a sagittal plane of a carotid bifurcation); 2) a second ultrasound imaging transducer connected to or having an instrument guide 690 is placed on a patient's neck an maneuvered to find a second plane that is different from the first plane and intersects with the first plane (e.g., a transverse plane through the internal and external carotid arteries with a carotid septum between them such as the image shown in FIG. 33). The first and second imaging planes may be for example approximately orthogonal to one another. The second transducer may be placed so that the instrument guide will direct a percutaneous device through a trajectory that will safely pass through tissue to a target ablation site (e.g., a carotid septum) and also provide an image of depth of percutaneous device penetration. The first transducer may provide a complimentary image of an intersecting plane showing a carotid septum, which may facilitate alignment of the device within the septum or to visualize a jugular vein to avoid puncturing it. 3) A percutaneous device is inserted through the instrument guide and through tissue along said trajectory to the target site while monitoring both the first and second ultrasound image; 4) Advancement of the device is completed when an ablation element associated with the device is positioned in a desired location relative to a target ablation site (e.g., in a carotid septum), which may be confirmed with the first and second ultrasound images.

A monitor may simultaneously display the two imaging planes. Each imaging plane may also have a line indicating where the plane intersects with the other plane. Optionally, the two transducers of an RTBi system may be held in place by a clamp such as the collar clamp 790 shown in FIG. 37B. An ultrasound mode may be used to enhance visualization of blood vessels or nerves or a carotid body. For example, Doppler flow imaging may enhance blood vessels such as the carotid arteries or jugular vein.

Fiducial Markers and Positioning Guides

Figure 35:
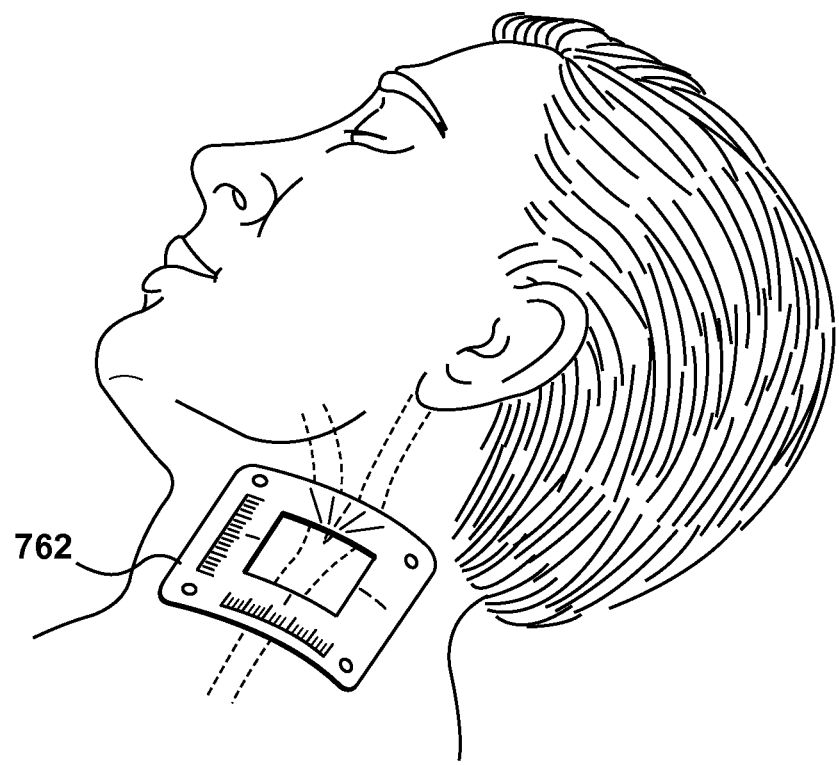
FIG. 35 is a schematic illustration of a template having fiducial markers placed on or adhered to a patient.

A fiducial marker is an object that is visible in the field of view of a given imaging modality and its presence provides a geometric reference to anatomy, other fiducial markers, or objects. Fiducial markers may be useful for determining a position of a target ablation site (e.g., intercarotid septum, carotid body, carotid body nerve) with respect to other points of anatomy such as a location on a patient's skin surface. Fiducial markers may be constructed from a high contrast material that appears on imaging modalities (e.g., platinum, tungsten, SiO4, BaSO4, or lead). Fiducial markers may be affixed to a patient using an adhesive to stick directly to skin. As shown in FIG. 35 fiducial markers may be laminated within a template 762 that may be placed on or adhered to the patient. They may be implanted within or secured to tissue or bone.

Fiducial markers may be used as a reference for overlaying multiple imaging modalities. For example, pre-operative imaging may involve an imaging modality such as CTA or MRI to identify a position of a target site relative to placed fiducial markers, and then a different imaging modality such as fluoroscopy may be used for perioperative guidance to determine trajectory to the target site. The fiducial markers may allow saved pre-operative images to be overlaid on the perioperative images by aligning images of the fiducial markers on both images. The fiducial markers may also be useful to determining scale, and angle of alignment to properly overlay images. Fiducial markers may facilitate procedure planning by indicating an insertion point on patient's skin; indicating areas or trajectories to be avoided during procedure due to anatomy or other factors, such as, vessels, nerves, or other susceptible tissue; determining orthogonal imaging planes to plan trajectory; determine trajectory angles from off plane; be placed on underlying anatomy of interest (e.g., form radiopaque grid to aid in the projection of the underlying anatomy). Fiducial markers may also be incorporated into devices such as an attachment for a cannula or probe guide or similar apparatus.

Cervical Positioning Collar

Figure 36:
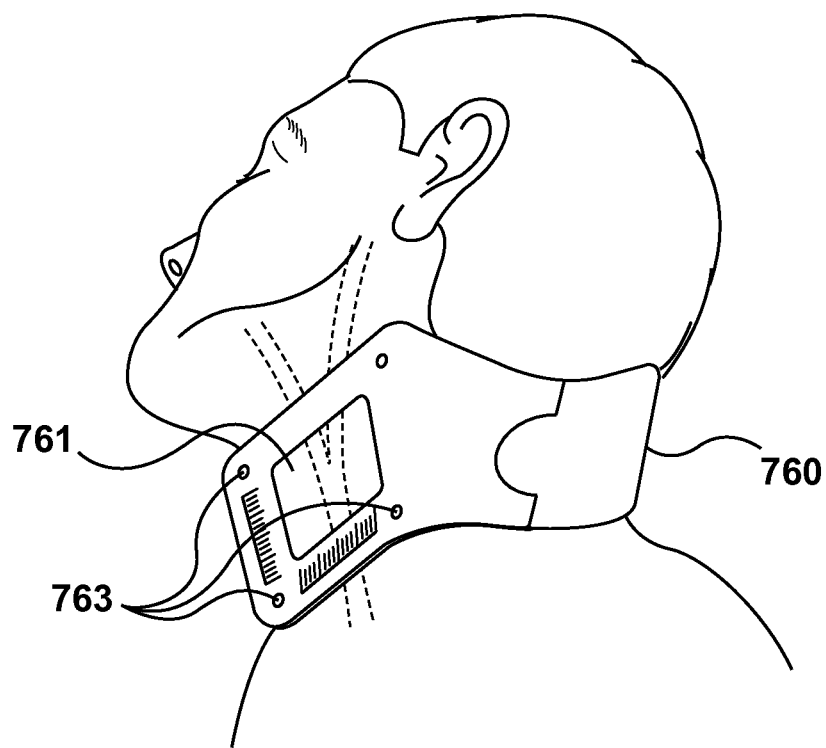
FIG. 36 is an illustration of a cervical positioning collar.
Figure 38:
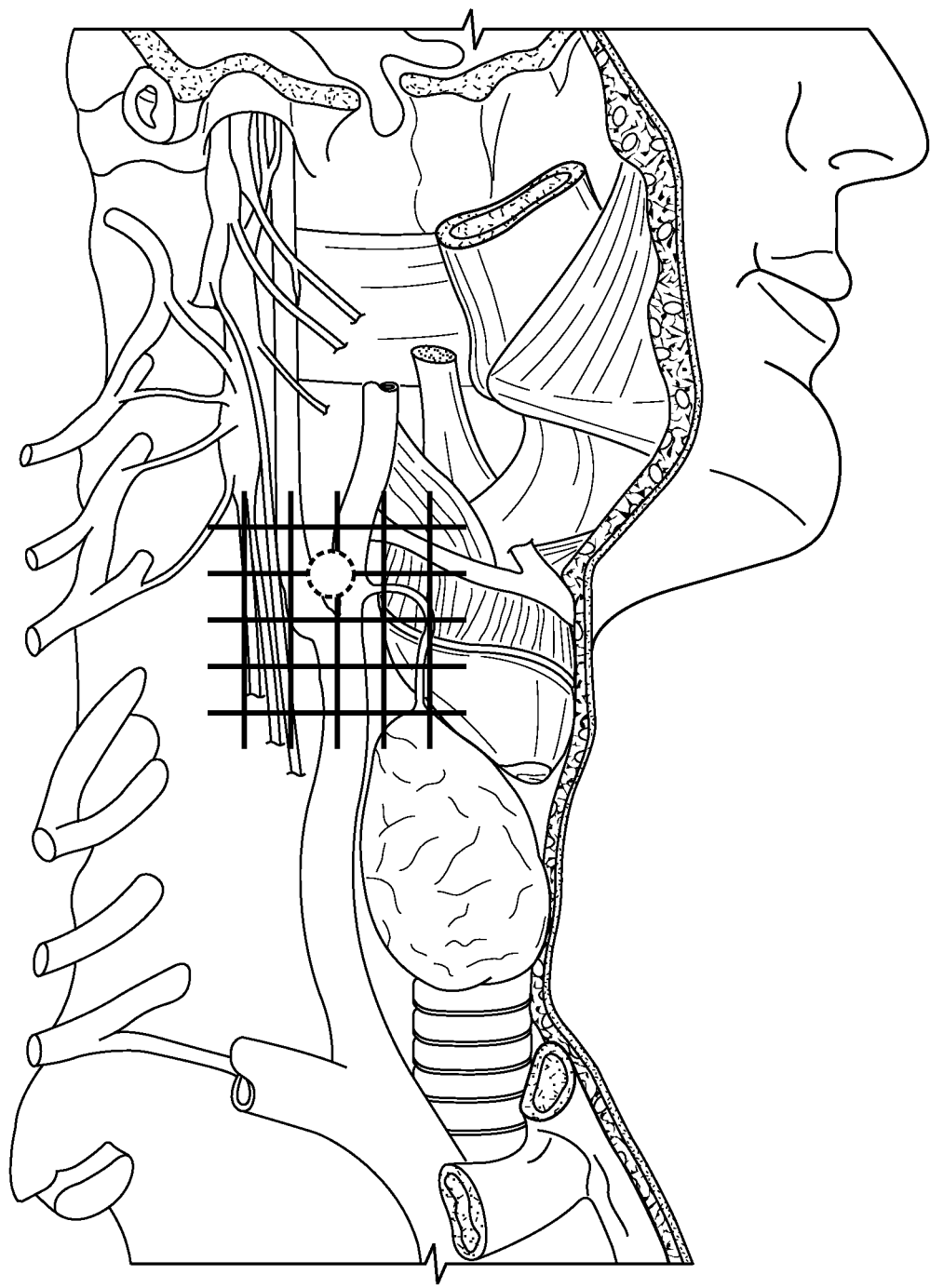
FIG. 38 is an illustration of a coordinate system created by fiducial markers.

FIG. 36 is an illustration of a cervical positioning collar 760, which may be used to optimally position a patient for percutaneous carotid body ablation. Furthermore, the collar is intended to allow for consistent positioning between preoperative imaging, surgical planning, and a procedure. The collar 760 rigidly secures a patient's neck position (e.g., rotation and tilt) in a position that may be suited for carotid body ablation by appropriately orienting anatomy (e.g., exposing an intercarotid septum to a linear track, reducing incidental accessory anatomy, or move vital structures away from the target ablation site). An appropriate neck position for carotid body ablation may include a neck rotation of about 0 to 45 degrees (e.g., about 45 degrees) and an extension of the neck of about 0 to 20 degrees (e.g., about 20 degrees). A practitioner may have multiple collars with varying sizes and neck positions on hand when conducting pre-operative imaging so the most appropriate neck position for a given patient may be chosen. As shown in FIG. 36 a collar 760 may comprise a working window 761 that allows access to a patient's skin while the collar is in place. The collar may comprise fiducial markers 763 that, when aligned under an imaging modality, aides in the surgical procedure planning. For example, the fiducial markers 763 may provide a coordinate system as shown in FIG. 38 or measurements associated with an angle of percutaneous device trajectory, location of a puncture site, trajectories or locations to be avoided.

Figure 37A:
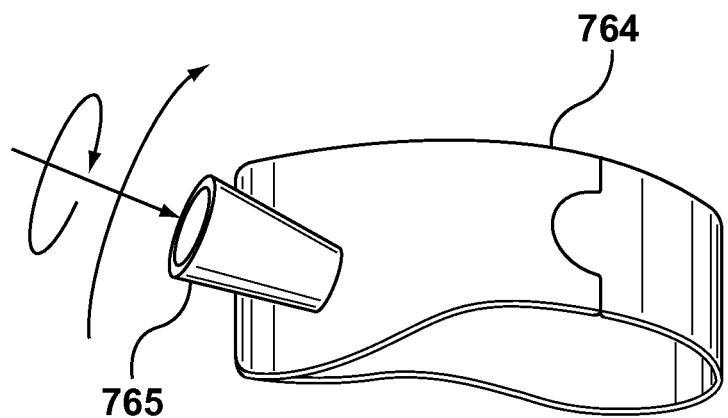
FIG. 37A is an illustration of a collar having a cannula guide.

FIG. 37A shows a collar 764 having a needle guide 765 that controls the trajectory, depth, and rotation of a needle. The needle guide may be set to a prescribed incision, location, trajectory, or depth.

Figure 37B:
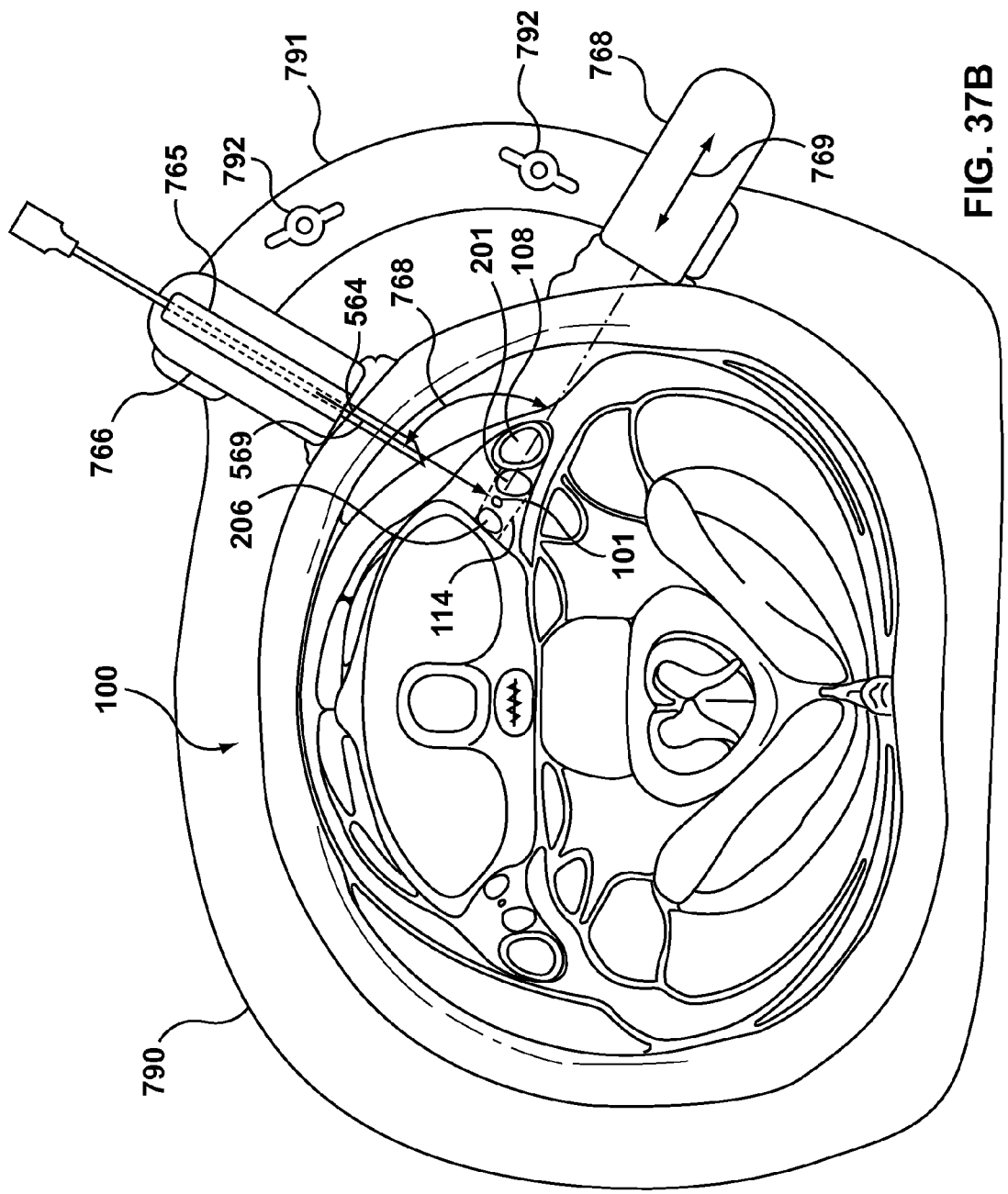
FIG. 37B is an illustration of a collar with a fixture for holding multiple ultrasound imaging transducers.

FIG. 37B shows a fixture 791 that may be adjustably fixed to collar 790 with clamps 792 and that rigidly contains two ultrasound transducers 766 and 767 for bi-planar sonography during a percutaneous carotid body ablation procedure. A first ultrasound imaging transducer 766 may be aligned along a projection 569 to a target site (e.g., carotid body 101). A second ultrasound imaging transducer 767 may be aligned at an angle 768 (e.g., about 90 degrees) to the first transducer 766 to view a plane perpendicular to the plane provided by the first transducer, which may be used to indicate depth of penetration of a percutaneous device (e.g., percutaneous cannula 563, percutaneous ablation device 562, or percutaneous dilation set 590). One or both of the transducers 766 and 767 may be adjustably connected to the fixture 791 to modify radial distance 769. A percutaneous carotid body ablation procedure may be facilitated with the ultrasound transducers rigidly connected to the collar 790, which may be fitted to a patient's neck. For example, multiple plane images may be provided while the transducers are maintained in position hands-free. Optionally, the ultrasound transducer 766 aligned with the needle trajectory may comprise a needle guide 765 through which a percutaneous device may be inserted.

Medial Protection

Nerve structures (e.g., vagus, sympathetic, hypoglossal nerves) that should be preserved or protected from injury may be positioned near a target ablation site. These nerve structures may commonly be located at or near a medial aspect of an intercarotid septum. These nerves may include the following:

Vagus Nerve Bundle—The vagus is a bundle of nerves that carry separate functions, for example a) bronchial motor neurons (efferent special visceral) which are responsible for swallowing and phonation and are distributed to pharyngeal branches, superior and inferior laryngeal nerves; b) visceral motor (efferent general visceral) which are responsible for involuntary muscle and gland control and are distributed to cardiac, pulmonary, esophageal, gastric, celiac plexuses, and muscles, and glands of the digestive tract; c) visceral sensory (afferent general visceral) which are responsible for visceral sensibility and are distributed to cervical, thoracic, abdominal fibers, and carotid and aortic bodies; d) visceral sensory (afferent special visceral) which are responsible for taste and are distributed to epiglottis and taste buds; e) general sensory (afferent general somatic) which are responsible for cutaneous sensibility and are distributed to auricular branch to external ear, meatus, and tympanic membrane. Dysfunction of the vagus may be detected by a) vocal changes caused by nerve damage (damage to the vagus nerve can result in trouble with moving the tongue while speaking, or hoarseness of the voice if the branch leading to the larynx is damaged); b) dysphagia due to nerve damage (the vagus nerve controls many muscles in the palate and tongue which, if damaged, can cause difficulty with swallowing); c) changes in gag reflex (the gag reflex is controlled by the vagus nerve and damage may cause this reflex to be lost, which can increase the risk of choking on saliva or food); d) cardiovascular problems due to nerve damage (damage to the vagus nerve can cause cardiovascular side effects including irregular heartbeat and arrhythmia); or e) digestive problems due to nerve damage (damage to the vagus nerve may cause problems with contractions of the stomach and intestines, which can lead to constipation).

Superior Laryngeal Nerve—the superior laryngeal nerve is a branch of the vagus nerve bundle. Functionally, the superior laryngeal nerve function can be divided into sensory and motor components. The sensory function provides a variety of afferent signals from the supraglottic larynx. Motor function involves motor supply to the ipsilateral cricothyroid muscle. Contraction of the cricothyroid muscle tilts the cricoid lamina backward at the cricothyroid joint causing lengthening, tensing and adduction of vocal folds causing an increase in the pitch of the voice generated. Dysfunction of the superior laryngeal nerve may change the pitch of the voice and causes an inability to make explosive sounds. A bilateral palsy presents as a tiring and hoarse voice.

Cervical Sympathetic Nerve—The cervical sympathetic nerve provides efferent fibers to the internal carotid nerve, external carotid nerve, and superior cervical cardiac nerve. It provides sympathetic innervation of the head, neck and heart. Organs that are innervated by the sympathetic nerves include eyes, lacrimal gland and salivary glands. Dysfunction of the cervical sympathetic nerve includes Horner's syndrome, which is very identifiable and may include the following reactions: a) partial ptosis (drooping of the upper eyelid from loss of sympathetic innervation to the superior tarsal muscle, also known as Müller's muscle); b) upside-down ptosis (slight elevation of the lower lid); c) anhidrosis (decreased sweating on the affected side of the face); d) miosis (small pupils, for example small relative to what would be expected by the amount of light the pupil receives or constriction of the pupil to a diameter of less than two millimeters, or asymmetric, one-sided constriction of pupils); e) enophthalmos (an impression that an eye is sunken in); f) loss of ciliospinal reflex (the ciliospinal reflex, or pupillary-skin reflex, consists of dilation of the ipsilateral pupil in response to pain applied to the neck, face, and upper trunk. If the right side of the neck is subjected to a painful stimulus, the right pupil dilates about 1-2 mm from baseline. This reflex is absent in Horner's syndrome and lesions involving the cervical sympathetic fibers.)

A percutaneous ablation device may comprise a protective element and an ablative element. For example, a device may comprise an ablative element that delivers an ablative heating energy (e.g., radiofrequency, microwave, ultrasound, low frequency ultrasound, high intensity focused ultrasound) and a protective element that impedes a heating effect such as a cooling element (e.g., cool fluid injection, Joule-Thompson expansion chamber, cryogen phase change expansion chamber, Peltier element) that maintains tissue such as vital nerves in a non-ablative temperature range. Conversely, a device with a cryo-ablation element may comprise a protective element that warms tissue (e.g., RF electrode, ultrasound transducer, resistive heating element). A protective element may be positioned at a distal tip of a percutaneous device shaft while an ablation element is proximal to the protection element. Such a device may be inserted with an anterior approach and advanced into an intercarotid septum such that a protective element is positioned at a medial aspect of the septum or on a medial side of a carotid sheath and an ablation element is positioned within the septum or towards a lateral aspect of the septum.

Figure 39:
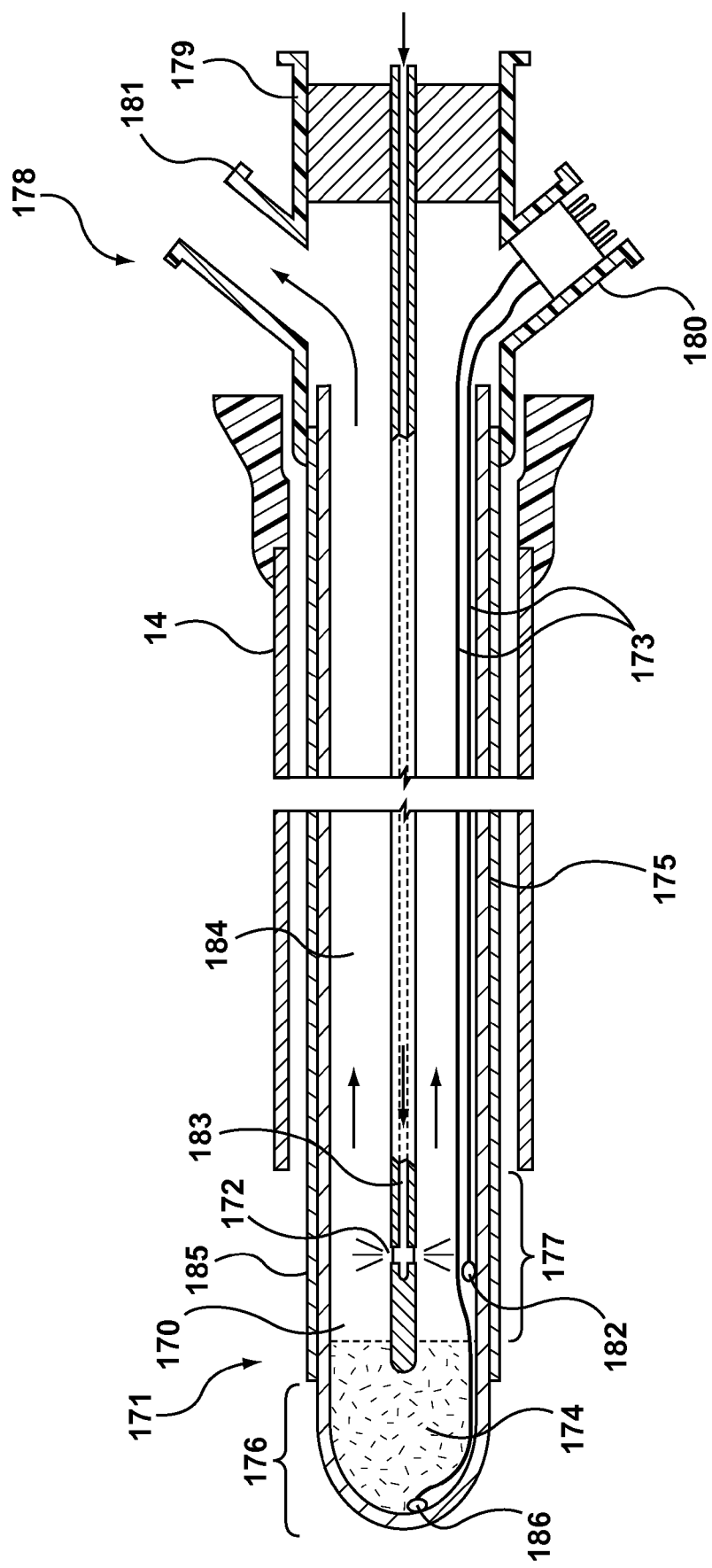
FIG. 39 depicts a Two Zone Percutaneous Cryo Ablation probe.

FIG. 39 depicts a Two Zone Percutaneous Cryo Ablation probe (TZPCA) 171. Probe 171 includes both an ablation element and a protection element. In this embodiment TZPCA probe 171 is configured to cryo-ablate a carotid body by percutaneous access, and to protect nervous structures from cold injury distal to the tip of the probe using a distal warming means. TZPCA probe 171 is an elongated structure comprising a shaft 175, a distal region comprising a protection element which in this embodiment is a warming element 176, and proximal to warming element 176 is an ablation element which is this embodiment is a cryo-ablation element 177, and a proximal terminal 178, which may comprise cryogen supply connector 179, electrical connector 180, and cryogen return gas connector 181 (alternatively, cryogen return gas connector may be omitted and gas may be exhausted to atmosphere). Shaft 175 may be a rigid metallic structure fabricated from a stainless steel hypo tube or rigid polymer, or may be a hollow flexible structure fabricated from a polymer. Shaft 175 has a caliber suitable for insertion though a percutaneous cannula with an outer diameter between 1 mm and 2 mm, and a length between 3 cm and 20 cm long (e.g., between about 8 cm and 10 cm long). As depicted, shaft 175 is a stainless steel hypo-tube with a rounded distal tip. The cryoablation element 177 may comprise an expansion/evaporation chamber 170, a temperature sensor 182, and a cryogen supply tube 183 in communication with cryogen supply connector 179 with cryogen gas exhausting the probe through an exhaust lumen 184 which may be connected to return cryogen gas connector 181 or exhausted to atmosphere. Cryogen supply tube 183 may have exit lumens 172 that allow cryogen to escape the supply lumen 183 into the expansion chamber 170 directed toward the sides of the inner wall of the cryo-ablation element 177. Warming element 176 may be formed by configuring the distal tip as an RF warming electrode. A material with low thermal conductance such as silicone 174 may be positioned between the cryo-ablation element and the warming element to reduce thermal conduction. The warming element electrode may be formed by coating shaft 175 with an electrically insulative coating 185 (e.g., PET, or Polyimide) except at the distal tip as shown, and electrically connecting shaft 175 to a source of radiofrequency (RF) energy. If RF energy is used to warm tissue proximate the warming element 176 a dispersive electrode may be placed on a patient's skin to complete the RF circuit. In addition, a temperature sensor 186 is mounted in thermal association with the uncoated warming element electrode 176. Shaft 175, cryo-ablation temperature sensor 182, and warming element temperature sensor 186 are connected to electrical connector 180 by wires 173 running though a channel of shaft 175 and proximal terminal 178. The distal heating element may be configured to heat by alternate energy means including ultrasonic, low frequency ultrasound, high intensity focused ultrasound, laser, microwave energy, or by a resistive heating element.

In alternative embodiments the ablation element of probe 171 is an ablation element configured to ablate tissue via heating (e.g., via RF energy, laser, microwave, etc.) and the protection element is configured to protect nerve structures from heat injury (e.g., by cooling tissue). For example, the protection element could be a cryo-element.

Figure 40:
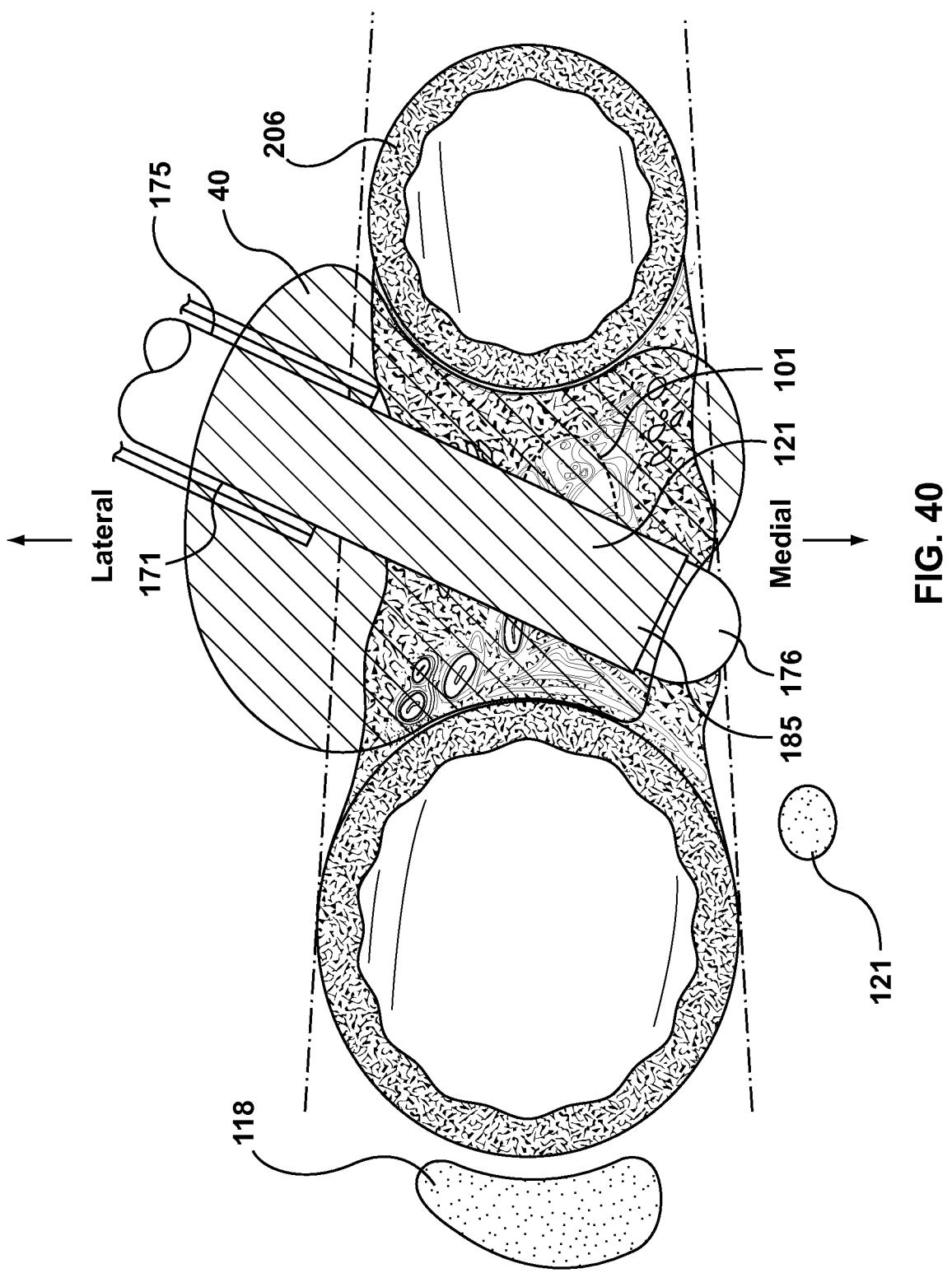
FIG. 40 is a sectional view of a Two Zone Percutaneous Cryo Ablation probe during a cryo ablation, where a warming element is protecting a sympathetic nerve from cold injury by preventing frozen tissue from expanding in a distal direction.

FIG. 40 is a sectional view of a TZCPA probe during a cryo ablation, where a warming element 176 is protecting sympathetic nerve 121 from cold injury by preventing frozen tissue 40 from expanding in direction distal of the probe. For example, frozen tissue 40 may be cooled to a cryo-ablative temperature (e.g., −40 degrees C. or lower) while the warming element may prevent cryo ablative temperature from spreading in a distal direction. The warming element may allow tissue distal to the cryo-ablation element to remain above, for example −40 degrees C. (e.g., above −20 degrees C., or above 0 degrees C.).

Alternatively, protection of vital nerve structures may be accomplished with a device that delivers protective energy that is separate from an ablation device. For example, an ablation device may be a percutaneous cryo-ablation probe that cools a target ablation site to an ablative temperature and a protection device may be an externally applied ultrasound transducer that delivers ultrasound energy that selectively warms nerve tissue (e.g., due to resonance with elasticity of nerve fibers) thus impeding nerves in a vicinity of the target ablation site from cooling to an ablative temperature. Externally applied, non-invasive ultrasound heating may be focused at a desired region (e.g., around or medial to a target ablation site) by targeting a fiducial (e.g., a distal tip of a percutaneous ablation probe) or a Doppler signal from blood flow to target a specific location within the body and can then be applied from outside the body to heat that specific target. Doppler may be used to identify the internal and external carotid arteries or the carotid bifurcation as landmarks and ultrasound energy may be focused at a desired area relative to these landmarks. This technology could be used to heat a medial side of a carotid bifurcation as the carotid septum is ablated with cryo energy (e.g., using an endovascular or percutaneous cryo-ablation device). The ultrasonic heating may be applied to protect non-target tissue or structures from cryo-ablation yet create mild heating so as to not ablate or injure the tissue or structures.

It is also possible to use a separate device or multiple separate devices to inject cold fluid to the area medial to a target ablation site while ablating the target with a percutaneous approach. This may be advantageous because another injection approach may supply a more favorable path to the medial side of the carotid bifurcation. The injection of protective cold fluid could also be completed through an endovascular approach while the ablation is completed with a percutaneous approach. An endovascular needle at a tip of a catheter or other tool, could be used to inject cold fluid while a percutaneous needle or other tool is used to ablate the carotid body percutaneously. Conversely, while a target ablation site is ablated with cryo energy, tissue medial to the target ablation site could be heated with RF energy. This could be done using either a different element of the same device or a separate device. The RF energy could be applied in the medial direction from either an internal, external, or common carotid artery. Thermal protection could be at low enough levels that nerves and tissue would not be ablated or injured, but would only serve to create a barrier against cryo-ablation energy. The RF electrode could be configured in a single point design or in a basket or balloon design with multiple electrodes.

Figure 41:
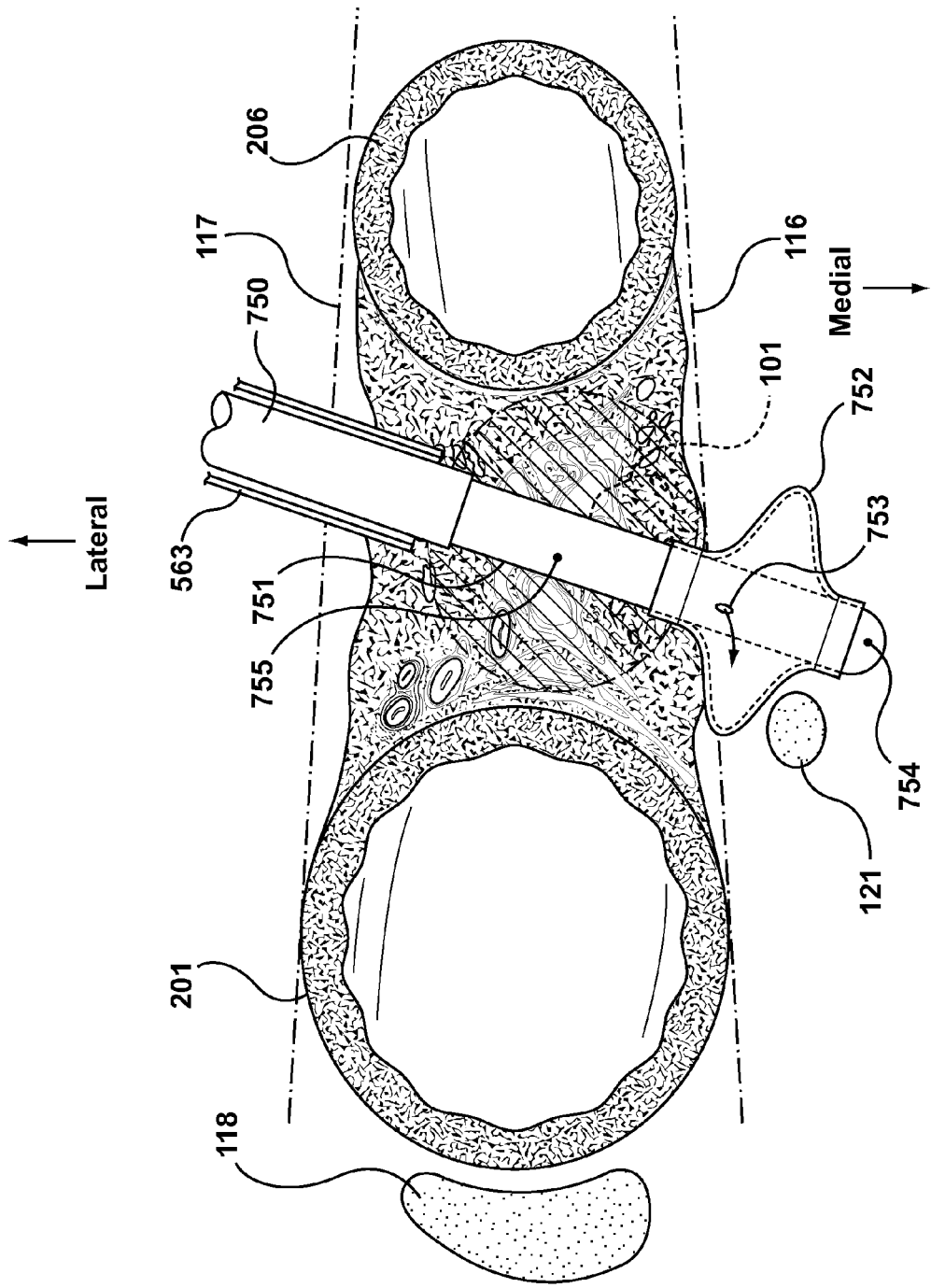
FIG. 41 is a schematic illustration of a percutaneous ablation device having a deployable structure for protection of structures of a medial aspect of an intercarotid septum.

An alternative embodiment for protection of a medial aspect of an intercarotid septum during ablation of the septum involves creating a greater distance between tissue of the medial aspect and the target ablation site. As shown in FIG. 41 a percutaneous ablation device 750 may comprise an ablation element 751 (e.g., radiofrequency electrode, cryogenic applicator, ultrasound transducer, microwave antennae) and an expandable structure 752 distal to the ablation element. The expandable structure 752 may be for example a balloon, which may be deployed by injecting a liquid such as saline through an inflation port 753 that is in fluid communication with a lumen in the device 750. The inflation liquid may further facilitate thermal protection by creating a heat sink. A temperature sensor 754 such as a thermocouple may be positioned on the device 750 distal to the expandable structure 752 to monitor temperature of the protected zone. A temperature sensor 755 may also be positioned proximate the ablation element to monitor ablation temperature. An ablation console external to the patient (not shown) may deliver ablation energy (e.g., radiofrequency electrical current) to the ablation element 751 according to a computer algorithm that monitors ablation temperature with temperature sensor 755 and protection temperature with temperature sensor 754. The expandable structure 752 may shield the protected area from conduction of ablative energy and may move the protected area further from the target ablation site separating it from a zone of ablation. Alternative embodiments of expandable structures may include a deployable mesh or wire cage. A stimulation electrode may be positioned distal to an expandable structure, which may be used to deliver a nerve stimulation signal to confirm that nerves to be protected from ablation are distal to the expandable structure 752.

Figure 42:
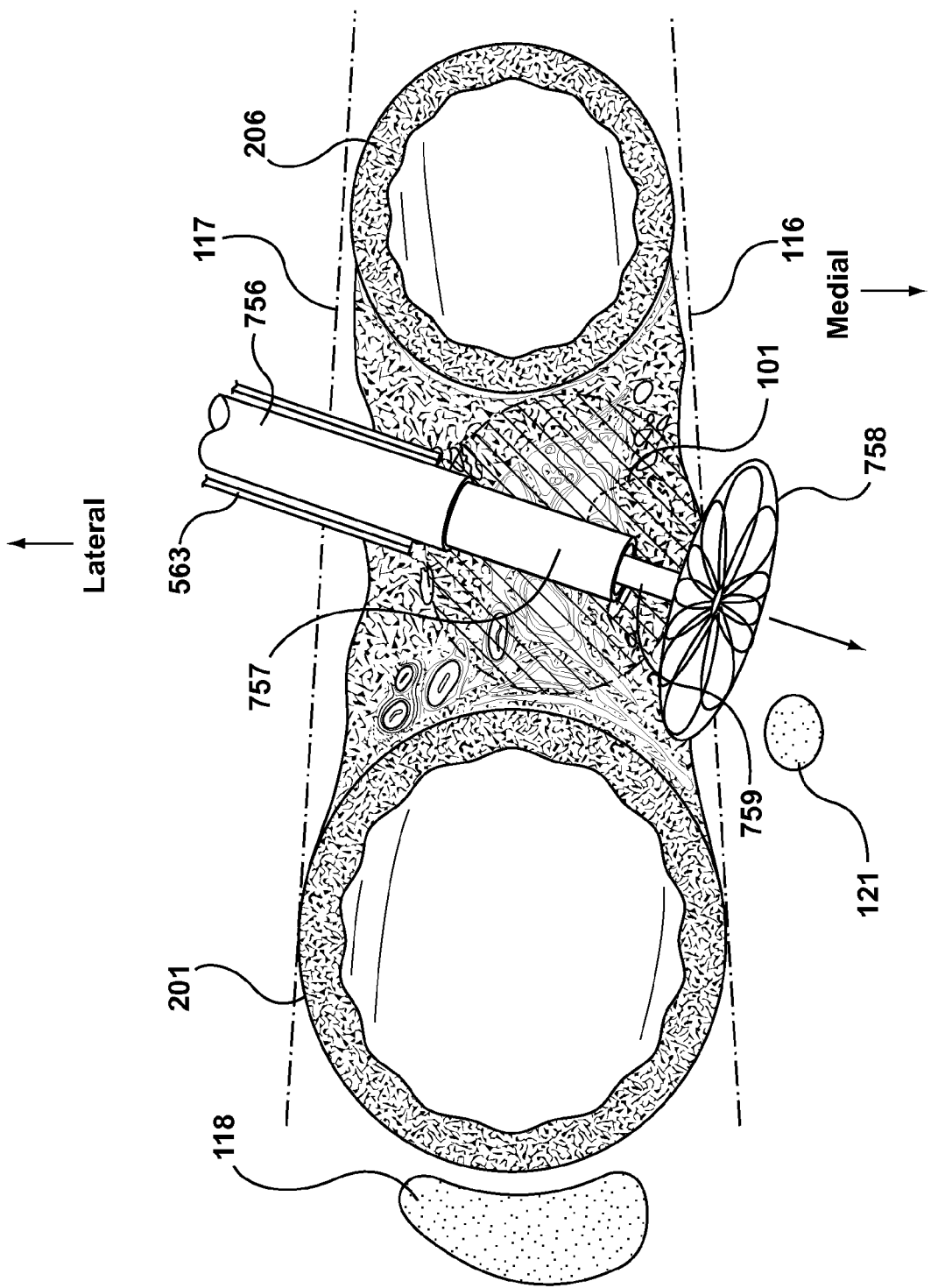
FIG. 42 is a schematic illustration of a percutaneous ablation device having a telescopic deployable structure for protection of structures of a medial aspect of an intercarotid septum.

FIG. 42 is a schematic illustration of a percutaneous ablation device 756 delivered through a cannula 563. The ablation device 756 comprises an ablation element 757 (e.g., radiofrequency electrode) and an expandable element 758 mounted to a shaft 759 that is telescopically advanced from a lumen of the device 756. The expandable element may be, for example, a superelastic umbrella-like Nitinol structure that is deployed when advanced out of the lumen and retracted when pulled back into the lumen. Telescopically advancing the expandable structure 758 from the lumen may move tissue distal to the structure 758 away from the ablation element 757 thus protecting it from an ablation zone created around the ablation element 757.

Methods of Therapy:

An endovascular approach may be an alternative to a percutaneous carotid body ablation. However, there may be danger of creating a brain embolism while performing an endovascular procedure in a patient's carotid artery, for example, a thrombus may be created by delivering ablation energy such as on a radiofrequency electrode, or a piece of atheromatous plaque may be dislodged by catheter movement. A percutaneous procedure may be favorable particularly in patients with a high risk of causing a brain embolism due to dislodging plaque.

Percutaneous ablation devices may have various tip geometries or combinations thereof. For example, an introducer needle may have a sharp tip such as a beveled cut, pencil point, or trocar tip, which may facilitate advancement through skin and other tissue. The sharp tip may be removed from a cannula and replaced with a blunt tip to reduce risk of perforating or injuring a delicate structure such as a nerve or artery. A blunt tip may be used to physically contact an artery and provide tactile feedback to a user or to deform the artery providing visual confirmation on an imaging modality such as Doppler ultrasound imaging or CTA. Percutaneous ablation devices may have various diameters or combinations thereof. For example, a fine gauge needle such as a 22 GA or smaller needle may be advanced through tissue to a target site. Such a fine gauge may puncture an artery wall and be removed without causing bleeding. If the fine gauge needle inadvertently punctures an artery, which may be indicated by drawing blood, the needle may be repositioned until it is placed at a target site satisfactorily. A larger gauge percutaneous ablation device may be inserted over the fine gauge needle to the target site, thus decreasing a risk of puncturing an artery with the larger gauge needle, which may cause bleeding.

An energy field generator may be located external to the patient. Various types of energy generators or supplies, such as electrical frequency generators, ultrasonic generators, microwave generators, laser consoles, and heating or cryogenic fluid supplies, may be used to provide energy to the energy delivery element at the distal tip of a percutaneous ablation device. An electrode or other energy applicator at the distal tip of the percutaneous ablation device should conform to the type of energy generator coupled to the device. The generator may include computer controls to automatically or manually adjust frequency and strength of the energy applied to the device, timing and period during which energy is applied, and safety limits to the application of energy. It should be understood that embodiments of energy delivery electrodes described herein may be electrically connected to the generator even though the generator is not explicitly shown or described with each embodiment.

An ablated tissue lesion at or near the carotid body may be created by the application of thermal energy from an energy delivery element proximate to the distal end of the carotid body ablation device. The ablated tissue lesion may disable the carotid body or may suppress the activity of the carotid body or interrupt conduction of afferent nerve signals from a carotid body to sympathetic nervous system. The disabling or suppression of the carotid body reduces the responsiveness of the glomus cells to changes of blood gas composition and effectively reduces activity of afferent carotid body nerves or the chemoreflex gain of the patient.

A method in accordance with a particular embodiment includes ablating at least one of a patient's carotid bodies based at least in part on identifying the patient as having a sympathetically mediated disease such as cardiac, metabolic, or pulmonary disease such as hypertension, insulin resistance, diabetes, pulmonary hypertension, drug resistant hypertension (e.g., refractory hypertension), congestive heart failure (CHF), or dyspnea from heart failure or pulmonary disease causes.

A procedure may include diagnosis, selection based on diagnosis, further screening (e.g., baseline assessment of chemosensitivity), treating a patient based at least in part on diagnosis or further screening via a chemoreceptor (e.g., carotid body) ablation procedure such as one of the embodiments disclosed. Additionally, following ablation a method of therapy may involve conducting a post-ablation assessment to compare with the baseline assessment and making decisions based on the assessment (e.g., adjustment of drug therapy, re-treat in new position or with different parameters, or ablate a second chemoreceptor if only one was previously ablated).

A carotid body ablation procedure may comprise the following steps or a combination thereof: placing fiducial markers on a patient, placing a nock-positioning collar on a patient, patient sedation, locating a target peripheral chemoreceptor, visualizing a target site (e.g., peripheral chemoreceptor, carotid body, intercarotid septum, carotid nerves), overlaying preoperative images on perioperative images, confirming a target ablation site is or is proximate a peripheral chemoreceptor, confirming a target ablation site is safely distant from vital structures that are preferably protected (e.g., sympathetic, hypoglossal or vagus nerves), providing stimulation (e.g., electrical, mechanical, chemical) to a target site or target peripheral chemoreceptor prior to, during or following an ablation step, monitoring physiological responses to said stimulation, providing temporary cryogenic nerve block to a target site prior to an ablation step, monitoring physiological responses to said temporary nerve block, anesthetizing a target site, protecting the brain from potential embolism, thermally protecting an arterial or venous wall (e.g., carotid artery, jugular vein) or a medial aspect of an intercarotid septum or vital nerve structures, ablating a target site or peripheral chemoreceptor, monitoring ablation parameters (e.g., temperature, impedance, blood flow in a carotid artery), confirming a reduction of chemoreceptor activity (e.g., chemosensitivity, HR, blood pressure, ventilation, sympathetic nerve activity) during or following an ablation step, removing an ablation device, conducting a post-ablation assessment, repeating any steps of the chemoreceptor ablation procedure on another peripheral chemoreceptor in the patient.

Patient screening, as well as post-ablation assessment may include physiological tests or gathering of information, for example, chemoreflex sensitivity, central sympathetic nerve activity, heart rate, heart rate variability, blood pressure, ventilation, production of hormones, peripheral vascular resistance, blood pH, blood PCO2, degree of hyperventilation, peak VO2, VENCO2 slope. Directly measured maximum oxygen uptake (more correctly pVO2 in heart failure patients) and index of respiratory efficiency VENCO2 slope has been shown to be a reproducible marker of exercise tolerance in heart failure and provide objective and additional information regarding a patient's clinical status and prognosis.

A method of therapy may include electrical stimulation of a target region, using a stimulation electrode, to confirm proximity to a carotid body. For example, a stimulation signal having a 1-10 milliamps (mA) pulse train at about 20 to 40 Hz with a pulse duration of 50 to 500 microseconds (μs) that produces a positive carotid body stimulation effect may indicate that the stimulation electrode is within sufficient proximity to the carotid body or nerves of the carotid body to effectively ablate it. A positive carotid body stimulation effect could be increased blood pressure, heart rate, or ventilation concomitant with application of the stimulation. These variables could be monitored, recorded, or displayed to help assess confirmation of proximity to a carotid body. A percutaneous technique, for example, may have a stimulation electrode proximal to the energy delivery element used for ablation. Alternatively, the energy delivery element itself may also be used as a stimulation electrode. Alternatively, an energy delivery element that delivers a form of ablative energy that is not electrical, such as a cryogenic ablation applicator, may be configured to also deliver an electrical stimulation signal as described earlier. Yet another alternative embodiment comprises a stimulation electrode that is distinct from an ablation element. For example, during a surgical procedure a stimulation probe can be touched to a suspected carotid body that is surgically exposed. A positive carotid body stimulation effect could confirm that the suspected structure is a carotid body and ablation can commence. Physiological monitors (e.g., heart rate monitor, blood pressure monitor, blood flow monitor, MSNA monitor) may communicate with a computerized stimulation generator, which may also be an ablation generator, to provide feedback information in response to stimulation. If a physiological response correlates to a given stimulation the computerized generator may provide an indication of a positive confirmation.

Alternatively or in addition a drug known to excite the chemo sensitive cells of the carotid body can be injected directly into the carotid artery or given systemically into patients vein or artery in order to elicit hemodynamic or respiratory response. Examples of drugs that may excite a chemoreceptor include nicotine, atropine, Doxapram, Almitrine, hyperkalemia, Theophylline, adenosine, sulfides, Lobeline, Acetylcholine, ammonium chloride, methylamine, potassium chloride, anabasine, coniine, cytosine, acetaldehyde, acetyl ester and the ethyl ether of i-methylcholine, Succinylcholine, Piperidine, monophenol ester of homo-isomuscarine and acetylsalicylamides, alkaloids of veratrum, sodium citrate, adenosinetriphosphate, dinitrophenol, caffeine, theobromine, ethyl alcohol, ether, chloroform, phenyldiguanide, sparteine, coramine (nikethamide), metrazol (pentylenetetrazol), iodomethylate of dimethylaminomethylenedioxypropane, ethyltrimethylammoniumpropane, trimethylammonium, hydroxytryptamine, papaverine, neostigmine, acidity.

A method of therapy may further comprise applying electrical or chemical stimulation to the target area or systemically following ablation to confirm a successful ablation. Heart rate, blood pressure or ventilation may be monitored for change or compared to the reaction to stimulation prior to ablation to assess if the targeted carotid body was ablated. Post-ablation stimulation may be done with the same apparatus used to conduct the pre-ablation stimulation. Physiological monitors (e.g., heart rate monitor, blood pressure monitor, blood flow monitor, MSNA monitor) may communicate with a computerized stimulation generator, which may also be an ablation generator, to provide feedback information in response to stimulation. If a physiological response correlated to a given stimulation is reduced following an ablation compared to a physiological response prior to the ablation, the computerized generator may provide an indication ablation efficacy or possible procedural suggestions such as repeating an ablation, adjusting ablation parameters, changing position, ablating another carotid body or chemosensor, or concluding the procedure.

Visualization:

An optional step of visualizing internal structures (e.g., carotid body or surrounding structures) may be accomplished using one or more non-invasive imaging modalities, for example fluoroscopy, radiography, arteriography, computer tomography (CT), computer tomography angiography with contrast (CTA), magnetic resonance imaging (MRI), or sonography (e.g., single or bi-plane sonography), or minimally invasive techniques (e.g., IVUS, endoscopy, optical coherence tomography, ICE). A visualization step may be performed as part of a patient assessment, prior to an ablation procedure to assess risks and location of anatomical structures or help to plan an ablation procedure, during an ablation procedure to help guide an ablation device, or following an ablation procedure to assess outcome (e.g., efficacy of the ablation). Visualization may be used to: (a) locate a carotid body, (b) locate vital structures that may be adversely affected, or (c) locate, identify and measure arterial plaque.

Endovascular (for example transfemoral) arteriography of the common carotid and then selective arteriography of the internal and external carotids may be used to facilitate visualization of a carotid bifurcation during a percutaneous carotid body ablation procedure. Additionally, ostia of glomic arteries (these arteries may be up to 4 mm long and arise directly from the main parent artery) can be identified by dragging the dye injection catheter and releasing small amounts ("puffs") of dye. Direct injection of dye into glomic arteries can further assist the interventionalist in the ablation procedure. It is appreciated that the feeding glomic arteries are small and microcatheters may be needed to cannulate them.

Ultrasound visualization may allow a physician to see the carotid arteries and even the carotid body. Another method for visualization may consist of inserting a small needle (e.g., 22 Gauge) with sonography or computer tomography (CT) guidance into or toward the carotid body. A wire or needle can be left in place as a fiducial guide, or contrast can be injected into the carotid body. Runoff of contrast to the jugular vein may confirm that the target is achieved.

Computer Tomography (CT) and computer tomography angiography (CTA) may also be used to aid in identifying a carotid body. Such imaging could be used to help guide an ablation device to a carotid body.

Ultrasound visualization (e.g., sonography) is an ultrasound-based imaging technique used for visualizing subcutaneous body structures including blood vessels and surrounding tissues. Doppler ultrasound uses reflected ultrasound waves to identify and display blood flow through a vessel. Operators typically use a hand-held transducer/transceiver placed directly on a patient's skin and aimed inward directing ultrasound waves through the patient's tissue. Ultrasound may be used to visualize a patient's carotid body to help guide an ablation device. Ultrasound can be also used to identify atherosclerotic plaque in the carotid arteries and avoid disturbing and dislodging such plaque.

Visualization and navigation steps may comprise multiple imaging modalities (e.g., CT, fluoroscopy, ultrasound) superimposed digitally to use as a map for instrument positioning. Superimposing borders of great vessels such as carotid arteries can be done to combine images.

Responses to stimulation at different coordinate points can be stored digitally as a 3-dimensional or 2-dimenisional orthogonal plane map. Such an electric map of the carotid bifurcation showing points, or point coordinates that are electrically excitable such as baroreceptors, baroreceptor nerves, chemoreceptors and chemoreceptor nerves can be superimposed with an image (e.g., CT, fluoroscopy, ultrasound) of vessels. This can be used to guide the procedure, and identify target areas and areas to avoid.

In addition, as noted above, it should be understood that a device providing therapy can also be used to locate a carotid body as well as to provide various stimuli (electrical, chemical, other) to test a baseline response of the carotid body chemoreflex (CBC) or carotid sinus baroreflex (CSB) and measure changes in these responses after therapy or a need for additional therapy to achieve the desired physiological and clinical effects.

Patient Selection and Assessment:

In an embodiment, a procedure may comprise assessing a patient to be a plausible candidate for carotid body ablation. Such assessment may involve diagnosing a patient with a sympathetically mediated disease (e.g., MSNA microneurography, measure of cataclomines in blood or urine, heart rate, or low/high frequency analysis of heart rate variability may be used to assess sympathetic tone). Patient assessment may further comprise other patient selection criteria, for example indices of high carotid body activity (i.e., carotid body hypersensitivity or hyperactivity) such as a combination of hyperventilation and hypocarbia at rest, high carotid body nerve activity (e.g., measured directly), incidence of periodic breathing, dyspnea, central sleep apnea elevated brain natriuretic peptide, low exercise capacity, having cardiac resynchronization therapy, atrial fibrillation, ejection fraction of the left ventricle, using beta blockers or ACE inhibitors.

Patient assessment may further involve selecting patients with high peripheral chemosensitivity (e.g., a respiratory response to hypoxia normalized to the desaturation of oxygen greater than or equal to about 0.7 l/min/min $SpO_2$), which may involve characterizing a patient's chemoreceptor sensitivity, reaction to temporarily blocking carotid body chemoreflex, or a combination thereof.

Although there are many ways to measure chemosensitivity they can be divided into (a) active provoked response and (b) passive monitoring. Active tests can be done by inducing intermittent hypoxia (such as by taking breaths of nitrogen or $CO_2$ or combination of gases) or by rebreathing air into and from a 4 to 10 liter bag. For example: a hypersensitive response to a short period of hypoxia measured by increase of respiration or heart rate may provide an indication for therapy. Ablation or significant reduction of such response could be indicative of a successful procedure. Also, electrical stimulation, drugs and chemicals (e.g., dopamine, lidocane) exist that can block or excite a carotid body when applied locally or intravenously.

The location and baseline function of the desired area of therapy (including the carotid and aortic chemoreceptors and baroreceptors and corresponding nerves) may be determined prior to therapy by application of stimuli to the carotid body or other organs that would result in an expected change in a physiological or clinical event such as an increase or decrease in SNS activity, heart rate or blood pressure. These stimuli may also be applied after the therapy to determine the effect of the therapy or to indicate the need for repeated application of therapy to achieve the desired physiological or clinical effect(s). The stimuli can be either electrical or chemical in nature and can be delivered via the same or another device or can be delivered separately (such as injection of a substance through a peripheral IV to affect the CBC that would be expected to cause a predicted physiological or clinical effect).

A baseline stimulation test may be performed to select patients that may benefit from a carotid body ablation procedure. For example, patients with a high peripheral chemosensitivity gain (e.g., greater than or equal to about two standard deviations above an age matched general population chemosensitivity, or alternatively above a threshold peripheral chemosensitivity to hypoxia of 0.5 or 0.7 ml/min % O2) may be selected for a carotid body ablation procedure. A prospective patient suffering from a cardiac, metabolic, or pulmonary disease (e.g., hypertension, CHF, diabetes) may be selected. The patient may then be tested to assess a baseline peripheral chemoreceptor sensitivity (e.g., minute ventilation, tidal volume, ventilator rate, heart rate, or other response to hypoxic or hypercapnic stimulus). Baseline peripheral chemosensitivity may be assessed using tests known in the art which involve inhalation of a gas mixture having reduced $O_2$ content (e.g., pure nitrogen, $CO_2$, helium, or breathable gas mixture with reduced amounts of $O_2$ and increased amounts of $CO_2$) or rebreathing of gas into a bag. Concurrently, the patient's minute ventilation or initial sympathetically mediated physiologic parameter such as minute ventilation or HR may be measured and compared to the $O_2$ level in the gas mixture. Tests like this may elucidate indices called chemoreceptor setpoint and gain. These indices are indicative of chemoreceptor sensitivity. If the patient's chemosensitivity is not assessed to be high (e.g., less than about two standard deviations of an age matched general population chemosensitivity, or other relevant numeric threshold) then the patient may not be a suitable candidate for a carotid body ablation procedure. Conversely, a patient with chemoreceptor hypersensitivity (e.g., greater than or equal to about two standard deviations above normal) may proceed to have a carotid body ablation procedure. Following a carotid body ablation procedure the patient's chemosensitivity may optionally be tested again and compared to the results of the baseline test. The second test or the comparison of the second test to the baseline test may provide an indication of treatment success or suggest further intervention such as possible adjustment of drug therapy, repeating the carotid body ablation procedure with adjusted parameters or location, or performing another carotid body ablation procedure on a second carotid body if the first procedure only targeted one carotid body. It may be expected that a patient having chemoreceptor hypersensitivity or hyperactivity may return to about a normal sensitivity or activity following a successful carotid body ablation procedure.

In an alternative protocol for selecting a patient for a carotid body ablation, patients with high peripheral chemosensitivity or carotid body activity (e.g., ≥about 2 standard deviations above normal) alone or in combination with other clinical and physiologic parameters may be particularly good candidates for carotid body ablation therapy if they further respond positively to temporary blocking of carotid body activity. A prospective patient suffering from a cardiac, metabolic, or pulmonary disease may be selected to be tested to assess the baseline peripheral chemoreceptor sensitivity. A patient without high chemosensitivity may not be a plausible candidate for a carotid body ablation procedure. A patient with a high chemosensitivity may be given a further assessment that temporarily blocks a carotid body chemoreflex. For example a temporary block may be done chemically, for example using a chemical such as intravascular dopamine or dopamine-like substances, intravascular alpha-2 adrenergic agonists, oxygen, in general alkalinity, or local or topical application of atropine externally to the carotid body. A patient having a negative response to the temporary carotid body block test (e.g., sympathetic activity index such as respiration, BR, heart rate variability, MSNA, vasculature resistance, etc. is not significantly altered) may be a less plausible candidate for a carotid body ablation procedure. Conversely, a patient with a positive response to the temporary carotid body block test (e.g., respiration or index of sympathetic activity is altered significantly) may be a more plausible candidate for a carotid body ablation procedure.

There are a number of potential ways to conduct a temporary carotid body block test. Hyperoxia (e.g., higher than normal levels of $PO_2$) for example, is known to partially block (about a 50%) or reduce afferent sympathetic response of the carotid body. Thus, if a patient's sympathetic activity indexes (e.g., respiration, HR, HRV, MSNA) are reduced by hyperoxia (e.g., inhalation of higher than normal levels of $O_2$) for 3-5 minutes, the patient may be a particularly plausible candidate for carotid body ablation therapy. A sympathetic response to hyperoxia may be achieved by monitoring minute ventilation (e.g., reduction of more than 20-30% may indicate that a patient has carotid body hyperactivity). To evoke a carotid body response, or compare it to carotid body response in normoxic conditions, $CO_2$ above 3-4% may be mixed into the gas inspired by the patient (nitrogen content will be reduced) or another pharmacological agent can be used to invoke a carotid body response to a change of $CO_2$, pH or glucose concentration. Alternatively, "withdrawal of hypoxic drive" to rest state respiration in response to breathing a high concentration $O_2$ gas mix may be used for a simpler test.

An alternative temporary carotid body block test involves administering a sub-anesthetic amount of anesthetic gas halothane, which is known to temporarily suppress carotid body activity. Furthermore, there are injectable substances such as dopamine that are known to reversibly inhibit the carotid body. However, any substance, whether inhaled, injected or delivered by another manner to the carotid body that affects carotid body function in the desired fashion may be used.

Another alternative temporary carotid body block test involves application of cryogenic energy to a carotid body (i.e., removal of heat). For example, a carotid body or its nerves may be cooled to a temperature range between about −15° C. to 0° C. to temporarily reduce nerve activity or blood flow to and from a carotid body thus reducing or inhibiting carotid body activity.

An alternative method of assessing a temporary carotid body block test may involve measuring pulse pressure. Non-invasive pulse pressure devices such as Nexfin (made by BMEYE, based in Amsterdam, The Netherlands) can be used to track beat-to-beat changes in peripheral vascular resistance. Patients with hypertension or CHF may be sensitive to temporary carotid body blocking with oxygen or injection of a blocking drug. The peripheral vascular resistance of such patients may be expected to reduce substantially in response to carotid body blocking. Such patients may be good candidates for carotid body ablation therapy.

Yet another index that may be used to assess if a patient may be a good candidate for carotid body ablation therapy is increase of baroreflex, or baroreceptor sensitivity, in response to carotid body blocking. It is known that hyperactive chemosensitivity suppresses baroreflex. If carotid body activity is temporarily reduced the carotid sinus baroreflex (baroreflex sensitivity (BRS) or baroreflex gain) may be expected to increase. Baroreflex contributes a beneficial parasympathetic component to autonomic drive. Depressed BRS is often associated with an increased incidence of death and malignant ventricular arrhythmias. Baroreflex is measurable using standard non-invasive methods. One example is spectral analysis of RR interval of ECG and systolic blood pressure variability in both the high- and low-frequency bands. An increase of baroreflex gain in response to temporary blockade of carotid body can be a good indication for permanent therapy. Baroreflex sensitivity can also be measured by heart rate response to a transient rise in blood pressure induced by injection of phenylephrine.

An alternative method involves using an index of glucose tolerance to select patients and determine the results of carotid body blocking or removal in diabetic patients. There is evidence that carotid body hyperactivity contributes to progression and severity of metabolic disease.

In general, a beneficial response can be seen as an increase of parasympathetic or decrease of sympathetic tone in the overall autonomic balance. For example, Power Spectral Density (PSD) curves of respiration or HR can be calculated using nonparametric Fast Fourier Transform algorithm (FFT). FFT parameters can be set to 256-64 k buffer size, Hamming window, 50% overlap, 0 to 0.5 or 0.1 to 1.0 Hz range. HR and respiratory signals can be analyzed for the same periods of time corresponding to (1) normal unblocked carotid body breathing and (2) breathing with blocked carotid body.

Power can be calculated for three bands: the very low frequency (VLF) between 0 and 0.04 Hz, the low frequency band (LF) between 0.04-0.15 Hz and the high frequency band (HF) between 0.15-0.4 Hz. Cumulative spectral power in LF and HF bands may also be calculated; normalized to total power between 0.04 and 0.4 Hz (TF=HF+LF) and expressed as % of total. Natural breathing rate of CHF patient, for example, can be rather high, in the 0.3-0.4 Hz range.

The VLF band may be assumed to reflect periodic breathing frequency (typically 0.016 Hz) that can be present in CHF patients. It can be excluded from the HF/LF power ratio calculations.

The powers of the LF and HF oscillations characterizing heart rate variability (HRV) appear to reflect, in their reciprocal relationship, changes in the state of the sympathovagal (sympathetic to parasympathetic) balance occurring during numerous physiological and pathophysiological conditions. Thus, increase of HF contribution in particular can be considered a positive response to carotid body blocking.

Another alternative method of assessing carotid body activity comprises nuclear medicine scanning, for example with ocretide, somatostatin analogues, or other substances produced or bound by the carotid body.

Furthermore, artificially increasing blood flow may reduce carotid body activation. Conversely artificially reducing blood flow may stimulate carotid body activation. This may be achieved with drugs known in the art to alter blood flow.

There is a considerable amount of scientific evidence to demonstrate that hypertrophy of a carotid body often accompanies disease. A hypertrophied (i.e., enlarged) carotid body may further contribute to the disease. Thus identification of patients with enlarged carotid bodies may be instrumental in determining candidates for therapy. Imaging of a carotid body may be accomplished by angiography performed with radiographic, computer tomography, or magnetic resonance imaging.

It should be understood that the available measurements are not limited to those described above. It may be possible to use any single or a combination of measurements that reflect any clinical or physiological parameter effected or changed by either increases or decreases in carotid body function to evaluate the baseline state, or change in state, of a patient's chemosensitivity.

There is a considerable amount of scientific evidence to demonstrate that hypertrophy of a carotid body often accompanies disease. A hypertrophied or enlarged carotid body may further contribute to the disease. Thus identification of patients with enlarged carotid bodies may be instrumental in determining candidates for therapy.

Further, it is possible that although patients do not meet a preselected clinical or physiological definition of high peripheral chemosensitivity (e.g., greater than or equal to about two standard deviations above normal), administration of a substance that suppresses peripheral chemosensitivity may be an alternative method of identifying a patient who is a candidate for the proposed therapy. These patients may have a different physiology or co-morbid disease state that, in concert with a higher than normal peripheral chemosensitivity (e.g., greater than or equal to normal and less than or equal to about 2 standard deviations above normal), may still allow the patient to benefit from carotid body ablation. The proposed therapy may be at least in part based on an objective that carotid body ablation will result in a clinically significant or clinically beneficial change in the patient's physiological or clinical course. It is reasonable to believe that if the desired clinical or physiological changes occur even in the absence of meeting the predefined screening criteria, then therapy could be performed.

While the invention has been described in connection with what is presently considered to be the best mode, it is to be understood that the invention is not to be limited to the disclosed embodiment(s). The invention covers various modifications and equivalent arrangements included within the spirit and scope of the appended claims.

Assessment of atheromatous plaque in a patient's carotid arteries may be done, for example using ultrasound, to assess if a patient is more suitable for an endovascular or percutaneous carotid body ablation procedure.

Overview:

Ablation of a peripheral chemoreceptor (e.g., carotid body or aortic body) via a percutaneous approach in patients having sympathetically mediated disease and augmented chemoreflex (e.g., high afferent nerve signaling from a carotid body to the central nervous system as in some cases indicated by high peripheral chemosensitivity) has been conceived to reduce peripheral chemosensitivity and reduce afferent signaling from peripheral chemoreceptors to the central nervous system. The expected reduction of chemoreflex activity and sensitivity to hypoxia and other stimuli such as blood flow, blood $CO_2$, glucose concentration or blood pH can directly reduce afferent signals from chemoreceptors and produce at least one beneficial effect such as the reduction of central sympathetic activation, reduction of the sensation of breathlessness (dyspnea), vasodilation, increase of exercise capacity, reduction of blood pressure, reduction of sodium and water retention, redistribution of blood volume to skeletal muscle, reduction of insulin resistance, reduction of hyperventilation, reduction of tachypnea, reduction of hypocapnia, increase of baroreflex and barosensitivity of baroreceptors, increase of vagal tone, or improve symptoms of a sympathetically mediated disease and may ultimately slow down the disease progression and extend life. It is understood that a sympathetically mediated disease that may be treated with carotid body ablation may comprise elevated sympathetic tone, an elevated sympathetic/parasympathetic activity ratio, autonomic imbalance primarily attributable to central sympathetic tone being abnormally or undesirably high, or heightened sympathetic tone at least partially attributable to afferent excitation traceable to hypersensitivity or hyperactivity of a peripheral chemoreceptor (e.g., carotid body). In some important clinical cases where baseline hypocapnia or tachypnea is present, reduction of hyperventilation and breathing rate may be expected. It is understood that hyperventilation in the context herein means respiration in excess of metabolic needs on the individual that generally leads to slight but significant hypocapnea (blood $CO_2$ partial pressure below normal of approximately 40 mmHg, for example in the range of 33 to 38 mmHg). Patients having CHF or hypertension concurrent with heightened peripheral chemoreflex activity and sensitivity often react as if their system was hypercapnic even if it is not. The reaction is to hyperventilate, a maladaptive attempt to rid the system of $CO_2$, thus overcompensating and creating a hypocapnic and alkalotic system. Some researchers attribute this hypersensitivity/hyperactivity of the carotid body to the direct effect of catecholamines, hormones circulating in excessive quantities in the blood stream of CHF patients. The procedure may be particularly useful to treat such patients who are hypocapnic and possibly alkalotic resulting from high tonic output from carotid bodies. Such patients are particularly predisposed to periodic breathing and central apnea hypopnea type events that cause arousal, disrupt sleep, cause intermittent hypoxia and are by themselves detrimental and difficult to treat.

It is appreciated that periodic breathing of Cheyne Stokes pattern occurs in patients during sleep, exercise and even at rest as a combination of central hypersensitivity to $CO_2$, peripheral chemosensitivity to $O_2$ and $CO_2$ and prolonged circulatory delay. All these parameters are often present in CHF patients that are at high risk of death. Thus, patients with hypocapnea, CHF, high chemosensitivity and prolonged circulatory delay, and specifically ones that exhibit periodic breathing at rest or during exercise or induced by hypoxia are likely beneficiaries of the proposed therapy.

Hyperventilation is defined as breathing in excess of a person's metabolic need at a given time and level of activity. Hyperventilation is more specifically defined as minute ventilation in excess of that needed to remove CO2 from blood in order to maintain blood $CO_2$ in the normal range (e.g., around 40 mmHg partial pressure). For example, patients with arterial blood $PCO_2$ in the range of 32-37 mmHg can be considered hypocapnic and in hyperventilation.

For the purpose of this disclosure hyperventilation is equivalent to abnormally low levels of carbon dioxide in the blood (e.g., hypocapnia, hypocapnea, or hypocarbia) caused by overbreathing. Hyperventilation is the opposite of hypoventilation (e.g., underventilation) that often occurs in patients with lung disease and results in high levels of carbon dioxide in the blood (e.g., hypercapnia or hypercarbia).

A low partial pressure of carbon dioxide in the blood causes alkalosis, because CO2 is acidic in solution and reduced CO2 makes blood pH more basic, leading to lowered plasma calcium ions and nerve and muscle excitability. This condition is undesirable in cardiac patients since it can increase probability of cardiac arrhythmias.

Alkalemia may be defined as abnormal alkalinity, or increased pH of the blood. Respiratory alkalosis is a state due to excess loss of carbon dioxide from the body, usually as a result of hyperventilation. Compensated alkalosis is a form in which compensatory mechanisms have returned the pH toward normal. For example, compensation can be achieved by increased excretion of bicarbonate by the kidneys.

Compensated alkalosis at rest can become uncompensated during exercise or as a result of other changes of metabolic balance. Thus the invented method is applicable to treatment of both uncompensated and compensated respiratory alkalosis.

Tachypnea means rapid breathing. For the purpose of this disclosure a breathing rate of about 6 to 16 breaths per minute at rest is considered normal but there is a known benefit to lower rate of breathing in cardiac patients. Reduction of tachypnea can be expected to reduce respiratory dead space, increase breathing efficiency, and increase parasympathetic tone.

Therapy Example: Role of Chemoreflex and Central Sympathetic Nerve Activity in CHF Chronic elevation in sympathetic nerve activity (SNA) is associated with the development and progression of certain types of hypertension and contributes to the progression of congestive heart failure (CHF). It is also known that sympathetic excitatory cardiac, somatic, and central/peripheral chemoreceptor reflexes are abnormally enhanced in CHF and hypertension (Ponikowski, 2011 and Giannoni, 2008 and 2009).

Arterial chemoreceptors serve an important regulatory role in the control of alveolar ventilation. They also exert a powerful influence on cardiovascular function.

Delivery of Oxygen ($O_2$) and removal of Carbon Dioxide ($CO_2$) in the human body is regulated by two control systems, behavioral control and metabolic control. The metabolic ventilatory control system drives our breathing at rest and ensures optimal cellular homeostasis with respect to pH, partial pressure of carbon dioxide ($PCO_2$), and partial pressure of oxygen ($PO_2$). Metabolic control uses two sets of chemoreceptors that provide a fine-tuning function: the central chemoreceptors located in the ventral medulla of the brain and the peripheral chemoreceptors such as the aortic chemoreceptors and the carotid body chemoreceptors. The carotid body, a small, ovoid-shaped (often described as a grain of rice), and highly vascularized organ is situated in or near the carotid bifurcation, where the common carotid artery branches in to an internal carotid artery (IC) and external carotid artery (EC). The central chemoreceptors are sensitive to hypercapnia (high $PCO_2$), and the peripheral chemoreceptors are sensitive to hypercapnia and hypoxia (low blood $PO_2$). Under normal conditions activation of the sensors by their respective stimuli results in quick ventilatory responses aimed at the restoration of cellular homeostasis.

As early as 1868, Pflüiger recognized that hypoxia stimulated ventilation, which spurred a search for the location of oxygen-sensitive receptors both within the brain and at various sites in the peripheral circulation. When Corneille Heymans and his colleagues observed that ventilation increased when the oxygen content of the blood flowing through the bifurcation of the common carotid artery was reduced (winning him the Nobel Prize in 1938), the search for the oxygen chemosensor responsible for the ventilatory response to hypoxia was largely considered accomplished.

The persistence of stimulatory effects of hypoxia in the absence (after surgical removal) of the carotid chemoreceptors (e.g., the carotid bodies) led other investigators, among them Julius Comroe, to ascribe hypoxic chemosensitivity to other sites, including both peripheral sites (e.g., aortic bodies) and central brain sites (e.g., hypothalamus, pons and rostral ventrolateral medulla). The aortic chemoreceptor, located in the aortic body, may also be an important chemoreceptor in humans with significant influence on vascular tone and cardiac function.

Carotid Body Chemoreflex:

The carotid body is a small cluster of chemoreceptors (also known as glomus cells) and supporting cells located near, and in most cases directly at, the medial side of the bifurcation (fork) of the carotid artery, which runs along both sides of the throat.

These organs act as sensors detecting different chemical stimuli from arterial blood and triggering an action potential in the afferent fibers that communicate this information to the Central Nervous System (CNS). In response, the CNS activates reflexes that control heart rate (HR), renal function and peripheral blood circulation to maintain the desired homeostasis of blood gases, $O_2$ and $CO_2$, and blood pH. This closed loop control function that involves blood gas chemoreceptors is known as the carotid body chemoreflex (CBC). The carotid body chemoreflex is integrated in the CNS with the carotid sinus baroreflex (CSB) that maintains arterial blood pressure. In a healthy organism these two reflexes maintain blood pressure and blood gases within a narrow physiologic range. Chemosensors and barosensors in the aortic arch contribute redundancy and fine-tuning function to the closed loop chemoreflex and baroreflex. In addition to sensing blood gasses, the carotid body is now understood to be sensitive to blood flow and velocity, blood Ph and glucose concentration. Thus it is understood that in conditions such as hypertension, CHF, insulin resistance, diabetes and other metabolic derangements afferent signaling of carotid body nerves may be elevated. Carotid body hyperactivity may be present even in the absence of detectable hypersensitivity to hypoxia and hypercapnia that are traditionally used to index carotid body function. The purpose of the proposed therapy is therefore to remove or reduce afferent neural signals from a carotid body and reduce carotid body contribution to central sympathetic tone.

The carotid sinus baroreflex is accomplished by negative feedback systems incorporating pressure sensors (e.g., baroreceptors) that sense the arterial pressure. Baroreceptors also exist in other places, such as the aorta and coronary arteries. Important arterial baroreceptors are located in the carotid sinus, a slight dilatation of the internal carotid artery 201 at its origin from the common carotid. The carotid sinus baroreceptors are close to but anatomically separate from the carotid body. Baroreceptors respond to stretching of the arterial wall and communicate blood pressure information to CNS. Baroreceptors are distributed in the arterial walls of the carotid sinus while the chemoreceptors (glomus cells) are clustered inside the carotid body. This makes the selective reduction of chemoreflex described in this application possible while substantially sparing the baroreflex.

The carotid body exhibits great sensitivity to hypoxia (low threshold and high gain). In chronic Congestive Heart Failure (CHF), the sympathetic nervous system activation that is directed to attenuate systemic hypoperfusion at the initial phases of CHF may ultimately exacerbate the progression of cardiac dysfunction that subsequently increases the extracardiac abnormalities, a positive feedback cycle of progressive deterioration, a vicious cycle with ominous consequences. It was thought that much of the increase in the sympathetic nerve activity (SNA) in CHF was based on an increase of sympathetic flow at a level of the CNS and on the depression of arterial baroreflex function. In the past several years, it has been demonstrated that an increase in the activity and sensitivity of peripheral chemoreceptors (heightened chemoreflex function) also plays an important role in the enhanced SNA that occurs in CHF.

Role of Altered Chemoreflex in CHF:

As often happens in chronic disease states, chemoreflexes that are dedicated under normal conditions to maintaining homeostasis and correcting hypoxia contribute to increase the sympathetic tone in patients with CHF, even under normoxic conditions. The understanding of how abnormally enhanced sensitivity of the peripheral chemosensors, particularly the carotid body, contributes to the tonic elevation in SNA in patients with CHF has come from several studies in animals. According to one theory, the local angiotensin receptor system plays a fundamental role in the enhanced carotid body chemoreceptor sensitivity in CHF. In addition, evidence in both CHF patients and animal models of CHF has clearly established that the carotid body chemoreflex is often hypersensitive in CHF patients and contributes to the tonic elevation in sympathetic function. This derangement derives from altered function at the level of both the afferent and central pathways of the reflex arc. The mechanisms responsible for elevated afferent activity from the carotid body in CHF are not yet fully understood.

Regardless of the exact mechanism behind the carotid body hypersensitivity, the chronic sympathetic activation driven from the carotid body and other autonomic pathways leads to further deterioration of cardiac function in a positive feedback cycle. As CHF ensues, the increasing severity of cardiac dysfunction leads to progressive escalation of these alterations in carotid body chemoreflex function to further elevate sympathetic activity and cardiac deterioration. The trigger or causative factors that occur in the development of CHF that sets this cascade of events in motion and the time course over which they occur remain obscure. Ultimately, however, causative factors are tied to the cardiac pump failure and reduced cardiac output. According to one theory, within the carotid body, a progressive and chronic reduction in blood flow may be the key to initiating the maladaptive changes that occur in carotid body chemoreflex function in CHF.

There is sufficient evidence that there is increased peripheral and central chemoreflex sensitivity in heart failure, which is likely to be correlated with the severity of the disease. There is also some evidence that the central chemoreflex is modulated by the peripheral chemoreflex. According to current theories, the carotid body is the predominant contributor to the peripheral chemoreflex in humans; the aortic body having a minor contribution.

Although the mechanisms responsible for altered central chemoreflex sensitivity remain obscure, the enhanced peripheral chemoreflex sensitivity can be linked to a depression of nitric oxide production in the carotid body affecting afferent sensitivity, and an elevation of central angiotensin II affecting central integration of chemoreceptor input. The enhanced chemoreflex may be responsible, in part, for the enhanced ventilatory response to exercise, dyspnea, Cheyne-Stokes breathing, and sympathetic activation observed in chronic heart failure patients. The enhanced chemoreflex may be also responsible for hyperventilation and tachypnea (e.g., fast breathing) at rest and exercise, periodic breathing during exercise, rest and sleep, hypocapnia, vasoconstriction, reduced peripheral organ perfusion and hypertension.

Dyspnea:

Shortness of breath, or dyspnea, is a feeling of difficult or labored breathing that is out of proportion to the patient's level of physical activity. It is a symptom of a variety of different diseases or disorders and may be either acute or chronic. Dyspnea is the most common complaint of patients with cardiopulmonary diseases.

Dyspnea is believed to result from complex interactions between neural signaling, the mechanics of breathing, and the related response of the central nervous system. A specific area has been identified in the mid-brain that may influence the perception of breathing difficulties.

The experience of dyspnea depends on its severity and underlying causes. The feeling itself results from a combination of impulses relayed to the brain from nerve endings in the lungs, rib cage, chest muscles, or diaphragm, combined with the perception and interpretation of the sensation by the patient. In some cases, the patient's sensation of breathlessness is intensified by anxiety about its cause. Patients describe dyspnea variously as unpleasant shortness of breath, a feeling of increased effort or tiredness in moving the chest muscles, a panicky feeling of being smothered, or a sense of tightness or cramping in the chest wall.

The four generally accepted categories of dyspnea are based on its causes: cardiac, pulmonary, mixed cardiac or pulmonary, and non-cardiac or non-pulmonary. The most common heart and lung diseases that produce dyspnea are asthma, pneumonia, COPD, and myocardial ischemia or heart attack (myocardial infarction). Foreign body inhalation, toxic damage to the airway, pulmonary embolism, congestive heart failure (CHF), anxiety with hyperventilation (panic disorder), anemia, and physical deconditioning because of sedentary lifestyle or obesity can produce dyspnea. In most cases, dyspnea occurs with exacerbation of the underlying disease. Dyspnea also can result from weakness or injury to the chest wall or chest muscles, decreased lung elasticity, obstruction of the airway, increased oxygen demand, or poor pumping action of the heart that results in increased pressure and fluid in the lungs, such as in CHF.

Acute dyspnea with sudden onset is a frequent cause of emergency room visits. Most cases of acute dyspnea involve pulmonary (lung and breathing) disorders, cardiovascular disease, or chest trauma. Sudden onset of dyspnea (acute dyspnea) is most typically associated with narrowing of the airways or airflow obstruction (bronchospasm), blockage of one of the arteries of the lung (pulmonary embolism), acute heart failure or myocardial infarction, pneumonia, or panic disorder.

Chronic dyspnea is different. Long-standing dyspnea (chronic dyspnea) is most often a manifestation of chronic or progressive diseases of the lung or heart, such as COPD, which includes chronic bronchitis and emphysema. The treatment of chronic dyspnea depends on the underlying disorder. Asthma can often be managed with a combination of medications to reduce airway spasms and removal of allergens from the patient's environment. COPD requires medication, lifestyle changes, and long-term physical rehabilitation. Anxiety disorders are usually treated with a combination of medication and psychotherapy.

Although the exact mechanism of dyspnea in different disease states is debated, there is no doubt that the CBC plays some role in most manifestations of this symptom. Dyspnea seems to occur most commonly when afferent input from peripheral receptors is enhanced or when cortical perception of respiratory work is excessive.

Surgical Removal of the Glomus and Resection of Carotid Body Nerves:

A surgical treatment for asthma, removal of the carotid body or glomus (glomectomy), was described by Japanese surgeon Komei Nakayama in 1940s. According to Nakayama in his study of 4,000 patients with asthma, approximately 80% were cured or improved six months after surgery and 58% allegedly maintained good results after five years. Komei Nakayama performed most of his surgeries while at the Chiba University during World War II. Later in the 1950's, a U.S. surgeon, Dr. Overholt, performed the Nakayama operation on 160 U.S. patients. He felt it necessary to remove both carotid bodies in only three cases. He reported that some patients feel relief the instant when the carotid body is removed, or even earlier, when it is inactivated by an injection of procaine (Novocain).

Overholt, in his paper Glomectomy for Asthma published in Chest in 1961, described surgical glomectomy the following way: "A two-inch incision is placed in a crease line in the neck, one-third of the distance between the angle of the mandible and clavicle. The platysma muscle is divided and the sternocleidomastoid retracted laterally. The dissection is carried down to the carotid sheath exposing the bifurcation. The superior thyroid artery is ligated and divided near its take-off in order to facilitate rotation of the carotid bulb and expose the medial aspect of the bifurcation. The carotid body is about the size of a grain of rice and is hidden within the adventitia of the vessel and is of the same color. The perivascular adventitia is removed from one centimeter above to one centimeter below the bifurcation. This severs connections of the nerve plexus, which surrounds the carotid body. The dissection of the adventitia is necessary in order to locate and identify the body. It is usually located exactly at the point of bifurcation on its medial aspect. Rarely, it may be found either in the center of the crotch or on the lateral wall. The small artery entering the carotid body is clamped, divided, and ligated. The upper stalk of tissue above the carotid body is then clamped, divided, and ligated."

In January 1965, the New England Journal of Medicine published a report of 15 cases in which there had been unilateral removal of the cervical glomus (carotid body) for the treatment of bronchial asthma, with no objective beneficial effect. This effectively stopped the practice of glomectomy to treat asthma in the U.S.

Winter developed a technique for separating nerves that contribute to the carotid sinus nerves into two bundles, carotid sinus (baroreflex) and carotid body (chemoreflex), and selectively cutting out the latter. The Winter technique is based on his discovery that carotid sinus (baroreflex) nerves are predominantly on the lateral side of the carotid bifurcation and carotid body (chemoreflex) nerves are predominantly on the medial side.

Neuromodulation of the Carotid Body Chemoreflex:

Hlavaka in U.S. Patent Application Publication 2010/0070004 filed Aug. 7, 2009, describes implanting an electrical stimulator to apply electrical signals, which block or inhibit chemoreceptor signals in a patient suffering dyspnea. Hlavaka teaches "some patients may benefit from the ability to reactivate or modulate chemoreceptor functioning." Hlavaka focuses on neuromodulation of the chemoreflex by selectively blocking conduction of nerves that connect the carotid body to the CNS. Hlavaka describes a traditional approach of neuromodulation with an implantable electric pulse generator that does not modify or alter tissue of the carotid body or chemoreceptors.

The central chemoreceptors are located in the brain and are difficult to access. The peripheral chemoreflex is modulated primarily by carotid bodies that are more accessible. Previous clinical practice had very limited clinical success with the surgical removal of carotid bodies to treat asthma in 1940s and 1960s.

ADDITIONAL EMBODIMENTS

Additional aspects of the invention are defined in accordance with the following exemplary embodiments:

1. A method for ablating a function of a carotid body in a patient comprising:
   a. determining a location of a target ablation site associated with the carotid body,
   b. percutaneously advancing an ablation device to a target ablation site of the patient, said ablation device comprising an elongated structure with a distal end and a proximal end, at least one ablation element mounted in the vicinity of said distal end, a means for connecting said ablation element to a source of ablation energy in the vicinity of said proximal end,
   c. delivering ablation energy via the ablation element to the target ablation site, to reduce chemoreflex, and
   d. removing the ablation device from the patient.
2. The method of claim 1 wherein the ablation device has a sharp distal tip and percutaneously advancing the ablation device to the target site comprises advancing the sharp distal tip of the ablation device through tissue.
3. The method of claim 1 further comprising a step of percutaneously advancing a cannula to a target ablation site and wherein percutaneously advancing the ablation device comprises advancing the ablation device through a lumen in the cannula.
4. The method of claim 1 further comprising a step of percutaneously advancing a dilation set to a target ablation site and wherein percutaneously advancing the ablation device comprises advancing the ablation device through a lumen in a dilator.
5. The method of any of claims 1 to 4 wherein the step of determining a location of a target ablation site comprises visualizing the target site with an imaging modality.
6. The method of claim 5 wherein visualizing the target site comprises focusing an ultrasound imaging transducer toward the target site.
7. The method of claim 6 wherein the ultrasound imaging transducer comprises an instrument guide and wherein percutaneously advancing the ablation device comprises advancing the ablation device through the instrument guide.
8. The method of claim 1 wherein, parameters of delivering ablation energy are predetermined based in part on the location of the carotid body.
9. The method of claim 1 wherein size of a carotid body is determined.
10. The method of claim 9 wherein the parameters of delivering ablation energy are predetermined based in part on the size of said carotid body.
11. The method of any of claims 1 to 10 further involving a step of placing an embolization protection device into an internal carotid artery.
12. The method of any of claims 1 to 11 wherein a parameter of delivering ablation energy is ablation element temperature.
13. The method of any of claims 1 to 11 wherein a parameter of delivering ablation energy is tissue temperature.
14. The method of any of claims 1 to 11 wherein a parameter of delivering ablation energy is duration of energy delivery.
15. The method of any of claims 1 to 11 wherein a parameter of delivering ablation energy is power.
16. The method of any of claims 1 to 11 wherein a parameter of delivering ablation energy is location of placement of the ablation element.
17. The method any of claims 1 wherein determining the carotid body location comprises an imaging study.
18. The method of claim 17 wherein the size of a carotid body is determined.
19. The method of claim 17 or 18 wherein the imaging study comprises Computed Tomography Angiography.
20. The method of claim 17 or 18 wherein the imaging study comprises MR Angiography.
21. The method of claim 17 or 18 wherein the imaging study comprises sonography.
22. The method of claim 21 wherein the sonography comprises intra-vascular ultrasound.
23. The method of claim 17 wherein fiducial markers are positioned on the patient during the imaging study.
24. The method of claim 23 wherein the fiducial markers are positioned on the patient during the step of percutaneously advancing the ablation device to the target ablation site.
25. The method of claim 24 wherein an image acquired from the imaging study is overlaid on an image acquired during the step of percutaneously advancing the ablation device to the target ablation site.
26. The method of any of claims 1 to 22 wherein a function of the carotid body is stimulated.
27. The method of claim 26 wherein said stimulation comprises application of electrical energy.
28. The method of claim 27 wherein said electrical energy is applied by an electrode mounted in the vicinity of the distal end of the ablation device.
29. The method of claim 26 wherein said stimulation comprises administration of a chemical agent.
30. The method of claim 26 wherein said stimulation comprises a manipulation in the composition of inhaled gas.
31. The method of any of claims 26 through 30 wherein the carotid body is stimulated prior to said ablation and after said ablation.
32. The method of claim 1 wherein a function of the carotid body is blocked.
33. The method of claim 32 wherein said blockage comprises application of electrical energy.
34. The method of claim 32 wherein said electrical energy is applied by an electrode mounted in the vicinity of the distal end of the ablation device.
35. The method of claim 32 wherein said blockage comprises administration of a chemical agent.
36. The method of claim 32 wherein said blockage comprises a manipulation in composition of inhaled gas.
37. The method of any of claims 32 through 36 wherein a function of the carotid body is blocked prior to said ablation and after said ablation.
38. The method of any of claims 1 to 37 further comprising a step of repeating steps b through d with the ablation element placed at an additional location.
39. The method of claim 38 wherein steps b through d are repeated with the ablation element placed at more than one predetermined location.
40. The method of any of claims 1 to 39 further comprising the step of repeating steps b through d with the ablation element placed at the same location.
41. The method of any of claims 1 to 39 wherein the ablation device is a probe and the ablation element comprises a temperature sensor.
42. The method of claim 41 wherein the temperature sensor is connectable to a source of ablation energy by means of electrical wires located within the probe between the temperature sensor and an electrical connector located at the proximal end of the probe.

43. The method of claim 41 or 42 wherein the temperature sensor is configured for controlling the ablation energy source in order to maintain the ablation element within a predetermined ablation temperature range.
44. The method of any of claims 1 to 43 wherein the ablation device is a probe with a functional length between 3 and 20 cm.
45. The method of any of claims 1 to 44 wherein the ablation device is a probe with a diameter of less than 5 mm.
46. The method of any of claims 1 to 45 wherein the ablation device comprises an optic fiber and the ablation energy is laser.
47. The method of claim 46 wherein the ablation element is a forward-facing port through which laser energy is emitted.
48. The method of claim 46 wherein the ablation element is a side-facing port through which laser energy is emitted.
49. The method of any of claims 1 to 45 wherein the ablation device comprises a waveguide and the ablation energy is low frequency ultrasound.
50. The method of any of claims 1 to 45 wherein the ablation element comprises at least one electrode.
51. The method of claim 50 wherein the electrode(s) is radiopaque.
52. The method of claim 50 wherein the electrode(s) is configured to electrically stimulate carotid body function.
53. The method of claim 50 wherein the electrode(s) is configured to electrically block carotid body function.
54. The method of any of claims 50 to 53 wherein the electrode(s) is connectable to a source of electrical energy by means of an electrical conducting wire(s) located within the probe between the electrode(s) and an electrical connector located in the vicinity of the proximal end of the probe.
55. The method of any of claim 50 wherein the ablation energy is alternating current electricity at an alternating frequency greater than 400 kHz.
56. The method of claim 46 wherein the ablation element temperature is preselected in a range between 40 Deg. C. and 100 Deg. C.
57. The method of claim 46 wherein the electrode is actively cooled.
58. The method of any of claims 1 to 45 wherein the ablation element comprises a cryo-ablation element.
59. The method of claim 58 wherein the cryo-ablation element comprises a cryogen expansion chamber.
60. The method of claim 58 wherein the ablation element temperature is preselected in a range of −20 Deg. C. to −180 Deg. C.
61. The method of any of claims 1 to 58 wherein the parameter of delivering ablation energy is selected for reversible ablation.
62. The method of claim 61 wherein reversible ablation comprises a temporary cryogenic nerve block, the method further comprising monitoring physiological responses to said temporary nerve block to confirm that the ablation element is sufficiently proximate the target ablation site.
63. The method of claim 61 or 62 wherein reversible ablation comprises a temporary cryogenic nerve block, the method further comprising monitoring physiological responses to said temporary nerve block to confirm that the ablation element is sufficiently distant from a nerve selected from a group consisting of vagus nerve, cervical sympathetic nerve, hypoglossal nerve, and superior laryngeal nerve.
64. The method of claim 1 wherein the ablation device comprises a means for imaging a carotid body and surrounding anatomy.
65. The method of claim 64 wherein said imaging is ultrasonic.
66. The method of claim 64 wherein said imaging is configured for imaging a change in carotid body resulting from ablation.
67. The method of any of claims 1 to 66 further comprising a step of thermally protecting a region of tissue proximate the target ablation site.
68. The method of claim 67 wherein the ablation device further comprises a protective element in a vicinity of the distal end.
69. The method of claim 68 wherein the ablation element is configured to increase tissue temperature and the protective element is configured to impede the increase of tissue temperature in the tissue proximate the target ablation site.
70. The method of claim 68 wherein the ablation element is configured to decrease tissue temperature and the protective element is configured to impede the decrease of tissue temperature in the tissue proximate the target ablation site.
71. A method of any of claims 1 to 67 further comprising a step of protecting a region of tissue proximate the target ablation site by increasing distance between the region of tissue and the target ablation site.
72. A device for ablating a function of a carotid body comprising:
a shaft comprising a distal end and a proximal end,
an articulating arm in a vicinity of the distal end comprising an ablation element,
a handle in the vicinity of the proximal end comprising a means for controlling the articulating arm, and
a means for connecting said ablation element to a source of ablation energy.
73. The device of claim 72 wherein the device is configured for use in a percutaneous dilator with a working channel no greater than 10 mm wide.
74. The device of claim 72 wherein the shaft has a length between 3 and 20 cm and the articulating arm has a length between 0.5 to 3 cm.
75. The device of claim 72 configured to deliver an ablation energy selected from a list comprising radiofrequency electrical current, cryogenic energy, high intensity focused ultrasound, laser, chemical, bipolar radiofrequency electrical current, microwave, and low frequency ultrasound.
76. The device of claim 72 configured to mechanically ablate tissue.
77. A device for percutaneously ablating a function of a carotid body comprising: a shaft comprising a distal end and a proximal end, a protection element positioned in a vicinity of the distal end, an ablation element positioned in a vicinity of the distal end, a handle in the vicinity of the proximal end, a means for connecting the ablation element to a source of ablation energy, and a means for connecting the protection element to a source of protection energy.
78. A device of claim 77 wherein the protection element is positioned distal to the ablation element.

79. A device of claim 77 wherein the ablation element is a cryo-ablation element and the protection element is a radiofrequency electrode.

80. A device for holding a neck of a patient in a position suitable for carotid body ablation, the device comprising an adjustable neck rotator adjustable to an angle between 0 and 45 degrees to the left or right, an adjustable neck extender adjustable to an angle between 0 and 20 degrees, fiducial markers, and a working window.

81. A device of claim 80 further comprising a needle guide.

82. A system for ablating a function of a carotid body in a patient comprising:
   An ablation device configured for use in a vicinity of an intercarotid septum comprising a distal end and a proximal end, a radiopaque ablation element, a handle in a vicinity of the proximal end, and a means for connecting the ablation element to a source of ablation energy;
   a console comprising a source of ablation energy and a means for controlling the ablation energy, a user interface configured to provide a selection of ablation parameters and indications of console status and ablation activity status, and a means to activate and deactivate an ablation;
      an umbilical cable configured to connect the console to the ablation device;
   whereby, the ablation device provides a means for user placement of the ablation element into an optimal position within the intercarotid septum for ablation, and the console provides the means for user selection of optimal ablation parameters.

83. The system of claim 82 wherein the console further comprises a source of protection energy and a means for controlling the protection energy.

84. The system of claim 83 wherein the ablation energy is cryogenic energy and the protection energy is radiofrequency electrical current.

85. The system of claim 83 wherein the ablation energy is radiofrequency electrical current and the protection energy is cryogenic energy.

86. The system of claim 82 further comprising a cannula and trocar.

87. The system of claim 82 further comprising a dilation set.

88. The system of claim 82 wherein the ablation element and the console are configured for electrical stimulation of a function of a carotid body.

89. The system of claim 82 wherein the ablation element and the console are configured for electrical blockade of the function of a carotid body.

90. The system of claim 82 wherein the ablation device and the console are configured for irrigation of the vicinity of the ablation element with a physiological solution.

91. The system of claim 82 wherein the source of ablation energy comprises a container of cryogenic fluid.

92. A method for percutaneous chemoreceptor neuromodulation, the method comprising:
   a) percutaneously positioning an ablation device having a therapeutic element through skin of a human patient and proximate a chemoreceptor or chemoreceptor nerves; and
   b) reducing neural traffic within the patient due to the therapeutic element,
   wherein reducing the neural traffic therapeutically treats a diagnosed condition of disease associated with autonomic imbalance.

93. A method for percutaneous chemoreceptor ablation, the method comprising:
   a) positioning an ablation device having an ablation element through skin of a human patient and proximate a chemoreceptor or chemoreceptor nerves; and
   b) reducing chemoreceptor neural traffic within the patient due to the ablation element,
   wherein reducing the chemoreceptor neural traffic therapeutically treats a diagnosed condition of disease associated with autonomic imbalance.

94. A method for treating a patient comprising:
   a) locating a region in the patient including a carotid body,
   b) inserting into the patient an ablation device, said ablation device comprising a distal region and a proximal region, an ablation element mounted to said distal region, a connection extending through the ablation device from the distal region to the proximal region wherein energy or a fluid to receive heat energy is delivered to the proximal region through the connection to the ablation element;
   c) advancing the distal region of said ablation device through tissue of the patient;
   d) positioning the distal region in interstitial space at a location proximate to said carotid body region;
   e) transferring heat energy from said ablation device to the tissue or from the tissue to the ablation device to ablate tissue in the region that includes the carotid body, and
   f) withdrawing the ablation device from the patient.

We claim:

1. A method of cryo-ablating a carotid septum and protecting tissue, comprising
   positioning a cryo-ablation element within a carotid septum;
   positioning a warming element distal to the cryo-ablation element;
   activating the cryo-ablation element and ablating carotid septum tissue adjacent the cryo-ablation element by reducing the temperature of the carotid septum tissue adjacent the cryo-ablation element;
   warming tissue proximate the warming element by activating the warming element to prevent the tissue proximate the warming element from being reduced as much as the carotid septum tissue adjacent the cryo-ablation element.

2. The method of claim 1 wherein the method further comprises providing a cryo-ablation device that supports the cryo-ablation element and the warming element, the warming element disposed distal to the cryo-ablation element.

3. The method of claim 1 wherein activating the cryo-ablation element comprises delivering a cryogen fluid through the cryo-ablation element.

4. The method of claim 1 further comprising piercing the carotid septum before the positioning steps.

5. The method of claim 1 further comprising piercing the skin in the neck to create an access path to the carotid septum.

6. The method of claim 5 further comprising advancing a cryo-ablation device into the patient via the access point, the cryo-ablation device comprising the cryo-ablation element and the warming element.

7. The method of claim 1 wherein positioning the cryo-ablation element within a carotid septum comprises positioning the cryo-ablation element adjacent a carotid body and between an external carotid artery and an internal carotid artery.

8. The method of claim 7 wherein positioning the warming element distal to the cryo-ablation element comprises positioning the warming element closer to a sympathetic nerve than the cryo-ablation element.

9. The method of claim 1 further comprising imaging the carotid body before either activating step.

* * * * *